(12) United States Patent
El-Toufaili et al.

(10) Patent No.: US 11,643,491 B2
(45) Date of Patent: *May 9, 2023

(54) PROCESS FOR PRODUCING AN AQUEOUS POLYACRYLAMIDE CONCENTRATE

(71) Applicant: BASF SE, Ludwigshafen am Rhein (DE)

(72) Inventors: Faissal-Ali El-Toufaili, Ludwigshafen (DE); Dennis Loesch, Ludwigshafen (DE); Anna-Corina Schmidt, Trostberg (DE); Tobias Joachim Zimmermann, Ludwigshafen (DE); Markus Ostermayr, Ludwigshafen (DE); Jack F. Tinsley, Houston, TX (US); Brent Busby, Houston, TX (US)

(73) Assignee: BASF SE, Ludwigshafen am Rhein (DE)

( * ) Notice: Subject to any disclaimer, the term of this patent is extended or adjusted under 35 U.S.C. 154(b) by 81 days.

This patent is subject to a terminal disclaimer.

(21) Appl. No.: 17/286,468

(22) PCT Filed: Oct. 17, 2019

(86) PCT No.: PCT/EP2019/078218
§ 371 (c)(1),
(2) Date: Apr. 18, 2021

(87) PCT Pub. No.: WO2020/079152
PCT Pub. Date: Apr. 23, 2020

(65) Prior Publication Data
US 2021/0347924 A1 Nov. 11, 2021

(30) Foreign Application Priority Data
Oct. 18, 2018 (WO) .................. PCT/EP2018/078488

(51) Int. Cl.
*C08F 220/56* (2006.01)
*B01J 19/06* (2006.01)
(Continued)

(52) U.S. Cl.
CPC ............. *C08F 220/56* (2013.01); *B01J 19/06* (2013.01); *C08J 3/075* (2013.01); *C09K 8/588* (2013.01);
(Continued)

(58) Field of Classification Search
None
See application file for complete search history.

(56) References Cited

U.S. PATENT DOCUMENTS 4,248,304 A 2/1981 Phillips
4,605,689 A 8/1986 Witheford et al.
(Continued)

FOREIGN PATENT DOCUMENTS

CN 202492486 U 10/2012
DE 2059241 A1 6/1972
(Continued)

OTHER PUBLICATIONS

Database WPI, Week 198418, Thomson Scientific, retrieved from STN Database accession No. 1984-113907, XP002791209, Jan. 10, 1984, 2 pages.
(Continued)

*Primary Examiner* — John J Figueroa
(74) *Attorney, Agent, or Firm* — Faegre Drinker Biddle & Reath LLP

(57) ABSTRACT

Process for producing aqueous polyacrylamide concentrates by polymerizing an aqueous solution comprising at least acrylamide thereby obtaining an aqueous polyacrylamide gel, comminuting said aqueous polyacrylamide gel and mixing it with an aqueous liquid, wherein the manufacturing
(Continued)

steps are allocated to two different locations A and B and the process comprises the step of transporting an aqueous polyacrylamide concentrate hold in a suitable transport unit from a location A to a location B. Modular, relocatable plant for manufacturing aqueous polyacrylamide, wherein the units of the plant are located at two different locations A and B.

22 Claims, 14 Drawing Sheets

(51) Int. Cl.
  *C08J 3/075*    (2006.01)
  *C09K 8/588*    (2006.01)
  *C09K 8/68*     (2006.01)
  *C12P 13/02*    (2006.01)

(52) U.S. Cl.
  CPC .............. *C09K 8/68* (2013.01); *C12P 13/02* (2013.01); *C12Y 402/01084* (2013.01); *B01J 2219/0002* (2013.01); *C08F 2800/10* (2013.01); *C08F 2800/20* (2013.01)

(56) References Cited

U.S. PATENT DOCUMENTS

| | | | |
|---|---|---|---|
| 4,845,192 | A | 7/1989 | Sortwell et al. |
| 11,384,177 | B2 * | 7/2022 | Zimmermann ....... C08F 220/56 |
| 2004/0175809 | A1 | 9/2004 | Peterson et al. |
| 2020/0308314 | A1 * | 10/2020 | Sprafke ................. C12N 9/78 |
| 2021/0070904 | A1 * | 3/2021 | Loesch ................ E21B 21/003 |
| 2021/0179758 | A1 * | 6/2021 | Sprafke .................. E21B 43/26 |
| 2021/0347924 | A1 * | 11/2021 | El-Toufaili .............. C08J 3/075 |

FOREIGN PATENT DOCUMENTS

| | | |
|---|---|---|
| EP | 2336346 A1 | 6/2011 |
| EP | 2518154 A1 | 10/2012 |
| GB | 1375979 A | 12/1974 |
| JP | 2014-176344 A | 9/2014 |
| JP | 2015-057968 A | 3/2015 |
| WO | 84/00967 A1 | 3/1984 |
| WO | 97/21827 A1 | 6/1997 |
| WO | 03/66190 A1 | 8/2003 |
| WO | 2005/054456 A1 | 6/2005 |
| WO | 2005/054489 A1 | 6/2005 |
| WO | 2010/133527 A2 | 11/2010 |
| WO | 2012/069478 A1 | 5/2012 |
| WO | 2015/024865 A1 | 2/2015 |
| WO | 2015/086468 A1 | 6/2015 |
| WO | 2015/158517 A1 | 10/2015 |
| WO | 2016/006556 A1 | 1/2016 |
| WO | 2016/050816 A2 | 4/2016 |
| WO | 2016/050817 A1 | 4/2016 |
| WO | 2016/050818 A1 | 4/2016 |
| WO | 2016/050819 A1 | 4/2016 |
| WO | 2016/050861 A1 | 4/2016 |
| WO | 2016/131940 A1 | 8/2016 |
| WO | 2016/131941 A1 | 8/2016 |
| WO | 2017/055518 A1 | 4/2017 |
| WO | 2017/167803 A1 | 10/2017 |
| WO | 2017/186567 A1 | 11/2017 |
| WO | 2017/186685 A1 | 11/2017 |
| WO | 2017/186697 A1 | 11/2017 |
| WO | 2017/186698 A1 | 11/2017 |
| WO | 2019/081318 A1 | 5/2019 |
| WO | 2019/081319 A1 | 5/2019 |
| WO | 2019/081320 A1 | 5/2019 |
| WO | 2019/081321 A1 | 5/2019 |
| WO | 2019/081323 A1 | 5/2019 |
| WO | 2019/081327 A1 | 5/2019 |
| WO | 2019/081330 A1 | 5/2019 |
| ZA | 833812 | 2/1984 |
| ZA | 8303812 | 2/1984 |

OTHER PUBLICATIONS

International Preliminary Report on Patentability received for PCT Patent Application No. PCT/EP2019/078218, dated Apr. 29, 2021, 16 pages.

International Search Report and Written Opinion received for PCT Patent Application No. PCT/EP2018/078488, dated May 20, 2019, 6 pages.

International Search Report and Written Opinion received for PCT Patent Application No. PCT/EP2019/078218, dated Nov. 11, 2019, 20 pages.

Rogovina et al., "Definition of the concept of polymer gel", Polymer Science Ser. C, vol. 50, No. 1, 2008, pp. 85-92.

* cited by examiner

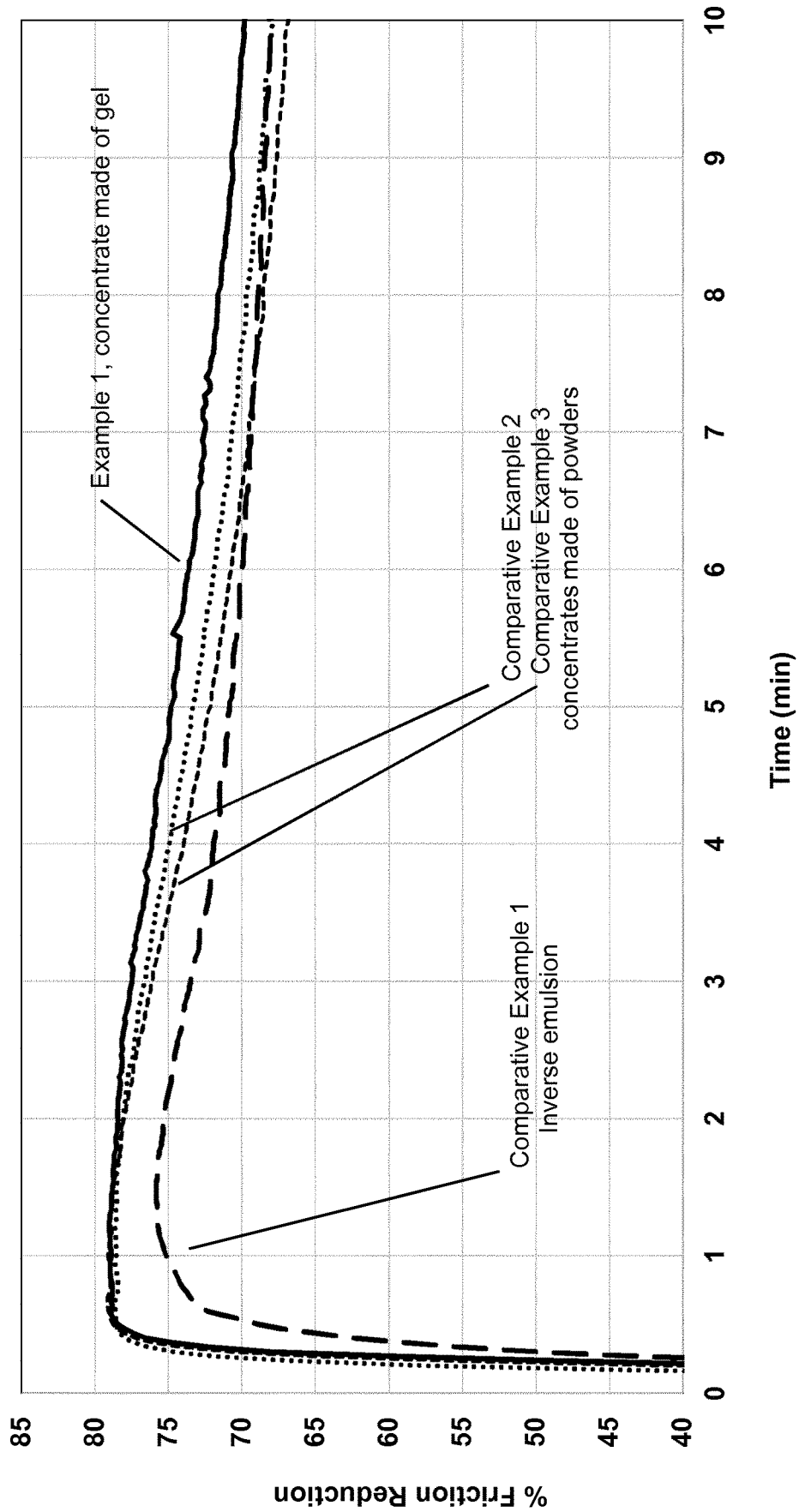
Figure 17: Results of the tests in the Friction Loop

PROCESS FOR PRODUCING AN AQUEOUS POLYACRYLAMIDE CONCENTRATE

CROSS-REFERENCE TO RELATED APPLICATIONS

This application is a national stage application (under 35 U.S.C. § 371) of PCT/EP2019/078218, filed Oct. 17, 2019, which claims benefit of PCT/EP2018/078488, filed Oct. 18, 2018, both of which are incorporated herein by reference in their entirety.

The invention relates to a process for producing aqueous polyacrylamide concentrates by polymerizing an aqueous solution comprising at least acrylamide thereby obtaining an aqueous polyacrylamide gel, comminuting said aqueous polyacrylamide gel and mixing it with an aqueous liquid, wherein the manufacturing steps are allocated to two different locations A and B and the process comprises the step of transporting an aqueous polyacrylamide concentrate hold in a suitable transport unit from a location A to a location B. The invention furthermore relates to a modular, relocatable plant for manufacturing aqueous polyacrylamide, wherein the units of the plant are located at two different locations A and B.

Water-soluble, high molecular weight homo- and copolymers of acrylamide may be used for various applications such as mining and oilfield applications, water treatment, sewage treatment, papermaking, and agriculture. Examples include its use in the exploration and production of mineral oil, in particular as thickener in aqueous injection fluids for enhanced oil recovery or as rheology modifier for aqueous drilling fluids. Further examples include its use as flocculating agent for tailings and slurries in mining activities.

A common polymerization technology for manufacturing such high molecular weight polyacrylamides is the so called "gel polymerization". In gel polymerization, an aqueous monomer solution having a relatively high concentration of monomers, for example from 20% by weight to 50% by weight is polymerized by means of suitable polymerization initiators under essentially adiabatic conditions in an unstirred reactor thereby forming a polymer gel. The polymer gels formed are converted to polymer powders by comminuting the gel into smaller pieces by one or more size reduction steps, drying such gel pieces for example in a fluid bed dryer followed by sieving, grinding and packaging. The obtained polyacrylamide powders are thereafter packaged and shipped to customers.

The aqueous polyacrylamide gel obtained from gel polymerization typically comprises from 65% to 80% of water. The residual amount of water in polyacrylamide powders typically is from about 4 to 12% by weight. So, "drying" such polyacrylamide gels does not mean to remove only some residual moisture in course of drying but rather about 0.55 to 0.75 kg of water need to be removed per kg of polymer gel, or—with other words—per kg of polymer powder produced also 1.5 to 2.5 kg of water are "produced".

It goes without saying that removing such a high amount of water from the aqueous polymer gels in course of drying is energy extensive and consequently the operational costs for drying are high. Furthermore, high-performance dryers are necessary as well as equipment for size reduction, sieving and grinding. Consequently, the capital expenditure for the entire post-processing equipment including size reduction, drying, sieving, grinding is significant in relation to the total capital expenditure for the entire plant.

High-molecular weight polyacrylamides are usually used as dilute aqueous solutions. Typical concentrations of polyacrylamides for oilfield and mining applications range from 0.05 wt. % to 0.5 wt. %. Consequently, the polyacrylamide powders manufactured as mentioned above need to be dissolved in aqueous fluids before use. Dissolving high molecular weight polymers in aqueous fluids is time consuming and it is difficult to do so without degrading the polymers and without forming lumps. Suitable equipment for dissolving polyacrylamide powders is necessary on-site.

For oilfield applications, such as enhanced oil recovery or for mining applications large amounts of polyacrylamides need to be available at one location, i.e. at an oilfield or at a mining area. By way of example, even for flooding only a medium size oilfield it may be necessary to inject some thousand $m^3$ of polymer solution per day into the oil-bearing formation and usually the process of polymer flooding continues for months or even years. So, for a polymer concentration of only 0.2 wt. % and an injection rate of 5000 $m^3$/day 10 t of polymer powder are needed per day and need to be dissolved in an aqueous fluid.

It has been suggested not to dry the aqueous polyacrylamide gels after manufacture but directly dissolving said polyacrylamide gels in water thereby obtaining diluted aqueous solutions of polyacrylamides without drying and re-dissolving the dry powder. Working in such a manner saves capital expenditures and operational costs for drying and further post-processing. However, shipping dilute aqueous solutions of polyacrylamides to customers is not an option because transport costs become extremely high as compared to transporting powders. It has therefore been suggested to manufacture aqueous polyacrylamide solutions on-site.

DE 2 059 241 discloses a process for preparing water-soluble polymers, including acrylamide containing polymers, in which an aqueous solution comprising water-soluble monomers and polymerization initiators is filled into transportable containers for polymerization. In the transportable containers, the aqueous solution polymerizes thereby forming polymer gel. The gel may be transported to the end users who can remove the polymer gels and dissolve them in water. The transportable containers may be—for instance—bags, cans, drums, or boxes having a volume from 2 l to 200 l.

U.S. Pat. No. 4,248,304 discloses a process for recovering oil from subterranean formations wherein a water-in-oil-emulsion of an acrylamide polymer in the presence of an inverting agent is injected into the formation. The water-in-oil emulsion is manufactured in a small chemical plant located near the wells and the manufacturing procedure comprises the steps of forming a water-in-oil emulsion of acrylonitrile, converting a substantially portion of the acrylonitrile to acrylamide using a suitable catalyst, and polymerizing the water-in-oil emulsion of acrylamide in the presence of a free radical polymerization catalyst. The catalyst may be a copper catalyst.

ZA 8303812 discloses a process for preparing polyacrylamides comprising polymerizing acrylamide and optionally suitable comonomers on-site and transferring the polymer formed to its desired place of use on site without drying or concentrating. The polymerization can be carried out as an emulsion polymerization, bead polymerization, or as solution/dispersion polymerization. The polymer may be pumped from the polymerization reactor to the position on site where it is used.

WO 84/00967 A1 discloses an apparatus and method for the continuous production of aqueous polymer solutions, in particular partially hydrolyzed polyacrylamide. The apparatus comprises a polymerization reactor, a hydrolysis reactor and a diluter. The polymerization may be performed on-site and the solutions may be used in secondary or tertiary oil recovery.

U.S. Pat. No. 4,605,689 discloses a method for on-site production of aqueous polyacrylamide solutions for enhanced oil recovery. In a first step an aqueous polyacrylamide gel is provided by polymerizing acrylamide and preferably acrylic acid as comonomer. The polyacrylamide gel obtained is conveyed together with a minor amount of aqueous solvent through at least one static cutting device thereby obtaining a slurry of small gel particles in water, the gel particles are dissolved in the aqueous solvent which forms a homogeneous solution concentrate which is then readily diluted with aqueous solvent thereby obtaining a diluted aqueous polyacrylamide solution.

U.S. Pat. No. 4,845,192 discloses a method of rapidly dissolving particles of gels of water-soluble polymers comprising forming a suspension of such gel particles in water and subjecting said suspension to instantaneous and momentary conditions of high shearing effective to finely slice said particles.

WO 2017/186567 A1 relates to a process for producing an aqueous polymer solution comprising the steps of providing an aqueous polyacrylamide gel comprising at least 10% by weight of active polymer, cutting the aqueous polyacrylamide gel by means of an aqueous liquid at a pressure of at least 150 bar to reduce the size of the aqueous polyacrylamide gel, and dissolving the aqueous polyacrylamide gel in an aqueous liquid.

WO 2017/186697 A1 relates to a method of preparing an aqueous polyacrylamide solution, comprising hydrolyzing acrylonitrile in water in presence of a biocatalyst thereby obtaining an acrylamide solution, directly polymerizing the acrylamide solution thereby obtaining a polyacrylamide gel, and directly dissolving the polyacrylamide gel by addition of water thereby obtaining an aqueous polyacrylamide solution which may have a concentration from 0.03% to 5% by weight. The method may be carried out on-site.

WO 2017/186685 A1 relates to a method of preparing an aqueous polyacrylamide solution, comprising hydrolyzing acrylonitrile in water in presence of a biocatalyst thereby obtaining an acrylamide solution, directly polymerizing the acrylamide solution thereby obtaining a polyacrylamide gel, and directly dissolving the polyacrylamide gel by addition of water by means of a mixer comprising a rotatable impeller thereby obtaining an aqueous polyacrylamide solution, which may have a concentration from 0.03% to 5% by weight. The method may be carried out on-site.

WO 2017/186698 A1 relates to a method of preparing an aqueous polyacrylamide solution, comprising hydrolyzing acrylonitrile in water in presence of a biocatalyst thereby obtaining an acrylamide solution, directly polymerizing the acrylamide solution thereby obtaining a polyacrylamide gel, and directly dissolving the polyacrylamide gel by addition of water by means of water-jet cutting, thereby obtaining an aqueous polyacrylamide solution, which may have a concentration from 0.03% to 5% by weight. The method may be carried out on-site.

WO 2016/006556 A1 describes a method for producing a compound using a continuous tank reactor which is provided with two or more reaction tanks for producing the compound and with a reaction liquid feeding pipe that feeds a reaction liquid from an upstream reaction tank to a downstream reaction tank, said method being characterized in that the Reynold's number of the reaction liquid that flows in the reaction liquid feeding pipe is configured to be 1800-22000. The tank reactor may be mounted in a portable container. The compound may be acrylamide produced by conversion from acrylonitrile by means of a biocatalyst.

WO 2017/167803 A1 discloses a method for producing a polyacrylamide solution having an increased viscosity by preparing an aqueous acrylamide solution by converting acrylonitrile to acrylamide using a biocatalyst, separating the biocatalyst from the aqueous acrylamide solution such that the $OD_{600}$ of the aqueous acrylamide solution is equal or less than 0.6, and polymerizing the aqueous acrylamide solution thus obtained to polyacrylamide.

WO 97/21827 A1 discloses a process for making a solution of ammonium acrylate by enzymatic hydrolysis of acrylonitrile.

Our older applications WO 2019/081318 A1, WO 2019/081319 A1, WO 2019/081320 A1, WO 2019/081321 A1, WO 2019/081323 A1, WO 2019/081327 A1, and WO 2019/081330 A1 disclose the manufacture of aqueous polyacrylamide solutions on-site in modular plants. In the modular plants disclosed aqueous solutions comprising acrylamide and optionally further monoethylenically unsaturated comonomers are polymerized by adiabatic gel polymerization in a polymerization unit which preferably has a volume of 20 $m^3$ to 30 $m^3$. Such a polymerization may be performed at a location A and thereafter the relocatable polymerization unit filled with the aqueous polyacrylamide gel is transported to another location B where the gel is removed from the polymerization unit, comminuted and dissolved in water thereby yielding an aqueous polyacrylamide solution. Location B typically is a location where the aqueous polyacrylamide solutions are used, e.g. at an oil well or in mining area. Location A typically is a central hub comprising units for monomer storage, monomer make-up and polymerization which serves a number of different locations B with aqueous polyacrylamide gel. Locations A and B may be apart from each other significantly, for example the distance may be up to 3000 km and the transport of the gel form location A to location B may last several days.

The production of polyacrylamide solution on-site saves equipment and operational costs for drying and re-dissolving of polyacrylamides on the one hand. On the other hand, for every point of consumption a separate plant is necessary which also requires a significant investment. Furthermore, raw materials for the production need to be shipped to a large plurality of sites which causes significant costs for transport and logistics.

It was an object of the present invention to provide an improved process for manufacturing aqueous solutions of polyacrylamides which avoids building a complete plant for every point of consumption.

Accordingly, in one embodiment the present invention relates to a process for producing an aqueous polyacrylamide concentrate by polymerizing an aqueous solution comprising at least acrylamide thereby obtaining an aqueous polyacrylamide gel and mixing said aqueous polyacrylamide gel with an aqueous liquid, characterized in that the process comprises at least the following steps:

[1] Radically polymerizing an aqueous monomer solution in the presence of suitable initiators for radical polymerization under adiabatic conditions in a polymerization unit at a location A,
wherein the aqueous monomer solution comprises at least water and 15% to 50% by weight—relating to the total of all components of the aqueous monomer solution—of water-soluble, monoethylenically unsaturated monomers at a location A, wherein said water-soluble, monoethylenically unsaturated monomers comprise at least acrylamide, thereby obtaining an aqueous polyacrylamide gel which is hold in the polymerization unit,

[2] removing the aqueous polyacrylamide gel from the polymerization unit at the location A,

[3] comminuting the aqueous polyacrylamide gel and mixing it with an aqueous liquid at the location A, thereby obtaining an aqueous polyacrylamide concentrate having a concentration of 1.0 to 14.9% by weight of polyacrylamides, relating to the total of all components of the aqueous polyacrylamide concentrate,

[4] transporting the aqueous polyacrylamide concentrate in a transport unit having a volume from 1 $m^3$ to 40 $m^3$ by transport means selected from the group of trucks, railcars or ships from location A to a different location B, and

[5] removing the aqueous polyacrylamide concentrate from the transport unit at the location B.

In one embodiment, the present invention comprises an additional step [6] of diluting the aqueous polyacrylamide concentrate in a second step at location B.

| List of figures: | |
|---|---|
| FIG. 1 | Schematic representation of a storage unit for monomers with internal temperature control unit. |
| FIG. 2 | Schematic representation of a storage unit for monomers with external temperature control unit. |
| FIG. 3 | Schematic representation of a bio acrylamide reactor. |
| FIG. 4 | Schematic representation of a monomer make-up unit. |
| FIG. 5 | Schematic representation of a polymerization unit P1. |
| FIG. 6 | Schematic representation of a polymerization unit P1 connected with comminution unit. |
| FIG. 7 | Schematic representation of a water-jet cutting unit. |
| FIG. 8 | Schematic representation of another embodiment of a water-jet cutting unit. |
| FIG. 9 | Schematic representation of another embodiment of a water-jet cutting unit. |
| FIG. 10 | Schematic representation of another embodiment of a water-jet cutting unit. |
| FIG. 11 | Schematic representation of a water-jet cutting unit comprising additionally static cutting units. |
| FIG. 12 | Schematic representation of a water-jet cutting unit combined with a hole perforation plate (one nozzle). |
| FIG. 13 | Schematic representation of a water-jet cutting unit combined with a hole perforation plate (more than one nozzles). |
| FIG. 14 | Schematic representation of a water-jet cutting unit combined with a hole perforation plate (one nozzle). |
| FIG. 15 | Schematic representation of a water-jet cutting unit combined with a hole perforation plate (more than one nozzles). |
| FIG. 16 | Schematic representation of a cutting unit comprising a hole perforation plate and a rotating knife. |
| FIG. 17 | Result of the friction loop tests |

With regard to the invention, the following can be stated specifically:

By means of the process according to the present invention, it is possible to prepare polyacrylamides.

Polyacrylamides

The term "polyacrylamides" as used herein means water-soluble homopolymers of acrylamide, or water-soluble copolymers comprising at least 10%, preferably at least 20%, and more preferably at least 30% by weight of acrylamide and at least one additional water-soluble, monoethylenically unsaturated monomer different from acrylamide, wherein the amounts relate to the total amount of all monomers in the polymer. Copolymers are preferred.

The term "water-soluble monomers" in the context of this invention means that the monomers are to be soluble in the aqueous monomer solution to be used for polymerization in the desired use concentration. It is thus not absolutely necessary that the monomers to be used are miscible with water without any gap; instead, it is sufficient if they meet the minimum requirement mentioned. It is to be noted that the presence of acrylamide in the monomer solution might enhance the solubility of other monomers as compared to water only. In general, the solubility of the water-soluble monomers in water at room temperature should be at least 50 g/l, preferably at least 100 g/l.

Basically, the kind and amount of water-soluble, monoethylenically unsaturated comonomers to be used besides acrylamide is not limited and depends on the desired properties and the desired use of the aqueous solutions of polyacrylamides to be manufactured.

Neutral Comonomers

In one embodiment of the invention, comonomers may be selected from uncharged water-soluble, monoethylenically unsaturated monomers. Examples comprise methacrylamide, N-methyl(meth)acrylamide, N,N'-dimethyl(meth)acrylamide, N-methylol(meth)acrylamide or N-vinylpyrrolidone. Further examples have been mentioned in WO 2015/158517 A1 page 7, lines 9 to 14.

Anionic Comonomers

In a further embodiment of the invention, comonomers may be selected from water-soluble, monoethylenically unsaturated monomers comprising at least one acidic group, or salts thereof. The acidic groups are preferably selected from the group of —COOH, —$SO_3H$ and —$PO_3H_2$ or salts thereof. Preference is given to monomers comprising COOH groups and/or —$SO_3H$ groups or salts thereof. Suitable counterions include especially alkali metal ions such as $Li^+$, $Na^+$ or $K^+$, and also ammonium ions such as $NH_4^+$ or ammonium ions having organic radicals. Examples of ammonium ions having organic radicals include [NH$(CH_3)_3]^+$, [$NH_2(CH_3)_2]^+$, [$NH_3(CH_3)]^+$, [$NH(C_2H_5)_3]^+$, [$NH_2(C_2H_5)_2]^+$, [$NH_3(C_2H_5)]^+$, [$NH_3(CH_2CH_2OH)]^+$, [$H_3N$—$CH_2CH_2$—$NH_3]^{2+}$ or [$H(H_3C)_2N$—$CH_2CH_2CH_2NH_3]^{2+}$. Furthermore, $Ca^{2+}$ ions may be suitable.

Examples of monomers comprising —COOH groups include acrylic acid, methacrylic acid, crotonic acid, itaconic acid, maleic acid or fumaric acid or salts thereof. Preference is given to acrylic acid or salts thereof.

Examples of monomers comprising —$SO_3H$ groups or salts thereof include vinylsulfonic acid, allylsulfonic acid, 2-acrylamido-2-methylpropanesulfonic acid (ATBS), 2-methacrylamido-2-methylpropanesulfonic acid, 2-acrylamidobutanesulfonic acid, 3-acrylamido-3-methylbutanesulfonic acid or 2-acrylamido-2,4,4-trimethylpentanesulfonic acid. Preference is given to 2-acrylamido-2-methylpropanesulfonic acid (ATBS) or salts thereof.

Examples of monomers comprising —$PO_3H_2$ groups or salts thereof include vinylphosphonic acid, allylphosphonic acid, N-(meth)acrylamidoalkylphosphonic acids or (meth)acryloyloxyalkylphosphonic acids, preferably vinylphosphonic acid.

Preferred monomers comprising acidic groups comprise acrylic acid and/or ATBS or salts thereof.

Cationic Comonomers

In a further embodiment of the invention, comonomers may be selected from water-soluble, monoethylenically unsaturated monomers comprising cationic groups. Suitable cationic monomers include especially monomers having ammonium groups, especially ammonium derivatives of N-(ω)-aminoalkyl)(meth)acrylamides or ω-aminoalkyl (meth)acrylates such as 2-trimethylammonioethyl acrylate chloride 

(DMA3Q). Further examples have been mentioned in WO 2015/158517 A1 page 8, lines 15 to 37. Preference is given to DMA3Q.

Associative Comonomers

In a further embodiment of the invention, comonomers may be selected from associative monomers.

Associative monomers impart hydrophobically associating properties to polyacrylamides. Associative monomers to be used in the context of this invention are water-soluble, monoethylenically unsaturated monomers having at least one hydrophilic group and at least one, preferably terminal, hydrophobic group. Examples of associative monomers have been described for example in WO 2010/133527, WO 2012/069478, WO 2015/086468 or WO 2015/158517.

"Hydrophobically associating copolymers" are understood by a person skilled in the art to mean water-soluble copolymers which, as well as hydrophilic units (in a sufficient amount to assure water solubility), have hydrophobic groups in lateral or terminal positions. In aqueous solution, the hydrophobic groups can associate with one another. Because of this associative interaction, there is an increase in the viscosity of the aqueous polymer solution compared to a polymer of the same kind that merely does not have any associative groups.

Examples of suitable associative monomers comprise monomers having the general formula $H_2C=C(R^1)-R^2-R^3$ (I) wherein $R^1$ is H or methyl, $R^2$ is a linking hydrophilic group and $R^3$ is a terminal hydrophobic group. Further examples comprise having the general formula $H_2C=C(R^1)-R^2-R^3-R^4$ (II) wherein $R^1$, $R^2$ and $R^3$ are each as defined above, and $R^4$ is a hydrophilic group.

The linking hydrophilic $R^2$ group may be a group comprising ethylene oxide units, for example a group comprising 5 to 80 ethylene oxide units, which is joined to the $H_2C=C(R^1)-$ group in a suitable manner, for example by means of a single bond or of a suitable linking group. In another embodiment, the hydrophilic linking group $R^2$ may be a group comprising quaternary ammonium groups.

In one embodiment, the associative monomers are monomers of the general formula $H_2C=C(R^1)-O-(CH_2CH_2O)_k-R^{3a}$ (III) or $H_2C=C(R^5)-(C=O)-O-(CH_2CH_2O)_k-R^{3a}$ (IV), wherein $R^1$ has the meaning defined above and k is a number from 10 to 80, for example, 20 to 40. $R^{3a}$ is an aliphatic and/or aromatic, straight-chain or branched hydrocarbyl radical having 8 to 40 carbon atoms, preferably 12 to 32 carbon atoms.

Examples of such groups include n-octyl, n-decyl, n-dodecyl, n-tetradecyl, n-hexadecyl or n-octadecyl groups. In a further embodiment, the groups are aromatic groups, especially substituted phenyl radicals, especially distyrylphenyl groups and/or tristyrylphenyl groups.

In another embodiment, the associative monomers are monomers of the general formula $H_2C=C(R^1)-O-(CH_2)_n-O-(CH_2CH_2O)_x-(CH_2-CH(R^6)O)_y-(CH_2CH_2O)_zH$ (V), wherein $R^1$ is defined as above and the $R^5$ radicals are each independently selected from hydrocarbyl radicals comprising at least 2 carbon atoms, preferably from ethyl or propyl groups. In formula (V) n is a natural number from 2 to 6, for example 4, x is a number from 10 to 50, preferably from 12 to 40, and for example, from 20 to 30 and y is a number from 5 to 30, preferably 8 to 25. In formula (V), z is a number from 0 to 5, for example 1 to 4, i.e. the terminal block of ethylene oxide units is thus merely optionally present. In an embodiment of the invention, it is possible to use at least two monomers (V), wherein the $R^1$ and $R^6$ radicals and indices n, x and y are each the same, but in one of the monomers z=0 while z>0 in the other, preferably 1 to 4.

In another embodiment, the associative monomers are cationic monomers. Examples of cationic associative monomers have been disclosed in WO 2015/158517 A1, page 11, line 20 to page 12, lines 14 to 42. In one embodiment, the cationic monomers having the general formula $H_2C=C(R^1)-C(=O)O-(CH_2)_k-N^+(CH_3)(CH_3)(R^6)$ $X^-$ (VI) or $H_2C=C(R^1)-C(=O)N(R^1)-(CH_2)_k-N^+(CH_3)(CH_3)(R^6)$ $X^-$ (VII) may be used, wherein $R^1$ has the meaning as defined above, k is 2 or 3, $R^6$ is a hydrocarbyl group, preferably an aliphatic hydrocarbyl group, having 8 to 18 carbon atoms, and $X^-$ is a negatively charged counterion, preferably $Cl^-$ and/or $Br^-$.

Further Comonomers

Besides water-soluble monoethylenically unsaturated monomers, also water-soluble, ethylenically unsaturated monomers having more than one ethylenic group may be used. Monomers of this kind can be used in special cases in order to achieve easy crosslinking of the acrylamide polymers. The amount thereof should generally not exceed 2% by weight, preferably 1% by weight and especially 0.5% by weight, based on the sum total of all the monomers. More preferably, the monomers to be used in the present invention are only monoethylenically unsaturated monomers.

Composition of Polyacrylamides

The specific composition of the polyacrylamides to be manufactured according the process of the present invention may be selected according to the desired use of the polyacrylamides.

Preferred polyacrylamides comprise, besides at least 10% by weight of acrylamide, at least one water-soluble, monoethylenically unsaturated comonomer, preferably at least one comonomer selected from the group of acrylic acid or salts thereof, ATBS or salts thereof, associative monomers, in particular those of formula (V) or DMA3Q, more preferably at least one comonomer selected from acrylic acid or salts thereof, ATBS or salts thereof, associative monomers, in particular those of formula (V).

In one embodiment, the polyacrylamides comprise 20% to 90% by weight of acrylamide and 10% to 80% by weight of acrylic acid and/or salts thereof, wherein the amounts of the monomers relate to the total of all monomers in the polymer.

In one embodiment, the polyacrylamides comprise 20% to 40% by weight of acrylamide and 60% to 80% by weight of acrylic acid and/or salts thereof.

In one embodiment, the polyacrylamides comprise 55% to 75% by weight of acrylamide and 25% to 45% by weight of acrylic acid and/or salts thereof.

In one embodiment, the polyacrylamides comprise 45% to 75% by weight of acrylamide and 25% to 55% by weight of ATBS and/or salts thereof.

In one embodiment, the polyacrylamides comprise 30% to 80% by weight of acrylamide, 10% to 40% by weight of acrylic acid and/or salts thereof, and 10% to 40% by weight of ATBS and/or salts thereof.

In one embodiment, the polyacrylamides comprise 45% to 75% by weight of acrylamide, 0.1 to 5%, preferably 0.1 to 2% by weight of at least one associative monomer of the general formulas (I) or (II) mentioned above and 10 to 54.9% by weight of acrylic acid and/or ATBS and/or salts thereof. Preferably, the associative monomer(s) have the general formula (V) including the preferred embodiments mentioned above.

In one embodiment, the polyacrylamides comprise 60% to 75% by weight of acrylamide, 0.1 to 5%, preferably 0.1 to 2% by weight of at least one associative monomer of the general formula (V) mentioned above, including the preferred embodiments, and 20 to 39.9% by weight of acrylic acid or salts thereof.

In one embodiment, the polyacrylamides comprise 45% to 55% by weight of acrylamide, 0.1 to 5%, preferably 0.1 to 2% by weight of at least one associative monomer of the general formula (V) mentioned above, including the preferred embodiments, and 40 to 54.9% by weight of acrylic acid or salts thereof.

In one embodiment, the polyacrylamides comprise 60% to 99% by weight of acrylamide and 1% to 40% by weight of DMA3Q.

In one embodiment, the polyacrylamides comprise 10% to 50% by weight of acrylamide and 50% to 90% by weight of DMA3Q.

In one embodiment, the polyacrylamides comprise 90 to 99.5% by weight of acrylamide, 0.5 to 2% by weight of at least one associative monomer, and 0% to 9.5% by weight of and anionic monomer, for example ATBS or a cationic monomer, for example DM3AQ. Preferably, the associative monomer(s) have the general formula (V) including the preferred embodiments mentioned above.

In all embodiments mentioned above, the amount of the monomers relates to the total of all monomers in the polyacrylamide. Further water-soluble, monoethylenically unsaturated monomers may be present besides those specifically mentioned, however, the embodiments each include also one embodiment in which besides the monomers specifically mentioned no further monomers are present, i.e. in these embodiments the total amount of the monomers specifically mentioned is 100% by weight.

The weight average molecular weight $M_w$ of the polyacrylamides to be manufactured is selected by the skilled artisan according to the intended use of the polyacrylamides.

For many applications high molecular weights are desirable. A high molecular weight corresponds to a high intrinsic viscosity (IV) of the polyacrylamides. In one embodiment of the invention, the intrinsic viscosity may be at least 15 deciliter/gram (dL/g). In one embodiment of the invention, the intrinsic viscosity is from 30 to 45 dl/g.

The numbers mentioned relate to the measurement with an automatic Lauda iVisc® LMV830 equipped with an Ubbelohde capillary tube and automatic injection. For the measurements an aqueous solution of the polymers to be analyzed was prepared having a concentration of 250 ppm. The pH was adjusted at 7 by means of a buffer and the solution comprised additionally 1 mol/l of NaCl. Further four dilutions were done automatically. The viscosity at five different concentrations was measured at 25° C. with. The IV value [dL/g] was determined in usual manner by extrapolating the viscosities to infinite dilution. The error range is about ±2 dL/g.

Locations A and B

The process according to the present invention is carried out at least at two different locations A and B and includes transporting an aqueous polyacrylamide concentrate from location A to location B.

At location A, an aqueous monomer solution comprising acrylamide is polymerized in a polymerization unit (step [1]) thereby obtaining an aqueous polyacrylamide gel hold in the polymerization unit.

The aqueous monomer solution may also be manufactured at location A but it is also possible to manufacture the aqueous monomer solution or a more concentrated aqueous monomer premix at another location and to ship them to location A for further processing. In one embodiment of the invention, a step of manufacturing acrylamide by hydrolysis of acrylonitrile by means of a biocatalyst (hereinafter referred to as step [0]) is part of the process. Said step [0] may also be carried out at location A or at another location.

After polymerization, the aqueous polyacrylamide gel is removed from the polymerization unit (step [2]) and comminuted and mixed with an aqueous liquid, thereby obtaining an aqueous polyacrylamide concentrate (step [3]). Such steps are also carried out at location A.

In step [5], the aqueous polyacrylamide concentrate is transported from location A to a different location B using a suitable transport unit.

Location B preferably may be a site-of-use, i.e. a location at which the aqueous polyacrylamide concentrates are used or at least a location close to such a site-of-use. At location B, the aqueous polyacrylamide concentrate is removed from the transport unit. In one embodiment, the aqueous concentrate may be used as such. Alternatively, the concentrate may be further diluted with further aqueous liquid at location B and/or formulated with further components.

Subterranean, oil-bearing reservoirs typically extend over a large area. Length and width of a subterranean, oil-bearing reservoir may be up to several hundred kilometers. For producing oil from such subterranean, oil-bearing reservoirs typically many oil wells, injection wells as well as production wells, are distributed over the subterranean reservoir. Similarly, regions comprising valuable minerals such as ores or oil sands may also extend over a large area and individual mines may be distributed in the mining area.

In one embodiment, location B may be at an oil and/or gas well to be treated with polyacrylamides or close to such an oil and/or gas well. Examples comprise oil wells which into which aqueous polyacrylamide solutions are injected in course of enhanced oil operations, production wells whose productivity is enhanced by injection of fracturing fluids comprising polyacrylamides as friction reducers, or wells which are drilled and aqueous polyacrylamide solutions are used for making the drilling fluid.

In the field of mining, location B may be a location at or close to a tailings ponds in which mineral tailings are dewatered using aqueous polyacrylamide solutions. In one embodiment of the invention location B may be a location for the treatment of red mud, a by-product of the Bayer process for manufacturing aluminium.

In other embodiments, location B may be at a paper production site, at sewage works, at seawater desalination plants or at sites for manufacturing agricultural formulations.

Location A is apart from location B.

In one embodiment, location A may be a fixed chemical plant apart from location(s) B.

In a preferred embodiment of the invention, location A is a local hub which provides a plurality of different locations B with aqueous polyacrylamide concentrates. In an embodiment, the local hub is located at a central point having good transport connections in order to ensure easy and economic supply with raw materials.

In one embodiment, location A may be at a central point over a subterranean, oil-bearing formation or a central point in between different subterranean, oil-bearing formations and from location A a plurality of oil wells to be treated is provided with aqueous polyacrylamide concentrates for further processing.

In another embodiment, location A is at a central point in a mining area and from location A a plurality of tailing ponds is provided with aqueous polyacrylamide concentrates for further processing.

The distance between location A and the location(s) B is not specifically limited. Generally, in order to limit the costs of transporting the aqueous polyacrylamide concentrates, location A should be located close to the locations B or at least not too far apart from the locations B. Having said that, the abovementioned dimensions of mining areas or subterranean, oil-bearing formations should be kept in mind. So, even when location A is a local hub as outlined above, the local hub A and the locations B may be apart from each other up a few hundred kilometers.

By the way of example, the distance between location A and location(s) B may range from 1 to 3000 km, in particular from 10 km to 3000 km, for example from 10 to 1500 km or from 20 km to 500 km or from 30 to 300 km.

Modular Plant

While it is possible to perform some steps of the process in fixed plants, it is preferred to perform the entire process of manufacturing aqueous polyacrylamide concentrates according to the present invention in a modular manner using relocatable units.

Each relocatable unit bundles certain functions of the plant. Examples of such relocatable units comprise units for storing and optionally cooling the monomers and other raw materials, hydrolyzing acrylonitrile, mixing monomers, polymerization and gel dissolution. Details will be provided below. For carrying out the process according to the present invention individual units are connected with each other in a suitable manner thereby obtaining a production line.

"Relocatable unit" means that the unit is transportable basically as a whole and that is it not necessary to disassemble the entire unit into individual parts for transport. Transport may happen on trucks, railcars or ships.

In one embodiment, such modular, relocatable units are containerized units which may be transported in the same manner as closed intermodal containers for example on trucks, railcars or ships. Intermodal containers are large standardized (according to ISO 668) shipping containers, in particular designed and built for intermodal freight transport. Such containers are also known as ISO containers. Such ISO containers may have external dimensions of a height of ~2.59 m, a width of ~2.44 m and a length of ~6.05 m. Larger ISO containers have external dimensions of a height of ~2.59 m, a width of ~2.44 m and a length of ~12.19 m. There are of course other standards, for example units having modular dimensions of 12 feet (~3.66 m)×12 feet (~3.66 m)×12 feet (~3.66 m) or multiples thereof, e.g. 12 (~3.66 m)×12 (~3.66 m)×48 (~14,63 m).

In another embodiment, the relocatable units may be fixed on trucks or on trailers. With other words, for such relocatable units not a container or something similar is deployed at location A or location B, but the entire truck or the trailer including the unit in its loading spaces is deployed. The trucks or trailers advantageously also function as platform for the units on the ground. Also, two or more different units may be mounted together on a truck or trailer.

The relocatable units are combined at the locations A and B, thereby obtaining modular production plants for performing the process according to the present invention.

Such a modular construction using relocatable units provides the advantage, that the plants at location A and at location B may be easily relocated if polyacrylamides are no longer needed at one location but at another location.

By the way of example, in enhanced oil recovery aqueous polyacrylamide solutions are injected into a subterranean, oil-bearing formations through one or more than one injection wells sunk into the formation. Such an injection may continue for months or even years. However, at some point in time no further oil production is possible. The modular plant may then be easily relocated to another location, for example to another oilfield.

Provision of the Aqueous Monomer Solution

In course of step [1] an aqueous monomer solution comprising at least water, acrylamide and optionally further water-soluble, monoethylenically unsaturated monomers is polymerized at location A.

For carrying out step [1] said aqueous monomer solution is provided to location A. In one embodiment of the invention, the monomer solution may be manufactured at location A. In another embodiment, the aqueous monomer solution or a more concentrated aqueous monomer premix may be manufactured at another location and transported to location A.

The process may optionally comprise the step of manufacturing acrylamide from acrylonitrile using a biocatalyst (hereinafter step [0]) and also optionally manufacturing ammonium acrylate for use as comonomer acrylamide from acrylonitrile using a biocatalyst. Both steps may also be carried out at location A or—in case the aqueous monomer solution is manufactured at another location—at such other location.

Provision of Acrylamide

Acrylamide may be synthesized by partial hydrolysis of acrylonitrile using suitable catalysts. It is known in the art to use copper catalysts or other metal containing catalysts and it is also known to use biocatalysts capable of converting acrylonitrile to acrylamide. Pure acrylamide is a solid, however, typically acrylamide—whether made by bio catalysis or copper catalysis—is provided as aqueous solution, for example as aqueous solution comprising about 50% by wt. of acrylamide.

Acrylamide obtained by means of biocatalysts (often referred to as "bio acrylamide") can be distinguished from acrylamide obtained by means of copper catalysts or other metal containing catalysts because the latter still comprises at least traces of copper or other metals. Acrylamide obtained by means of biocatalysts may still comprise traces of the biocatalyst.

For the process according to the present invention, preferably an aqueous acrylamide solution is used which has been obtained by hydrolyzing acrylonitrile in water in presence of a biocatalyst capable of converting acrylonitrile to acrylamide. As will be detailed below, using biocatalysts for hydrolyzing acrylonitrile has significant advantages for the present invention, in particular for transporting the aqueous polyacrylamide gel.

In one embodiment of the invention, aqueous solutions of bio acrylamide for use in the process according to the present invention may be manufactured at another location, for example in a fixed chemical plant, and shipped either to location A or to another location for manufacturing an aqueous monomer solution.

In a preferred embodiment of the present invention the manufacture of bio acrylamide is performed at location A (hereinafter designated as process step [0]).

Manufacturing bio acrylamide at location A saves significant transport costs. Acrylonitrile is a liquid and may be transported as pure compound to location A. The molecular weight of acrylamide is ~34% higher than that of acrylonitrile and acrylamide is typically provided as ~50% aqueous solution. So, for a 50% aqueous solution of acrylamide the mass to be transported is about 2.5-fold as much as compared to transporting pure acrylonitrile. Transporting pure, solid acrylamide means transporting only ~34% more mass as compared to transporting pure acrylonitrile, however, additional equipment for handling and dissolving the solid acrylamide is necessary at location A.

Step [0]—Hydrolysis of Acrylonitrile

As already outlined above, step [0] is only optional for the process according to the present invention, however, in a preferred embodiment of the invention, the process according to the invention includes step [0]. In course of step [0] acrylonitrile is hydrolyzed in water in presence of a biocatalyst capable of converting acrylonitrile to acrylamide thereby obtaining an aqueous acrylamide solution. Step [0] may be performed at location A.

Provision of Acrylonitrile

Acrylonitrile for step [0] may be stored in one or more than one relocatable storage units. The storage unit comprises a storage vessel. The volume of the storage vessel is not specifically limited and may range from 50 $m^3$ to 150 $m^3$, for example it may be about 100 $m^3$. Preferably, the storage vessel should be double walled and should be horizontal. Such a construction avoids installing a pit for the collection of any leakage thereby ensuring an easier and quicker relocation of the storage unit. Double-walled vessels may be placed on every good bearing soil. The storage unit furthermore comprises means for charging and discharging the vessel, means for controlling the pressure in the vessel, for example a valve for settling low-pressure or overpressure, and means for controlling the temperature of the acrylonitrile which preferably should not exceed 25° C. It furthermore may comprise means for measurement and control to the extent necessary.

Examples of relocatable storage units comprise relocatable cuboid, storage tanks, preferably double-walled tanks. Further, any considerable form, shape and size of container is suitable and applicable for the storage and/or provision of acrylonitrile in the sense of the present invention. Particularly, standard iso-tanks are applicable for the storage and/or provision of acrylonitrile.

Other examples comprise tank containers having a cuboid frame, preferably a frame according to the ISO 668 norm mentioned above and one or more storage vessels mounted into the frame. Such normed tank containers may be stacked and transported on trucks, railcars or ships in the same manner closed intermodal containers.

Basically, temperature control may be performed by any kind of temperature controlling unit. Temperature control may require—depending on the climatic conditions prevailing at location A—cooling or heating the contents of the storage units. Regarding the monomers, temperature control typically means cooling, because it should be avoided that the monomers become too hot. In one embodiment, an internal heat exchanger may be used for cooling or heating, i.e. a heat exchanger mounted inside of the storage vessel. The coolant is provided to the heat exchanger by a suitable cooling or heating unit mounted outside of the storage vessel.

In another embodiment of the invention, for temperature control an external temperature control cycle, for example a cooling cycle is used, which comprises a pump which pumps the monomer from the storage vessel through a heat exchanger and back into the storage vessel.

The temperature control cycle may be a separate, relocatable temperature control unit comprising pump and heat exchanger and which is connected with the storage vessel by pipes or flexible tubes.

In another embodiment, the temperature control cycle may be integrated into relocatable storage unit. It may—for example—be located at one end of the unit besides the storage vessel.

FIG. 1 schematically represents one embodiment of a monomer storage unit comprising an integrated temperature control cycle. It comprises a frame (1). The frame may in particular be a cuboid frame preferably having standardized container dimensions which eases transport. The relocatable storage unit furthermore comprises a double-walled vessel mounted into the frame comprising an outer wall (2) and an inner wall (3). In other embodiments, there is no such frame (1) but the storage vessel is self-supporting. The storage vessel is filled with acrylonitrile. The storage unit furthermore comprises an external temperature control cycle comprising at least a pump and a temperature control unit. For cooling, acrylonitrile is circulated by means of a pump (4) from the storage vessel to the temperature control unit (5) and back into the storage vessel. The amount of acrylonitrile to be circulated in the temperature control cycle in order to control the temperature at an acceptable level, for example below 25° C. depends in particular on the outside temperature and the internal temperature envisaged. In one embodiment, 10% to 100% of the volume of acrylonitrile in the vessel may be circulated per hour.

FIG. 2 represents schematically another embodiment of a monomer storage unit. It comprises a cuboic, preferably double-walled storage vessel (6). If necessary, the storage vessel (6) is connected with an external, relocatable temperature control unit (7).

Acrylonitrile may be provided to location A by road tankers, ISOtanks or rail cars and pumped into the relocatable storage vessel(s).

The acrylonitrile may be removed from the relocatable storage vessel through a bottom valve by means of gravity or it may be pumped, for example from the upper side using a suitable pump.

Biocatalysts

As biocatalyst for performing step [0], nitrile hydratase enzymes can be used, which are capable of catalyzing the hydrolysis of acrylonitrile to acrylamide. Typically, nitrile hydratase enzymes can be produced by a variety of microorganisms, for instance microorganisms of the genus *Bacillus, Bacteridium, Micrococcus, Brevibacterium, Corynebacterium, Pseudomonas, Acinetobacter, Xanthobacter, Streptomyces, Rhizobium, Klebsiella, Enterobacter, Escherichia Coli, Erwinia, Aeromonas, Citrobacter, Achromobacter, Agrobacterium, Pseudonocardia* and *Rhodococcus*. WO 2005/054456 discloses the synthesis of nitrile hydratase within microorganisms and therein it is described that various strains of *Rhodococcus rhodochrous* species have been found to very effectively produce nitrile hydratase enzymes, in particular *Rhodococcus rhodochrous* NCI MB 41164. Such microorganisms, suitable as biocatalyst for the enzymatic conversion of acrylonitrile to acrylamide, which are known for a person skilled in the art, are able to be applied in a relocatable bioconversion unit according to the present invention. Additionally, the specific methods of culturing (or cultivation, or fermentation) and/or storing the microorganism as well as the respective sequences of polynucleotides which are encoding the enzyme, particularly the nitrile hydratase, are known in the art, e.g. WO 2005/054456, WO 2016/050816, and are applicable in context of the present invention. Within the present invention nitrile hydratase and amidase producing microorganisms may be used for converting a nitrile compound into the corresponding amide compound as it is described for example in WO 2016/050816.

The terms "nitrile hydratase (NHase) producing microorganism" or "microorganism" or "biocatalysts" or the like, have the meaning to be able to produce (i.e. they encode and express) the enzyme nitrile hydratase (also referred to as, e.g., NHase) either per se (naturally) or they have been genetically modified respectively. Microorganisms which have been "genetically modified" means that these microorganisms have been manipulated such that they have acquired the capability to express the required enzyme NHase, e.g. by way of incorporation of a naturally and/or modified nitrile hydratase gene or gene cluster or the like. Produced products of the microorganisms that can be used in the context of the present invention are also contemplated, e.g. suspensions obtained by partial or complete cell disruption of the microorganisms.

The terms "nitrile hydratase (NHase) producing microorganism" or "microorganism" or "biocatalysts" or the like, include the cells and/or the processed product thereof as such, and/or suspensions containing such microorganisms and/or processed products.

It is also envisaged that the microorganisms and/or processed products thereof are further treated before they are employed in the embodiments of the present invention. "Further treated" thereby includes for example washing steps and/or steps to concentrate the microorganism etc. It is also envisaged that the microorganisms that are employed in the embodiments of the present invention have been pre-treated by a for example drying step. Also known methods for cultivating of the microorganisms and how to optimize the cultivation conditions via for example addition of urea or cobalt are described in WO 2005/054456 and are compassed by the embodiments of the present invention. Advantageously, the microorganism can be grown in a medium containing acetonitrile or acrylonitrile as an inducer of the nitrile hydratase.

Preferably, the biocatalyst for converting acrylonitrile to acrylamide may be obtained from culturing the microorganism in a suitable growth medium. The growth medium, also called fermentation (culture) medium, fermentation broth, fermentation mixture, or the like, may comprise typical components like sugars, polysaccharides, which are for example described in WO 2005/054489 and which are suitable to be used for the culturing the microorganism of the present inventions to obtain the biocatalyst. For storage of the microorganism, the fermentation broth preferably is removed in order to prevent putrefaction, which could result in a reduction of nitrile hydratase activity. The methods of storage described in WO 2005/054489 may be applied according to the present invention ensuring sufficient biocatalyst stability during storage. Preferably, the storage does not influence biocatalytic activity or does not lead to a reduction in biocatalytic activity. The biocatalyst may be stored in presence of the fermentations broth components. Preferred in the sense of the present invention is that the biocatalyst may be stored in form of a frozen suspension and may be thawed before use. Further, the biocatalyst may be stored in dried form using freeze-drying, spray drying, heat drying, vacuum drying, fluidized bed drying and/or spray granulation, wherein spray drying and freeze drying are preferred.

Biocatalyst Make-Up

The biocatalysts that are used according to the present invention in a relocatable plant can for example be cultured under any conditions suitable for the purpose in accordance with any of the known methods, for instance as described in the mentioned prior art of this specification. The biocatalyst may be used as a whole cell catalyst for the generation of amide from nitrile. The biocatalyst may be (partly) immobilized for instance entrapped in a gel or it may be used for example as a free cell suspension. For immobilization well known standard methods can be applied like for example entrapment cross linkage such as glutaraldehyde-polyethyleneimine (GA-PEI) crosslinking, cross linking to a matrix and/or carrier binding etc., including variations and/or combinations of the aforementioned methods. Alternatively, the nitrile hydratase enzyme may be extracted and for instance may be used directly in the process for preparing the amide. When using inactivated or partly inactivated cells, such cells may be inactivated by thermal or chemical treatment.

In a preferred embodiment, the microorganisms are whole cells. The whole cells may be pre-treated by a drying step. Suitable drying methods and/or drying conditions are disclosed e.g. in WO 2016/050816 and WO 2016/050861 and the know art can be applied in the context of the present invention for the use in a relocatable bioconversion unit.

The microorganisms that are employed in the context of the present invention are in a preferred embodiment used in an aqueous suspension and in a more preferred embodiment are free whole cells in an aqueous suspension. The term "aqueous suspension" thereby includes all kinds of liquids, such as buffers or culture medium that are suitable to keep microorganisms in suspension. Such liquids are well-known to the skilled person and include for example storage buffers at suitable pH such as storage buffers which are used to deposit microorganisms, TRIS-based buffers, saline based buffers, water in all quality grades such as distilled water, pure water, tap water, or sea water, culture medium, growing medium, nutrient solutions, or fermentation broths, for example the fermentation broth that was used to culture the microorganisms. During storage for example the aqueous suspension is frozen and thawed before use, in particular without loss in activity.

The biocatalyst may be provided as powder or as aqueous suspension to location A. If provided as powder it is frequently advisable to prepare an aqueous suspension before adding the catalyst into the bioconversion unit. In an embodiment, the biocatalyst suspension may be conducted by suspending the biocatalyst powder in water in a vessel comprising at least a mixing device, for example a stirrer, one or more inlets for water, the biocatalyst and optionally further additives and one outlet for the biocatalyst suspension. The volume of the vessel may be for example from 0.1 $m^3$ to 1 $m^3$. The concentration of the biocatalyst in the aqueous biocatalyst suspension may be for example from 1% to 30% by wt., for example from 10 to 20% by wt. relating to the total of all components of the aqueous suspension.

A biocatalyst suspension may be added directly to the bioconversion unit. In another embodiment a concentrated suspension may be diluted before adding it to the bioconversion unit.

Bioconversion

The hydrolysis of acrylonitrile to acrylamide by means of a biocatalyst is performed in a suitable bioconversion unit, preferably a relocatable bioconversion unit.

Particularly, the bioconversion is performed by contacting a mixture comprising water and acrylonitrile with the biocatalyst. The term "contacting" is not specifically limited and includes for example bringing into contact with, admixing, stirring, shaking, pouring into, flowing into, or incorporating into. It is thus only decisive that the mentioned ingredients come into contact with each other no matter how that contact is achieved.

Therefore, in one embodiment of the present invention step [0] comprises the following steps:
(a) Adding the following components (i) to (iii) to a bioconversion unit to obtain a composition for bioconversion:
  (i) a biocatalyst capable of converting acrylonitrile to acrylamide;
  (ii) acrylonitrile;
  (iii) aqueous medium; and
(b) performing a bioconversion on the composition obtained in step (a).

The bioconversion can for example be conducted under any conditions suitable for the purpose in accordance with any of the known methods, for instance as described in the mentioned prior art of this specification like e.g. WO 2016/050817, WO 2016/050819, WO 2017/055518.

The conversion of acrylonitrile to the acrylamide may be carried out by any of a batch process and a continuous process, and the conversion may be carried out by selecting its reaction system from reaction systems such as suspended bed, a fixed bed, a fluidized bed and the like or by combining different reaction systems according to the form of the catalyst. Particularly, the method of the present invention may be carried out using a semi-batch process. In particular, the term "semi-batch process" as used herein may comprise that an aqueous acrylamide solution is produced in a discontinuous manner.

According to a non-limiting example for carrying out such a semi-batch process water, a certain amount of acrylonitrile and the biocatalyst are placed in the bioconversion unit. Further acrylonitrile is then added during the bioconversion until a desired content of acrylamide of the composition is reached. After such desired content of acrylamide is reached, the obtained composition is for example partly or entirely recovered from the reactor, before new reactants are placed therein. In particular, in any one of the methods of the present invention the acrylonitrile may be fed such that the content of acrylonitrile during step (b) is maintained substantially constant at a predetermined value. In general, in any one of the methods of the present invention the acrylonitrile content and/or the acrylamide content during step (b) may be monitored. Methods of monitoring the acrylonitrile contents are not limited and include Fourier Transform Infrared Spectroscopy (FTIR). In another embodiment, the heat-balance of the reaction may be used for monitoring the process. This means that monitoring via heat-balance method takes place by measuring the heat energy of the system during bioconversion and by calculating the loss of heat energy during the reaction in order to monitor the process.

Although the conversion of acrylonitrile to the acrylamide may preferably be carried out at atmospheric pressure, it may be carried out under pressure in order to increase solubility of acrylonitrile in the aqueous medium. Because biocatalysts are temperature sensitive and the hydrolysis is an exothermic reaction temperature control is important. The reaction temperature is not specifically restricted provided that it is not lower than the ice point of the aqueous medium. However, it is desirable to carry out the conversion at a temperature of usually 0 to 50° C., preferably 10 to 40° C., more preferably 15 to 30° C. Further suitable condition for the bioconversion according to the present invention are for example described in WO 2017/055518 and are preferably applicable for the method in a relocatable bioconversion unit.

Although the amount of biocatalyst may vary depending on the type of biocatalyst to be used, it is preferred that the activity of the biocatalyst, which is introduced to the reactor, preferably the relocatable bioconversion unit, is in the range of about 5 to 500 U per mg of dried cells of microorganism. Methods for determining the ability of a given biocatalyst (e.g. microorganism or enzyme) for catalyzing the conversion of acrylonitrile to acrylamide are known in the art. As an example, in context with the present invention, activity of a given biocatalyst to act as a nitrile hydratase in the sense of the present invention may be determined as follows: First reacting 100 µl of a cell suspension, cell lysate, dissolved enzyme powder or any other preparation containing the supposed nitrile hydratase with 875 µl of a 50 mM potassium phosphate buffer and 25 µl of acrylonitrile at 25° C. on an Eppendorf tube shaker at 1,000 rpm for 10 minutes. After 10 minutes of reaction time, samples may be drawn and immediately quenched by adding the same volume of 1.4% hydrochloric acid. After mixing of the sample, cells may be removed by centrifugation for 1 minute at 10,000 rpm and the amount of acrylamide formed is determined by analyzing the clear supernatant by HPLC. For affirmation of an enzyme to be a nitrile hydratase in context with the present invention, the concentration of acrylamide shall particularly be between 0.25 and 1.25 mmol/l—if necessary, the sample has to be diluted accordingly and the conversion has to be repeated. The enzyme activity may then be deduced from the concentration of acrylamide by dividing the acrylamide concentration derived from HPLC analysis by the reaction time, which has been 10 minutes and by multiplying this value with the dilution factor between HPLC sample and original sample. Activities >5 U/mg dry cell weight, preferably >25 U/mg dry cell weight, more preferably >50 U/mg dry cell weight, most preferably >100 U/mg dry cell weight indicate the presence of a functionally expressed nitrile hydratase and are considered as nitrile hydratase in context with the present invention.

It is preferred, that the concentration of acrylonitrile during the bioconversion should not exceed 6% by wt. and may for example be in the range from 0.1% by wt. to 6% by wt., preferably from 0.2% by wt. to 5% by wt., more preferably from 0.3% by wt. to 4% by wt., even more preferably from 0.5% by wt. to 3% by wt., still more preferably from 0.8% by wt. to 2% by wt. and most preferably from 1% by wt. to 1.5% by wt., relating to the total of all components of the aqueous mixture. It is possible that the concentration may vary over time during the bioconversion reaction. In order to obtain more concentrated solutions of acrylamide the total amount of acrylonitrile should not be added all at once but it should be added stepwise or even continuously keeping the abovementioned concentration limits in mind. The disclosure of WO 2016/050818 teaches a method of additional dosing of acrylonitrile, which is suitable to be used and applied in the present invention.

The concentration of acrylamide in the obtained solution is in the range from 10% to 80%, preferably in the range from 20% to 70%, more preferably in the range from 30% to 65%, even more preferably in the range from 40% to 60%, most preferably in the range from 45% to 55% by weight of acrylamide monomers. The reaction should be carried out in such a manner that the final concentration of acrylonitrile in the final acrylamide solution obtained does not exceed 0.1% by weight relating to the total of all components of the aqueous solution. Typical reaction times may be from 2 to 20 h, in particular 4 h to 12 h, for example 6 h to 10 h. After completion of the addition of acrylonitrile, the reactor contents is allowed to further circulate for some time to complete the reaction, for example for 1 hour to 3 hours. The remaining contents of acrylonitrile should preferably be less than 100 ppm ACN.

Suitable reactors for performing the bioconversion are known to the skilled artisan. Examples comprise vessels of any shape, for example cylindrical or spherical vessels, or tube reactors. In one embodiment, the continuous tank reactor as disclosed in WO 2016/006556 A1 may be used for bioconversion. Further suitable reactors for the bioconversion according to the present invention are for example described in US20040175809, EP2336346, EP2518154, JP2014176344, JP2015057968 and such reactors are preferably applicable for the process according to the present invention. Such reactors comprise particularly a pumping circuit, a heat-exchanger and/or an agitating element.

In a preferred embodiment of the invention, the bioconversion unit is a relocatable bioconversion unit. In one embodiment, relocatable bioconversion unit is similar to the relocatable storage unit for acrylonitrile as described above. Using largely the same equipment for storing acrylonitrile or other monomers and the bioconversion step contributes to an economic process for manufacturing aqueous acrylamide solutions.

The bioconversion unit comprises a reaction vessel. The volume of the reaction vessel is not specifically limited and may range from 10 $m^3$ to 150 $m^3$, for example it may be about 20 $m^3$ to 50 $m^3$. Preferably, the reaction vessel should be double walled and should be horizontal. Such a construction avoids installing a pit for the collection of any leakage thereby ensuring an easier and quicker relocation of the reaction unit.

The bioconversion unit furthermore comprises means for mixing the reaction mixture and means for controlling the temperature of the contents of the vessel. The hydrolysis of acrylonitrile to acrylamide is an exothermal reaction and therefore heat generated in course of the reaction should be removed in order to maintain an optimum temperature for bioconversion. The bioconversion unit furthermore usually comprises means for measurement and control, for example means for controlling the temperature or for controlling the pressure in the vessel.

For temperature control, the preferred bioconversion unit comprises an external temperature control cycle comprising a pump which pumps the aqueous reactor contents from the storage vessel through a heat exchanger and back into the storage vessel, preferably via an injection nozzle.

In one embodiment, a separate, relocatable temperature control unit is used comprising pump and heat exchanger and which is connected with the bioconversion unit by pipes or flexible tubes. In a preferred embodiment, the temperature control cycle is integrated into the relocatable bioconversion unit. It may—for example—be located at one end of the unit besides the reaction vessel.

The reaction vessel may furthermore comprise means for mixing the aqueous reaction mixture, for example a stirrer.

Surprisingly, it has been found, that the external temperature control cycle described above may also be used as means for mixing. The stream of the aqueous reaction mixture which passes through the temperature control cycle and which is injected back into the reaction vessel causes a circulation of the aqueous reaction mixture within the reaction vessel which is sufficient to mix the aqueous reaction mixture.

Preferably, no stirrer is used for the mobile bioconversion unit. A stirrer is an additional mechanical device, which increases the technical complexity. When using the external temperature control cycle for mixing instead of a stirrer, the technical complexity can be reduced while still sufficient mixing during bioconversion can be ensured. Advantageously, without a stirrer a transportation step is easier, since no stirrer as additional technical component has to be removed before transportation. Further, a bioconversion unit without a stirrer offers more flexibility in form, shape, mechanical stability requirements and size for the bioconversion unit. In particular, a horizontal set-up for the relocatable bioconversion unit can be realized easier without a stirrer and with mixing just via the external temperature control cycle.

Adding acrylonitrile to the contents of the bioconversion unit may be performed in various ways. It may be added into the reaction vessel or it may be added into the temperature control cycle, for example after the pump and before the heat exchanger or after the heat exchanger. Injecting acrylonitrile into the temperature control cycle ensures good mixing of the reaction mixture with freshly added acrylonitrile. Preferably, acrylonitrile is added between pump and heat exchanger.

FIG. 3 schematically represents an embodiment of the relocatable bioconversion unit with an integrated temperature control cycle. The bioconversion unit comprises a frame (10), a double-walled reaction vessel mounted into the frame comprising an outer wall (11) and an inner wall (12). Preferred volumes of the reaction vessel have already been mentioned. In other embodiments, the reaction vessel is self-supporting and there is no frame (10). The reaction vessel is filled with the reaction mixture. The bioconversion unit furthermore comprises an external temperature control cycle comprising at least a pump (13) and a temperature control unit (14). The reaction mixture is circulated by means of a pump (13) from the reaction vessel to the temperature control unit (14) and is injected back into the storage vessel, preferably via an injection nozzle (16). In the depicted embodiment, acrylonitrile is injected into the temperature control cycle thereby ensuring good mixing (15). It may be added before or after the temperature control unit.

FIG. 3 shows an embodiment in which acrylonitrile is added into the temperature control cycle between the pump and the heat exchanger. The stream of reaction mixture injected back into the reaction vessel causes a circulation of the reaction mixture in the reaction vessel which ensures sufficient mixing of the contents of the reaction mixture.

The amount of reaction mixture cycled per hour through the temperature control cycle is chosen such that sufficient mixing to the contents of the reactor as well as sufficient temperature control is achieved. In one embodiment, the amount of reaction mixture cycled per hour through the temperature control cycle may be from 100% to 1000% of the total volume of the reaction mixture in the bioconversion unit, in particular from 200% to 1000% and for example from 500% to 800%.

Off-gases of the bioconversion unit may comprise acrylonitrile, acrylic acid and acrylamide. If necessary, according to the applicable rules such off-gases may be treated in a manner known in the art. For example, it may be possible to combust the off-gases.

In one embodiment, all off-gases containing acrylonitrile, acrylic acid and acrylamide may be washed in a scrubber.

The scrubber vessel may have a volume of 1 m³ to 100 m³, preferably a volume of 5 m³ to 100 m³, more preferably a volume of 10 m³ to 100 m³. It may be for example an ISO tank or relocatable storage vessel, preferably a double walled vessel. The scrubber water may preferably be collected in a tank and it may be re-used in the next bioconversion batch.

Biomass Removal

After bioconversion, the reaction vessel comprises an aqueous solution of acrylamide, which still comprises the biocatalyst suspended therein.

The biocatalyst preferably becomes removed completely, essentially completely, or partially before polymerization, however, removing the biocatalyst may not be absolutely necessary in every case. Whether it is necessary to remove the biocatalyst substantially depends on two factors, namely whether remaining biocatalyst negatively affects polymerization and/or the properties of the polyacrylamide obtained and/or the biocatalyst negatively affects the application of the obtained polyacrylamide solution. In one embodiment, at least 75%, preferably at least 90% by weight of the biomass—relating to the total of the biomass present—should be removed.

The method for removing the biocatalyst is not specifically limited. Separation of the biocatalyst may take place by for example filtration or centrifugation. In other embodiments, active carbon may be used for separation purpose.

Procedurally, for removing the biocatalyst there are several options.

In one embodiment, the aqueous acrylamide solution comprising the biocatalyst is removed from the bioconversion unit, passed through a unit for removing the biocatalyst, and thereafter the aqueous acrylamide solution is filled into a suitable storage unit for acrylamide, preferably a relocatable storage unit for acrylamide as described above.

In another embodiment, the aqueous acrylamide solution comprising the biocatalyst is removed from the bioconversion unit, passed through a unit for removing the biocatalyst and thereafter the aqueous acrylamide solution is filled directly into the monomer make-up unit, i.e. without intermediate storing in an acrylamide storage unit.

In another embodiment, the aqueous acrylamide solution comprising the biocatalyst is removed from the bioconversion unit and is filled directly, i.e. without removing the biocatalyst, into the monomer make-up unit. In said embodiment, the biocatalyst is still present in course of monomer make-up and is removed after preparing the aqueous monomer solution as described below.

In another embodiment, the aqueous acrylamide solution comprising the biocatalyst is removed from the bioconversion unit, passed through a unit for removing the biocatalyst and thereafter filled back into the bioconversion unit. In order to ensure complete discharge of the bioconversion unit before re-filling it with the acrylamide solution, the unit for removing the biocatalyst should comprise a buffer vessel having a volume sufficient for absorbing the contents of the bioconversion unit.

The above-mentioned methods for biocatalyst removal are for example applicable for partwise and/or complete removal of the biocatalyst. Further, it is preferred, that the completely or partly removed biocatalyst may be reused for a subsequent bioconversion reaction.

Provision of Acrylic Acid or Salts Thereof

In the context of the present invention, acrylic acid or salts thereof may be used as comonomer besides acrylamide. Basically, any kind of acrylic acid may be used for the process according to the present invention, for example acrylic acid obtained by catalytic oxidation of propene.

Acrylic acid may be provided in the acid form. In other embodiments, aqueous solutions of salts of acrylic acid may be provided, for example an aqueous sodium acrylate solutions.

In one embodiment of the invention ammonium acrylate available by enzymatic hydrolysis of acrylonitrile may be used for carrying out the process according of the present invention (hereinafter also "bio acrylate").

In a preferred embodiment of the present invention the manufacture of ammonium acrylate by enzymatic hydrolysis of acrylonitrile is also performed at location A in a modular unit. Suitable enzymes have been disclosed in WO 97/21827 A1 and the literature cited therein, and the publication describes also suitable conditions for carrying out the reaction. The manufacture of bio-acrylate may be carried out using stirred tank reactors or loop reactors, and in particular, the relocatable bioconversion unit described above may also be used.

Manufacturing bio-acrylate at location A also saves transport costs. Although acrylic acid may be provided to location A as pure compound, its molecular weight is ~36% higher than that of acrylonitrile.

Monomer Storage

Basically, it is possible to run step [1] as just-in-time-process, i.e. providing the monomers to the location A when monomers are needed and directly withdrawing the monomers from the transport vessels. However, in order to ensure an uninterrupted operation is preferred to hold available at least some storage capacity for the monomers at location A.

Depending on the chemical nature, the water-soluble, monoethylenically unsaturated monomers to be used may be provided as pure monomers or as aqueous solutions to location A. As already outlined above, it is also possible to provide a monomer premix to location A.

Acrylamide and other water-soluble, monoethylenically unsaturated monomers such as acrylic acid, ATBS, or DMA3Q, or mixtures thereof preferably may be stored in relocatable storage units. Details of such relocatable storage units for monomers have already been outlined above for acrylonitrile and we refer to the description above.

The monomers may be provided to location A by road tankers, ISO tanks, or rail cars and pumped into the relocatable storage unit(s).

Relocatable storage units basically may have any shape and orientation. They may be for example cylindrical or rectangular and the storage units may be in horizontal or vertical orientation. The volume and the dimensions are only limited by the condition that the storage units are relocatable. The volume may be—by the way of example—up to 200 m³, for example storage units having a volume from 60 to 80 m³ or from 120 to 180 m³.

In one embodiment, a relocatable storage unit with integrated temperature control cycle as depicted in FIG. 1 as shown above may be used for storing the monomers.

In another embodiment, a relocatable storage unit with a separate, external temperature control cycle as depicted in FIG. 2 as shown above may be used for storing the monomers.

In another embodiment, the relocatable storage unit is a vertical cylinder having a conical section at its lower end and a bottom valve for removing the liquids. Such a construction has the advantage that emptying can be affected simply by means of gravity. It may also comprise a cooling cycle.

If larger volumes need to be stored, a multiplicity of storage units for the same monomer may be used. Advantageously, the storage units may be connected with each other, for example by pipes, so that they can become filled and emptied together and furthermore, advantageously, only single cooling unit may be used to cool all storage units together.

As a rule, the temperature of the monoethylenically unsaturated monomers such as acrylamide, acrylic acid, ATBS or DMA3Q should not exceed 25° C. to 30° C.

Pure associative monomers as described above may be waxy solids and may be stored at room temperature. They may also be stored as aqueous solutions, for example as aqueous solutions comprising about 85% by weight of the associative monomer. Because the amounts of associative monomers are significantly smaller than the amounts of other monoethylenically unsaturated monomers smaller storage units than that described above may be used.

Acidic monomers such as acrylic acid or ATBS are often partially or completely neutralized for polymerization using suitable bases.

Bases, such as aqueous solutions of NaOH may also be stored in storage vessels as described above. A cooling cycle is not necessary. To the contrary, depending on the climatic conditions, a heating such as a heating element in the vessel may be necessary because concentrated NaOH freezes at about +15° C.

Monomer Make-Up

The aqueous monomer solution for polymerization comprises water and 15% to 50% by weight, in particular from 15% to 35% by weight of water-soluble, monoethylenically unsaturated monomers, relating to the total of all components of the aqueous monomer solution. The water-soluble, monoethylenically unsaturated monomers comprise at least acrylamide, preferably bio acrylamide.

The monomer concentration may be selected by the skilled artisan according to his/her needs. Details about adequately selecting the monomer concentration will be provided below.

In one embodiment of the invention, the monomer concentration is from 15% by weight to 24.9% by weight, for example from 20 to 24.9% by weight, relating to the total of all components of the aqueous monomer solution.

For preparing the aqueous monomer solution, the water-soluble, monoethylenically unsaturated monomers to be used are mixed with each other. All monomers and optionally additives may be mixed with each other in a single step but it may also be possible to mix some monomers and add further monomers in a second step. Also, water for adjusting the concentration of the monomers may be added. Water eventually used for rinsing lines in course of transferring the monomer solution into the polymerization unit, needs to be taken into consideration when adjusting the concentration.

Further additives and auxiliaries may be added to the aqueous monomer solution.

Examples of such further additives and auxiliaries comprise bases or acids for adjusting the pH value. In certain embodiments of the invention, the pH-value of the aqueous solution is adjusted to values from pH 4 to pH 7, for example pH 6 to pH 7.

Examples of further additives and auxiliaries comprise complexing agents, defoamers, surfactants, charge transfer agents, or stabilizers.

In one embodiment, the aqueous monomer solution comprises at least one stabilizer for the prevention of polymer degradation. The stabilizers for the prevention of polymer degradation are what are called "free-radical scavengers", i.e. compounds which can react with free radicals (for example free radicals formed by heat, light, redox processes), such that said radicals can no longer attack and hence degrade the polymer. Using such kind of stabilizers for the stabilization of aqueous solutions of polyacrylamides basically is known in the art, as disclosed for example in WO 2015/158517 A1, WO 2016/131940 A1, or WO 2016/131941 A1.

The stabilizers may be selected from the group of non-polymerizable stabilizers and polymerizable stabilizers. Polymerizable stabilizers comprise a monoethylenically unsaturated group and become incorporated into the polymer chain in course of polymerization. Non-polymerizable stabilizers don't comprise such monoethylenically unsaturated groups and are not incorporated into the polymer chain.

In one embodiment of the invention, stabilizers are non-polymerizable stabilizers selected from the group of sulfur compounds, sterically hindered amines, N-oxides, nitroso compounds, aromatic hydroxyl compounds or ketones.

Examples of sulfur compounds include thiourea, substituted thioureas such as N,N'-dimethylthiourea, N,N'-diethylthiourea, N,N'-diphenylthiourea, thiocyanates, for example ammonium thiocyanate or potassium thiocyanate, tetramethylthiuram disulfide, and mercaptans such as 2-mercaptobenzothiazole or 2-mercaptobenzimidazole or salts thereof, for example the sodium salts, sodium dimethyldithiocarbamate, 2,2'-dithiobis(benzothiazole), 4,4'-thiobis(6-t-butyl-m-cresol).

Further examples include dicyandiamide, guanidine, cyanamide, paramethoxyphenol, 2,6-di-t-butyl-4-methylphenol, butylhydroxyanisole, 8-hydroxyquinoline, 2,5-di(t-amyl)-hydroquinone, 5-hydroxy-1,4-naphthoquinone, 2,5-di(t-amyl)hydroquinone, dimedone, propyl 3,4,5-trihydroxybenzoate, ammonium N-nitrosophenylhydroxylamine, 4-hydroxy-2,2,6,6-tetramethyoxylpiperidine, (N-(1,3-dimethylbutyl)-N'-phenyl-p-phenylenediamine and 1,2,2,6,6-pentamethyl-4-piperidinol.

Preference is given to sterically hindered amines such as 1,2,2,6,6-pentamethyl-4-piperidinol and sulfur compounds, preferably mercapto compounds, especially 2-mercaptobenzothiazole or 2-mercaptobenzimidazole or the respective salts thereof, for example the sodium salts, and particular preference is given to 2-mercaptobenzothiazole or salts thereof, for example the sodium salts.

The amount of such non-polymerizable stabilizers—if present—may be from 0.1% to 2.0% by weight, relating to the total of all monomers in the aqueous monomer solution, preferably from 0.15% to 1.0% by weight and more preferably from 0.2% to 0.75% by weight.

In another embodiment of the invention, the stabilizers are polymerizable stabilizers substituted by a monoethylenically unsaturated group. Examples of stabilizers comprising monoethylenically unsaturated groups comprise (meth)acrylic acid esters of 1,2,2,6,-pentamethyl-4-piperidinol or other monoethylenically unsaturated groups comprising 1,2,2,6,6-pentamethyl-piperidin-4-yl groups. Specific examples of suitable polymerizable stabilizers are disclosed in WO 2015/024865 A1, page 22, lines 9 to 19. In one embodiment of the invention, the stabilizer is a (meth)acrylic acid ester of 1,2,2,6,6-pentamethyl-4-piperidinol.

The amount of polymerizable stabilizers—if present—may be from 0.01 to 2% by weight, based on the sum total of all the monomers in the aqueous monomer solution, preferably from 0.02% to 1% by weight, more preferably from 0.05% to 0.5% by weight.

In one embodiment, the aqueous monomer solution comprises at least one non-polymerizable surfactant. Adding such surfactants in particular is advisable when associative monomers are used. For such kind of polyacrylamides the surfactants lead to a distinct improvement of the product properties. Examples of suitable surfactants including preferred amounts have been disclosed in WO 2015/158517 A1, page 19, line, 23 to page 20, line 27. If present, such non-polymerizable surfactant may be used in an amount of 0.1 to 5% by weight, for example 0.5 to 3% by weight based on the amount of all the monomers used. Also adding a defoamer may be advisable when associative monomers are used.

For preparing the aqueous monomer solution basically any kind of equipment suitable for mixing monomers may be used, for example a stirred vessel.

Preferably, the preparation of the aqueous monomer solution is performed in a relocatable monomer make-up unit.

In one embodiment, a relocatable monomer make-up unit is similar to the relocatable bioconversion unit as described above. Using largely the same equipment for storing acrylonitrile or other monomers, the bioconversion step and for monomer make-up contributes to an economic process for manufacturing aqueous acrylamide solutions.

The monomer make-up unit comprises a monomer make-up vessel in which the monomers, water and optionally further components are mixed.

The volume of the monomer make-up vessel is not specifically limited and may range from 10 m$^3$ to 150 m$^3$, for example it may be about 20 to 90 m$^3$. The monomer make-up vessel may be single walled or double walled and it may be horizontal or vertical.

The monomer make-up unit furthermore comprises means for controlling the temperature of the aqueous monomer solution. Usually, the temperature of the aqueous monomer solution should be not more than 30° C., preferably not more than 25° C., for example from −5° C. to +5° C. The monomer make-up unit furthermore comprises means for measurement and control.

For temperature control, the monomer make-up unit comprises an external temperature control cycle comprising a pump which pumps the aqueous reactor contents from the storage vessel through a heat exchanger and back into the storage vessel, preferably via an injection nozzle.

The temperature control cycle may be a separate, relocatable temperature control unit comprising pump and heat exchanger and which is connected with the monomer make-up vessel by pipes or flexible tubes. In another embodiment, the temperature control cycle may be integrated into relocatable storage unit. It may—for example—be located at one end of the unit besides the monomer make-up vessel.

The monomer make-up vessel may be equipped with a stirrer for mixing the components of the aqueous monomer solution with each other.

However, in the same manner as with the bioreactor, the external temperature control cycle may be used as means for mixing. The stream of the aqueous monomer mixture which passes through the temperature control cycle and which is injected back into the monomer make-up vessel causes a circulation of the aqueous reaction mixture within the reaction vessel which is sufficient to mix the aqueous reaction mixture.

FIG. 4 represents a schematically one embodiment of the relocatable monomer make-up unit. The monomer make-up unit comprises a frame (20), a double-walled monomer make-up vessel mounted into the frame comprising an outer wall (21) and an inner wall (22). In another embodiment, the monomer make-up vessel is self-supporting and a frame is not necessary. The monomer make-up vessel is filled with the monomer mixture. The monomer make-up unit furthermore comprises an external temperature control cycle comprising at least a pump (23) and a temperature control unit (24). The monomer mixture is circulated by means of a pump (23) from the storage vessel to the temperature control unit (24) and is injected back into the storage vessel, preferably via an injection nozzle (25). The monomers may be added directly into the storage vessel or into the temperature control cycle (26) as indicated in FIG. 4. The stream of monomer mixture injected back into the monomer make-up vessel causes a circulation of the monomer mixture in the storage vessel which ensures sufficient mixing of the contents of the monomer mixture.

In another embodiment, a separate temperature control cycle may be used.

The monomers to be mixed with each other and with water are preferably mixed in the monomer make-up vessel, however in another embodiment, it is possible to add the monomers into the temperature control cycle. It is frequently advisable, to first add water to the monomer make-up vessel and then one or more further monomers and/or acids or bases and/or further additives. If acidic monomers such as acrylic acid are used, they should be neutralized before adding acrylamide. For copolymers comprising acrylic acid and acrylamide at first the necessary amount of water may be added into the vessel, followed by NaOH, thereafter acrylic acid and thereafter acrylamide.

Further additives which optionally might be present such as complexing agents, defoamers, surfactants, charge transfer agents, or stabilizers as mentioned above may be dissolved in aqueous solvents, preferably water in suitable dissolution units and the solutions also added into the monomer make-up vessel.

In another embodiment of the invention, the bioconversion unit may also be used for monomer make-up.

In a preferred embodiment, the aqueous acrylamide solution does no longer comprise the biocatalyst. However, in another embodiment the acrylamide solution still comprises the biomass. In said embodiment, the biocatalyst may be removed after preparing the aqueous monomer solution in the same manner as described above or it may not be removed. Criteria for deciding in which cases it may not be necessary to remove the biocatalyst have already been mentioned above.

After mixing the aqueous monomer solution it is transferred from the monomer make-up vessel (or any other vessel serving as monomer make-up vessel such as the bioconversion unit) to the polymerization unit. Such connection for transferring the aqueous monomer solution hereinafter also is referred to as "monomer feed line".

In one embodiment, associative monomers may also be added into the monomer make-up vessel. However, in a preferred embodiment, aqueous solutions of the associative monomers may be metered into the monomer feed line.

In another embodiment of the invention, the polymerization unit itself may be used for monomer make-up. As will be detailed below, the polymerization unit may be connected to a temperature control unit before polymerization, so that the temperature of the monomer solution may also controlled and adjusted until directly before the start of polymerization. As will be detailed also below, the polymerization unit may comprise injection nozzles for nitrogen or other inert gases in order to inert the contents of the polymerization unit and such injection of inert gases also efficiently mixes the contents of polymerization unit. Also, combinations are possible, for example providing a monomer concentrate in a separate monomer make-up unit and diluting the aqueous monomer solution in the polymerization unit with additional water. In another example, acids or bases—if necessary—may be added not into a separate monomer make-up unit but directly to the polymerization unit.

Step [1]—Polymerization of an Aqueous Monomer Solution

In course of step [1] the aqueous monomer solution prepared as outlined above is polymerized in the presence of suitable initiators for radical polymerization under adiabatic conditions thereby obtaining an aqueous polyacrylamide gel. Step [1] is carried out at location A.

Such a polymerization technique is also briefly denominated by the skilled artisan as "adiabatic gel polymerization". Reactors for adiabatic gel polymerization are unstirred. Due to the relatively high monomer concentration the aqueous monomer solution used solidifies in course of polymerization thereby yielding an aqueous polymer gel. The term "polymer gel" has been defined for instance by L. Z. Rogovina et al., Polymer Science, Ser. C, 2008, Vol. 50, No. 1, pp. 85-92.

"Adiabatic" is understood by the person skilled in the art to mean that there is no exchange of heat with the environment. This ideal is naturally difficult to achieve in practical chemical engineering. In the context of this invention, "adiabatic" shall consequently be understood to mean "essentially adiabatic", meaning that the reactor is not supplied with any heat from the outside during the polymerization, i.e. is not heated, and the reactor is not cooled during the polymerization. However, it will be clear to the person skilled in the art that—according to the internal temperature of the reactor and the ambient temperature—certain amounts of heat can be released or absorbed via the reactor wall because of temperature gradients, but this effect naturally plays an ever lesser role with increasing reactor size.

The polymerization of the aqueous monomer solution generates polymerization heat. Due to the adiabatic reaction conditions, the temperature of the polymerization mixture increases in course of polymerization.

The kind of polymerization unit for carrying out the present invention is not specifically limited. Preferably, the polymerization unit is a relocatable polymerization unit. It may be transported for instance by trucks or railcars.

The polymerization unit preferably has a volume of more than 1 m$^3$, for example from 1 m$^3$ to 200 m$^3$. In one embodiment, the polymerization unit has a volume from 5 m$^3$ to 40 m$^3$, and more preferably 20 m$^3$ to 30 m$^3$. In other embodiments, larger polymerization units may be used, for example polymerization unit having a volume from 100 m$^3$ to 200 m$^3$, or from 120 m$^3$ to 160 m$^3$.

The polymerization unit may be of cylindrical or conical shape. Preferably, the polymerization unit is cylindrical having a conical taper at the bottom and a bottom opening for removing the aqueous poly acrylamide gel. In one embodiment, there may be additionally a cylindrical section between the lower end of the conical taper and the bottom opening. The inner wall of the polymerization unit may preferably be coated with an anti-adhesive coating. Basically, anti-adhesive coatings are known in the art. Examples comprise polypropylene, polyethylene, epoxy resins and fluorine containing polymers such as polytetrafluoroethylene or perfluoroalkoxy polymers.

One embodiment of a polymerization unit for use in the present invention is schematically shown in FIG. 5, hereinafter also denoted as polymerization unit P1. The polymerization unit P1 comprises a cylindrical upper part (30) and a conical part (31) at its lower end. At the lower end, there is a bottom opening (32) which may be opened and closed.

After polymerization, the polyacrylamide gel formed is removed through the opening (32). It furthermore comprises means (33) such as legs or similar elements allowing to deploy the polymerization unit in a vertical manner.

In one embodiment of the invention, the diameter (D) of the polymerization unit in the cylindrical section may in particular be from 1.5 to 2.5 m, preferably from 2 m to 2.5 m and the length (L) of the cylindrical section may be from 4 to 6 m, preferably 5 to 6 m. The conus angle α in the conical part may be from 15° to 90°, preferably from 20° to 40°. The volume of the polymerization unit P1 described herein may preferably be from 20 m$^3$ to 30 m$^3$. Besides the opening (32) the polymerization unit P1 comprises one or more feeds for the aqueous monomer solution, initiator solutions, gases such as nitrogen or other additives. The inner wall of the polymerization unit P1 may be coated with an anti-adhesive coating. The diameter of the bottom opening (32) may for example be from 0.2 to 0.8 m, in particular from 0.4 to 0.7 m, preferably from 0.5 to 0.7 m.

Other embodiments comprise polymerization units P1 having basically the same shape, i.e. a cylindrical upper part and a conical part at its lower end and a bottom opening, however having a diameter from about 3 m to 4.5 m, a length of the cylindrical section from 10 m to 12 m and a length of the concial section from 1.5 to 2.5 m.

For polymerization and removal of the polymer gel the polymerization unit P1 is operated in a vertical position as depicted in FIG. 5. For transport, it may preferably be tilted to a horizontal position.

For polymerization, the aqueous monomer solution prepared in course of step [1] is filled into the polymerization unit, in particular into the polymerization unit P1. For that purpose, the monomer make-up vessel (or any other vessel serving as monomer make-up vessel such as the bioconversion unit) is connected with the polymerization unit by a monomer feed line.

As already outlined above, in another embodiment the aqueous monomer solution may be prepared in the polymerization unit itself. In such embodiment, the polymerization unit already is filled with an aqueous monomer solution.

The polymerization is performed in the presence of suitable initiators for radical polymerization. Suitable initiators for radical polymerization, in particular for adiabatic gel polymerization are known to the skilled artisan.

In a preferred embodiment, redox initiators are used for initiating. Redox initiators can initiate a free-radical polymerization even at temperatures of less than +5° C. Examples of redox initiators are known to the skilled artisan and include systems based on $Fe^{2+}/Fe^{3+}$- $H_2O_2$, $Fe^{2+}/Fe^{3+}$- alkyl hydroperoxides, alkyl hydroperoxides—sulfite, for example t-butyl hydroperoxide—sodium sulfite, peroxides—thiosulfate or alkyl hydroperoxides—sulfinates, for example alkyl hydroperoxides/hydroxymethane-sulfinates, for example t-butyl hydroperoxide—sodium hydroxymethanesulfinate.

Furthermore, water-soluble azo initiators may be used. The azo initiators are preferably fully water-soluble, but it is sufficient that they are soluble in the monomer solution in the desired amount. Preferably, azo initiators having a 10 h $t_{1/2}$ in water of 40° C. to 70° C. may be used. The 10-hour half-life temperature of azo initiators is a parameter known in the art. It describes the temperature at which, after 10 h in each case, half of the amount of initiator originally present has decomposed.

Examples of suitable azo initiators having a 10 h $t_{1/2}$ temperature between 40 and 70° C. include 2,2'-azobis[2-(2-imidazolin-2-yl)propane] dihydrochloride (10 h $t_{1/2}$ (water): 44° C.), 2,2'-azobis(2-methylpropionamidine) dihydrochloride (10 h $t_{1/2}$ (water): 56° C.), 2,2'-azobis[N-(2-carboxyethyl)-2-methylpropionamidine hydrate (10 h $t_{1/2}$ (water): 57° C.), 2,2'-azobis{2-[1-(2-hydroxyethyl)-2-imidazolin-2-yl]propane} dihydrochloride (10 h $t_{1/2}$ (water): 60° C.), 2,2'-azobis(1-imino-1-pyrrolidino-2-ethylpropane) dihydrochloride (10 h $t_{1/2}$ (water): 67° C.) or azobis(isobutyronitrile) (10 h $t_{1/2}$ (toluene): 67° C.).

In one embodiment of the invention a combination of at least one redox initiator and at least one azo initiator is used. The redox initiator efficiently starts polymerization already at temperatures below +5° C. When the reaction mixture heats up, also the azo initiators decompose and also start polymerization.

The initiators preferably are added as aqueous solutions to the aqueous monomer solution. The initiator raw material may be stored at location A in a cold storage container. Dissolving the initiators in water may be performed using suitable initiator make-up vessels. The initiator make-up vessel may comprise a temperature control cycle. Instead of an own temperature control cycle, cold water, for example water having a temperature of less than +5° C. may be used for dissolving the initiators. The initiator make-up vessels furthermore may comprise means for mixing such as a stirrer. However, mixing may also be conducted by bubbling an inert gas through the aqueous mixture thereby simultaneously mixing and inerting the aqueous mixture. The solutions may be filtered before use.

Solutions of azo initiators may be added into the monomer feed line while the aqueous monomer solution is transferred from the monomer make-up vessel to the polymerization unit. In another embodiment solutions of azo initiators may already been added to the monomer make-up vessel, provided the monomer solution has already been cooled to temperatures below ambient temperature, preferably to less than +5° C. and the 10 h $t_{1/2}$ temperature of the initiator is high enough so that the initiator doesn't decompose prematurely.

Solutions of redox initiators may be added into the monomer feed line or into the polymerization unit.

Before polymerization oxygen from the reactor and the reaction mixture to be polymerized needs to be removed. Deoxygenation is also known as inertization.

In one embodiment, inertization is performed in the polymerization unit. For that purpose, inert gases such as nitrogen or argon are injected into the reactor filled with the monomer solution. Preferably, nozzles for injecting inert gases are located in the bottom of the polymerization unit. In the polymerization unit P1 they may for example be located in the conical taper. The bubbles of inert gases rising in the reactor remove oxygen and simultaneously mix the contents of the reactor very efficiently. Initiator solutions metered into the reactor are mixed with the aqueous solution by means of the inert gas injection.

In another embodiment, inertization may be performed in the monomer feed line. Inert gases such as nitrogen or argon may be injected into the feed line. In order to ensure effective mixing of the gas injected and the aqueous gases injected it is frequently desirable that the monomer feed line additionally comprises a static mixture. The gas injected into the monomer feed line may be removed before entering into the reactor by means of a suitable degassing unit such as the degassing units described in WO 2003/066190 A1 or in CN 202492486 U. In another embodiment, no separate degassing unit is used, but the solution is degassed after entering into the polymerization unit. In one embodiment, the monomer solution enters into the reactor by means of a spray nozzle for the purpose of removing gas.

Of course, it is possible to combine the two embodiments for degassing, i.e. to purging the polymerization unit with inert gases and degassing the monomer mixture.

The radical polymerization starts after adding the initiator solutions, preferably solutions of redox initiators, to the aqueous monomer solution thereby forming an aqueous polyacrylamide gel. Due to the polymerization heat generated in course of polymerization and the adiabatic reaction conditions, the temperature in the polymerization unit increases.

In the following, the temperature of the aqueous monomer solution before the onset of polymerization shall be denominated as $T_1$ and the temperature of the aqueous polymer gel directly after polymerization shall be denominated as $T_2$. It goes without saying that $T_2 > T_1$.

Within the context of the present invention, the temperature $T_1$ should not exceed 30° C., in particular $T_1$ should not exceed 25° C. In one embodiment, $T_1$ may be from −5° C. to +30° C., for example from −5° C. to +25° C. or from −5° C. to +5° C. The temperature $T_1$ of the monomer solution may be adjusted as already disclosed above, i.e. already the monomer solution in the monomer make-up vessel may be cooled appropriately. Of course, also the temperature control unit for adjusting $T_1$ may be located in the monomer feed line, or the polymerization unit may be connected to a temperature control unit before polymerization, so that the monomer solution may still be cooled in the polymerization unit until directly before the start of polymerization.

As the polymerization is carried out under adiabatic conditions, the temperature $T_2$ reached in course of polymerization is not influenced by external heating or cooling but only depends on the polymerization parameters chosen. But suitable choice of the polymerization parameters, the skilled artisan can adjust $T_2$. Because the reaction is adiabatic, the temperature increase in course of polymerization basically depends on the heat of polymerization generated in course of polymerization, the heat capacity of contents of the polymerization unit and the temperature $T_1$ of the monomer solution, i.e. the temperature before the onset of polymerization. Due to high water contents of the mixture for polymerization the heat capacity of the mixture for polymerization is dominated by the heat capacity of water and it may of course be measured. The polymerization heat per mole (or per mass) for common monoethylenically unsaturated monomers is known in the art and may therefore be gathered from the scientific literature. Of course, it may also be measured. So, it is possible for the skilled artisan to calculate at least roughly the heat of polymerization for specific monomer compositions and specific monomer concentrations. The higher the concentration of the monoethylenically unsaturated monomers in the aqueous solution the more heat of polymerization is generated. $T_2$ may be roughly calculated from the parameters mentioned above by the formula $T_2 = T_1 + [(\text{polymerization heat})/(\text{heat capacity})]$. The temperature $T_2$ should be at least 45° C., preferably at least 50° C., for example from 50° C. to 100° C., for example from 55° C. to 95° C. In an embodiment of the invention $T_1$ is from −5° C. to +25° C. and $T_2$ is from 50° C. to 95° C.

In certain embodiments of the invention, $T_2$ should be from 45° C. to 70° C., in particular from 50° C. to 70° C., preferably from 50° C. for 65° C. In one embodiment, $T_1$ is from −5° C. to +25° C. and $T_2$ is from 50° C. to 70° C.

The time of polymerization may be from 2 to 24 h, for example from 3 to 6 h.

Step [2] Removal of the Aqueous Polyacrylamide Gel

Step [2] is also carried out at location A. In step [2], the aqueous polyacrylamide gel is removed from the polymerization unit. After removal from the polymerization unit the aqueous polymer gel is further processed by comminuting and mixing it with an aqueous fluid.

Basically, removing the aqueous polyacrylamide gel may be performed by any kind of technology. The details depend on the specific design of the polymerization unit and the connected downstream processing equipment.

The aqueous polyacrylamide gel may for example be removed by mechanical means from the polymerization unit. In other embodiments, the polymerization unit may be opened completely at the upper side, e.g. by removing a cover plate. By tipping the polymerization unit the gel block may be removed more or less as a whole from the reactor. Preferably, the aqueous polyacrylamide gel may be removed by applying pressure onto the gel and pressing it through an opening in the polymerization unit. By the way of example, pressure may be generated by mechanical means such as a piston, by means of gases such as compressed air, nitrogen, argon or by means of aqueous fluids, in particular water.

For removing the polyacrylamide gel from the preferred polymerization unit P1, the polymerization unit P1 is operated in vertical position. The aqueous polyacrylamide gel is removed through the opening (26) at the bottom which is opened for the purpose of removing by applying pressure onto the gel from the top side of the reactor. Pressure may be applied using gases and/or water. Examples of gases comprise pressurized air, nitrogen or argon. Basically, any kind of gas may be used, provided it does not react with the polyacrylamide gel. In another embodiment, the polymerization unit may comprise mechanical means, such as a piston for generating pressure. The pressure to be applied for removing the gel may be selected by the skilled artisan. Factors relevant for the selection of the pressure include the viscosity of the polyacrylamide gel, the width of the bottom opening (26), the geometry of the polymerization unit or—if present—the kind of anti-adhesive layer. For example, pressures may range from 110,000 Pa to 1,000,000 Pa, in particular 150,000 Pa to 750,000 Pa, for example 200,000 Pa to 500,000 Pa (absolute pressures). Removing the aqueous polyacrylamide gel may be supported by a thin water-film at the inner walls of the reactor, in particular on the walls of the conical part of the reactor. Such a thin water-film may be generated by injecting water or an aqueous fluid through fine holes in the wall of the reactor into the reactor, in particular holes in the conical part. Should some aqueous acrylamide gel remain in the polymerization unit, the polymerization unit may be rinsed with water to remove the remaining amounts. In another embodiment, the aqueous polyacrylamide gel may remain in the polymerization unit until the next polymerization.

The bottom opening (26) of the polymerization unit P1 may be connected with a comminution unit—if present—or directly with a suitable dissolution unit, for instance with a stirred vessel. Said connection may simply be a pipe but it may also comprise means for transporting the gel such as for example screw conveyors or belt conveyors.

In other embodiments, the polyacrylamide gel may be conveyed by the gas pressure from the polymerization reactor into a pump. Such a pump may be helpful in achieving a constant feed rate and a constant pressure for the consecutive step [4] of comminuting and dissolving the polyacrylamide gel. Depending on the nature of the equipment used for step [4] ensuring constant feed rate and a constant pressure may be difficult to achieve by gas pressure alone. A pump may in particular be helpful, if it is the aim to convey the polyacrylamide gel through a comminution unit in course of step [4] causing a significant pressure drop, such as for example conveying the polyacrylamide gel through a hole perforation plate and/or conveying the gel through a relatively long pipe.

When using a pipe for transporting the gel, in one embodiment of the invention, also some water may be injected into the pipe in such a manner that a water-film may be generated at the walls of the pipe. Such a thin water-film facilitates the transport of the gel in the pipe by reducing friction and therefore reducing pressure loss.

Suitable are all pumps capable of transporting the polyacrylamide gel, in particular positive displacement pumps such as a progressive cavity pump or a screw spindle pump.

Step [3] Comminution the Aqueous Polyacrylamide Gel and Mixing with an Aqueous Liquid In course of step [3] the aqueous polyacrylamide gel is comminuted and mixed with an aqueous liquid, thereby obtaining an aqueous polyacrylamide concentrate having a concentration of 1.0 to 14.9% by weight of polyacrylamides, relating to the total of all components of the aqueous polyacrylamide concentrate. Step [3] is carried out at location A.

As will be detailed below, the concentrate may optionally be further diluted in course of a later step of the process, i.e. after transporting the concentrates to location B. So, the term "concentrate" as used in the context of the present invention simply is used to clearly distinguish the concentrates made in step [3] and transported to a location B in course of step [4] from more diluted aqueous polyacrylamide solutions which might result from such an additional dilution step after step [5]. Depending on parameters such as the chemical composition, the molecular weight and the concentration, the concentrate may be also solution or a (soft) solid. In general, the concentrate is pumpable.

In course of mixing the comminuted aqueous polyacrylamide gel with an aqueous liquid, ideally a homogeneous mixture of polyacrylamides and aqueous liquid should be obtained, i.e. a homogeneous aqueous polyacrylamide concentrate should be obtained. However, the invention shall not be limited to such an embodiment and shall encompass also aqueous polyacrylamide concentrates which are not absolutely homogeneous.

In one embodiment of the invention, the concentration of the polyacrylamides in the aqueous polyacrylamide concentrate is from 2.1% to 14.9% by weight, relating to the total of all components of the aqueous polyacrylamide concentrate, in particular from 2.1% by weight to 10% by weight, preferably form 3.1% by weight to 10% by weight. More preferably, the concentration is from 3.1% by weight to 7% by weight, for example from 4% by weight to 6% by weight.

Comminution and mixing with an aqueous liquid may be carried out simultaneously, they may be separate steps to be carried out consecutively or any other combination, i.e. that already some aqueous liquid is added in course of comminution are more aqueous liquid thereafter. Preferably, at least some amount of aqueous liquid should be added already in course of comminution.

The aqueous liquid used for mixing with the aqueous polyacrylamide gel comprises water. The term "water" includes any kind of water such as desalinated water, fresh water or water comprising salts, such as brines, sea water, formation water, produced water or mixtures thereof. Besides water, the aqueous liquid may comprise organic solvents miscible with water, however the amount of water relating to the total of all solvent should be at least 70% by weight, preferably at least 90% by weight, more preferably at least 95% by weight. Adding a limited amount of organic solvent may be helpful in order to manufacture a "winterized" polyacrylamide concentrate having a lowered freezing point. Such an embodiment may be helpful if the concentrates are transported and/or stored in cold regions, for example in arctic regions. In one embodiment, the aqueous liquid comprises only water as solvent.

Furthermore, the aqueous liquid may optionally also comprise additives such as for example surfactants, complexing agents, biocides, bases, acids of the like. Kind and amount of such additives may be selected according to the intended use of the aqueous polyacrylamide solution. Of course, additives may also be added at a later stage, for example after complete dissolution of the aqueous polyacrylamide gel.

The particle size of the aqueous polyacrylamide gel pieces obtained in course of comminution is not specifically limited. In an embodiment of the invention, particles of aqueous polyacrylamide gel should conveniently have a size such that at least two dimensions are no more than 1 cm, preferably no more than 0.5 cm. Preferably three dimensions of the aqueous polyacrylamide gel pieces should be no more than 1 cm, preferably no more than 0.5 cm. There is no lower limit necessary for the aqueous polyacrylamide gel pieces, since the smaller the pieces the easier it will be for the polymer to dissolve. Frequently, aqueous polyacrylamide gel pieces may have a size such that three dimensions are as low as 0.1 cm. Often the aqueous polyacrylamide gel pieces tend to have three dimensions each of from 0.1 cm to 0.5 cm.

Basically, any kind of comminution means may be used for disintegrating the aqueous polyacrylamide gel into smaller particles. Examples of suitable means for comminuting aqueous polyacrylamide gels include cutting devices such as knives or perforated plates, crushers, kneaders, static mixers or water-jets.

Suitable comminution units may be connected directly with the polymerization unit. In other embodiments, the comminution unit may not be directly connected with the polymerization unit but distant from it and the polyacrylamide gel is transported to the comminution unit, for example by screw conveyors, belt conveyors, or pumps.

The comminution unit preferably also is a relocatable unit.

When the preferred polymerization unit P1 is used, preferably, the bottom opening (32) may be connected with the comminution unit, either directly or with a pump as outlined above in between.

FIG. 6 schematically shows such an embodiment. The aqueous polyacrylamide gel (35) in the polymerization unit enters through the bottom opening (32) into a pump (38). The pump transports the aqueous polyacrylamide gel into a comminution unit (34) and the comminuted polyacrylamide gel (36) leaves the comminution unit for further processing.

Basically, any kind of comminution unit may be used, for example static cutting units or dynamic cutting units. High shear forces should be avoided in order to not damage the aqueous gel.

Static Cutting Device

In one embodiment of the invention, the aqueous polyacrylamide gel is conveyed through a static cutting device, such as knives or metal grills thereby obtaining smaller gel particles. A static cutting device may be located directly under the bottom opening (32). In other embodiments, a pump as described above may transport the polyacrylamide gel to a more distant static cutting device. Suitable static cutting devices comprise perforated plates or metal grills, such as disclosed, for instance, in U.S. Pat. No. 4,605,689. In one embodiment, the aqueous gel is conveyed through the static cutting device together with an aqueous liquid as described above, preferably water, thereby yielding a mixture of particles of an aqueous polyacrylamide gel in an aqueous liquid. The aqueous liquid is metered in before the gel enters into the static cutting device, for example into the connection between the bottom opening (32) and the static cutting device or into the connection between the pump and the static cutting device. In one embodiment, not the entire amount of the aqueous liquid to achieve the desired concentration is added at this stage but only a portion of it. Surprisingly, already 1% of the total amount of aqueous liquid significantly improves conveying the aqueous polyacrylamide gel through the static cutting device.

Perforated Plate

In another embodiment of the invention, the aqueous polyacrylamide gel is conveyed through a perforated plate. An extruder or a screw conveyor or pump may be used to generate the necessary pressure for passing the perforated plate. In course of passing through the perforated plates a number of separate cords of aqueous acrylamide gel are formed. They may be cut by a rotating knife or may be flushed away by means of a water jet and conveyed to the dissolution unit.

Static Mixer

In another embodiment of the invention, the aqueous polyacrylamide gel is conveyed together with an aqueous liquid through a static mixer thereby yielding a mixture of particles of an aqueous polyacrylamide gel in an aqueous liquid. Of course, also a plurality of static mixers may be used. The aqueous liquid is metered in the product line before the aqueous polyacrylamide gel enters into the static mixer, for example into the connection between the bottom opening (26) and the static mixer, or into the connection between the pump and the static mixer. In an embodiment, the entire amount of aqueous liquid necessary for achieving the desired concentration is already added at this stage. In another embodiment, not the entire amount is added.

Water-Jet Cutting

In one embodiment of the invention, the aqueous polyacrylamide gel is cut into pieces of aqueous polyacrylamide gel by means of a water-jet cutting unit. The water-jet cutting unit cuts the aqueous polyacrylamide gel by means of at least one water jet at a pressure of at least $150*10^5$ Pa thereby obtaining a mixture of particles of an aqueous polyacrylamide gel in an aqueous liquid.

Preferably, the surrounding wall section of the water jet cutting unit is a tubular section, a conical section or a combination of tubular and conical sections. The aqueous polyacrylamide gel may then enter into the water jet cutting unit from one end, pass through the cutting stage to reduce the size of the aqueous polyacrylamide gel and desirably the so formed aqueous polyacrylamide gel pieces should exit from the outlet. Aqueous liquid from the cutting stage, desirably should also exit from the outlet. Thus, a mixture of aqueous polyacrylamide gel pieces and water optionally comprising dissolved polymer gel may be formed in the cutting stage.

The surrounding wall section of the water jet cutting unit may be in any suitable orientation. Nevertheless, it is preferred that the surrounding wall section is substantially upright, with the inlet at the upper end and the outlet at the lower end. The upper end may be preferably connected directly with the bottom opening (3) of the polymerization unit by suitable means.

The passage of the aqueous polyacrylamide gel may be by gravity alone or may be fed into the water jet cutting unit under pressure, for instance, by pumping, mechanically feeding, by gas pressure or by the action of a vacuum.

Preferably, the aqueous polyacrylamide gel is fed into the water jet cutting unit by means of gas or water pressure exerted on the contents of the polymerization unit P1 forming the aqueous polyacrylamide gel. Alternatively, or additionally, the aqueous polyacrylamide gel is fed into the water jet cutting unit by means of mechanical conveying devices, such as scrolls.

The at least one water-jet has a pressure of at least $150*10^5$ Pa. The pressure may be considerably higher than this, for instance, up to $10,000'10^5$ Pa. However, it is not normally necessary for the pressure to be as high as this and lower pressures, for instance no higher than $7,500*10^5$ Pa are usually adequate. In one embodiment of the invention, the pressure of the water jet in the cutting unit has a pressure of from $150*10^5$ Pa to $5,000*10^5$ Pa, preferably from $200*10^5$ Pa to $2,000*10^5$ Pa, more preferably from $250*10^5$ Pa to $1000*10^5$ Pa.

Typically, the water jet would flow from a nozzle having a nozzle orifice of suitable diameter. By the term nozzle we mean a device which is designed to control the direction or the characteristics of a fluid flow, including to increase the velocity, as it exits. In general, the nozzle orifice diameter should be from 0.1 mm to 3.00 mm, for instance, from 0.25 mm to 2.00, or from 0.25 mm to 1.00 mm, suitably from 0.30 mm to 0.90 mm, desirably from 0.40 mm 0.80 mm. It may be desirable to employ a multiplicity of nozzles on a head in which each nozzle delivers a stream of aqueous liquid at the aforementioned pressures of at least $150*10^5$ Pa. When a multiplicity of nozzles on a head is employed the number of nozzles may be at least 2, for instance, from 2 to 10 nozzles. The nozzles may be arranged in one plane or in different planes and angles.

The nozzles may be arranged in such a way, for instance over a domed surface of the head, that the multiplicity of streams radiate out in different axis. Such a multiplicity of nozzles may be arranged such that the streams of aqueous liquid from an array each travelling in different directions.

The at least one nozzle may rotate or oscillate.

In one embodiment, the at least one nozzle oscillates. Such oscillation of the nozzle may produce a fan shaped water stream sweep pattern. In this embodiment of the invention, it may be of particular value to employ a multiplicity of nozzles which can oscillate. Typically, the number of nozzles may be from 2 to 8, preferably from 2 to 6. It may also be desirable that a multiplicity of nozzles are arranged on at least one head, each head containing from 2 to 10 nozzles. It may be desirable for the multiplicity of heads, for instance, from 2 to 10 heads, each head containing the multiplicity of nozzles, to be employed. In this case each of the heads may separately oscillate.

Such multiplicity of nozzles or multiplicity of heads each may be positioned circumferentially with respect to the aqueous polyacrylamide gel, such that the water streams extend inwardly. The multiplicity of nozzles and/or multiplicity of heads may be positioned evenly such that the distance between all adjacent nozzles is equal. Alternatively, they may not to be evenly spaced.

Thus, when the multiplicity of nozzles or multiplicity of heads are arranged circumferentially the aqueous polyacrylamide gel would then pass within the circumferentially positioned nozzles and be cut by the multiplicity of aqueous liquid streams. The at least one oscillating nozzle or head may be moved by a suitable actuator mechanism.

Each oscillating nozzle may have a sweep of up to 180°. Typically, the sweep may be 30° to 180°, for instance from 35° to 75°. The exact range of the sweep will often depend on the exact number of nozzles employed. The oscillation frequency should for instance be up to 50 $s^{-1}$ (cycles per second), typically from 0.5 $s^{-1}$ to 50 $s^{-1}$.

When the at least one nozzle, for instance, multiplicity of nozzles, or at least one head, for instance multiplicity of heads, is/are arranged circumferentially with respect to the aqueous polyacrylamide gel, each of the at least one nozzles or at least one head may rotate circumferentially about the aqueous polyacrylamide gel. When the circumferentially arranged at least one nozzle or at least one head rotates it may be desirable that each nozzle or each head may independently oscillate as given above. Alternatively, it may be desirable that when the circumferentially arranged at least one nozzle or at least one head rotates they may not oscillate. The rotation of the at least one nozzle or at least one head may be achieved by a suitable drive mechanism.

In another preferred embodiment of the invention, the at least one nozzle rotates and the stream of aqueous liquid generated forms a circular sweep pattern. The at least one nozzle may be a multiplicity of nozzles housed on at least one head. Such at least one rotating nozzle may be rotated by the action of a suitable motorized drive mechanism.

It may be desirable to employ more than one rotating nozzle, for instance, a multiplicity of nozzles housed on at least one head. However, it is usually only necessary to employ one rotating nozzle or where more than one nozzle is employed the multiplicity of nozzles are arranged on one head.

In one embodiment of the invention, the at least one rotating nozzle, or at least one head is mounted centrally, and the aqueous liquid stream extends substantially perpendicular to the axis of the direction of the incoming aqueous polyacrylamide gel. In this embodiment, the aqueous liquid stream sweep pattern is disc shaped. In an adaptation of this preferred aspect the rotating nozzle or head, which is/are mounted centrally, may generate at least one stream of liquid which is not perpendicular to the direction of the incoming aqueous polyacrylamide gel, but instead is angled such that the at least one aqueous liquid stream sweep pattern is a cone shaped, for instance, an upright cone where the at least one aqueous liquid stream is angled downwards, or an inverted cone where the at least one aqueous liquid stream is angled upwards. Where the at least one aqueous liquid stream is angled either upwards or downwards it is preferred that the angle is no more than 50° up or down from the position which is perpendicular to the direction of the incoming aqueous polyacrylamide gel. Preferably this angle should be from 5° to 45°, more preferably from 10° to 35°, particularly from 15° to 25°.

In a further embodiment of the invention, the at least one rotating nozzle or rotating head is not mounted centrally but off center. For instance, where the cutting stage is contained in a surrounding wall section the rotating nozzle may be located at or close to the wall of the surrounding wall section. Typically, the nozzle or head would be orientated such that it generates at least one eccentric aqueous stream sweep pattern.

The rotating nozzle or rotating head may rotate at a frequency of up to 3000 rpm (revolutions per minute (i.e. 50 $s^{-1}$ cycles per second)). The rotational frequency may be selected by the skilled artisan. A higher rotational frequency, for example a rotational frequency from 500 rpm to 1000 rpm) may by trend tear the aqueous polyacrylamide gel into smaller parts while a smaller rotational frequency, for example from 10 rpm to less than 500 ppm, preferably 20 rpm to 200 rpm more properly cuts the aqueous polyacrylamide gel. In certain embodiments of the invention, the rotational frequency may be from 10 to 500 rpm, for example from 20 to 200 rpm.

Desirably, the water-jet cutting unit will divide the aqueous polyacrylamide gel into numerous smaller sized pieces. The aqueous polyacrylamide gel pieces should conveniently have a size such that at least two dimensions are no more than 2 cm, preferably no more than 1 cm, more preferably no more than 0.5 cm. Preferably three dimensions of the aqueous polyacrylamide gel pieces should be no more than 2 cm, preferably no more than 1 cm, preferably no more than 0.5 cm. There is no lower limit necessary for the aqueous polyacrylamide gel pieces, since the smaller the pieces the easier it will be for the polymer to dissolve. In one embodiment, the aqueous polyacrylamide gel pieces have three dimensions each of from 0.1 to 0.5 cm.

The water-jet cutting unit may also comprise a sieve tray beneath the at least one stream of aqueous liquid. This is intended to prevent oversized aqueous polyacrylamide gel lumps from passing into the next stage. The sieve tray should have openings of a size corresponding to the maximum size of aqueous polyacrylamide gel pieces which should be allowed to pass to the next stage. Suitably the sieve tray may be a mesh formed by a plurality of inter-meshing wires or bars. Alternatively, the sieve tray may be formed as a surface with a plurality of holes cut therein, for instance, analogous to a colander. Typically, the sieve tray should be a static device. It should extend to cover the whole area below where the aqueous polyacrylamide gel cutting is taking place. Preferably, the sieve tray may be affixed to the surrounding wall section. In embodiments of the present invention additional streams of aqueous liquid are directed at the surface of the sieve tray in order to facilitate the size reduction of the oversized aqueous polyacrylamide gel lumps captured by the tray. It may be desirable to employ one or more aqueous liquid streams of high-pressure, for instance, of at least $150*10^5$ Pa in order to facilitate the cutting of the oversized aqueous polyacrylamide gel lumps such that the aqueous polyacrylamide gel is cut into small enough pieces to pass through.

Desirably, a curtain of aqueous liquid is provided on the inside of the surrounding wall section. This curtain of aqueous liquid may help prevent aqueous polyacrylamide gel from sticking to the wall of the surrounding wall section and reduce friction of the moving polymer thereby reducing necessary static pressure or avoiding additional mechanical means to move the polymer towards the cutting area. Such curtain of aqueous liquid may be produced by providing a secondary aqueous liquid supply. Typically, the pressure of the aqueous liquid should be below 30 bar, for instance, from 3 bar to 20 bar, desirably from 5 bar to 10 bar. The water may be fed to a ring main, in the form of an annulus, and mounted on the inside of the surrounding wall section. In order to be most effective, the ring main or annulus should be mounted at or close to the top of the surrounding wall section to provide the maximum protection by the curtain of water. Desirably the aqueous liquid flows from the ring main or annulus down the inner surface of the wall of the surrounding wall section as a curtain.

FIGS. 7 to 10 represent schematically several embodiments of a water-jet cutting unit for use in the present invention.

FIG. 7 illustrates schematically a water-jet cutting unit for cutting the aqueous polyacrylamide gel. The device comprises a surrounding wall section (101), in this case a tubular wall, surrounding a centrally mounted nozzle (102) which rotates and is driven by a motor (103) or propelled by the flowing aqueous liquid, which forms the stream. The nozzle is supported on a fixed mounting (104). A high-pressure stream of aqueous liquid (105) is ejected perpendicular to the axis of the device and rotates as the nozzle rotates. The stream of aqueous liquid forms a circular disc pattern as the nozzle rotates. The nozzle is fed from a aqueous liquid feed line (106) supplied by a high pressure aqueous liquid source (107). A sieve tray (108) is located beneath the stream of water and prevents oversized polymer lumps from passing. A secondary aqueous liquid supply (109) of low pressure is fed into a ring main (110), in the form of an annulus, located at the upper end of the tubular wall. Aqueous liquid flows out of the annulus to form a water curtain (111), which prevents aqueous polyacrylamide gel from sticking to the tubular wall. Aqueous polyacrylamide gel (113) enters the tubular wall from above and passes down the device where it is cut by the high-pressure water stream to form cut hydrated polymer pieces which are small enough to pass through the sieve tray and then the cut aqueous polyacrylamide gel pieces (114) exit from the bottom of the device.

FIG. 8 illustrates a device analogous to the device of FIG. 7 except the nozzle (102) provides a high-pressure stream of water which is angled downwards (105A) to form a conical pattern as the nozzle rotates. The sieve tray is in the shape of an upright cone (108A). All other features are as in the case of FIG. 7.

FIG. 9 illustrates a device analogous to the device of FIG. 8 except the nozzle (102) provides a high-pressure stream of water which is angled upwards (105B) to form a conical pattern as the nozzle rotates. The sieve tray is in the shape of an inverted cone (108B). All other features are as in the case of FIG. 7.

FIG. 10 illustrates a device analogous to the device of FIG. 7 except the nozzle (102) is positioned off center to provide an eccentric high-pressure water stream (105) sweep pattern. All other features are as in the case of FIG. 7.

Combinations

The described methods of comminuting the aqueous polyacrylamide gel may also combined with each other.

In one embodiment of the invention, water-jet cutting is combined with cutting by means of a static cutting member. Preferably, such a static cutting member is integrated with the water-jet cutting unit and consequently, the water-jet cutting comprises at least one static cutting member. The at least one static cutting member may for instance be one or more knives, blades, cutting wires or any combination thereof. In one embodiment, the at least one cutting member may consist of a multiplicity of knives or blades mounted on the wall of the tubular section circumferentially with the knives or blades extending inwardly. In another embodiment, the at least one cutting member may be knives or blades mounted from a central position with the knives or blades extending out radially. In a further form the at least one cutting member may be a mesh of knives, blades or cutting wires. Typically, the static cutting member, where employed, should extend over the whole cross-section of the surrounding wall section. Suitably, the aqueous polyacrylamide gel may be cut by contacting the at least one static cutting member before contacting the at least one stream of aqueous liquid.

FIG. 11 illustrates schematically a water-jet cutting unit combined with static cutting means. The device comprises a surrounding wall section (101), in this case a tubular wall, into which the aqueous polyacrylamide gel (113) enters from the top. A mesh of cutting blades (112) initially cuts the hydrated polymer into strands as it descends. High-pressure water streams (105) are ejected from nozzles (102) that are positioned circumferentially. The nozzles each oscillate laterally to each generate a fan shaped water stream sweep pattern (115) which cut the polymer strands as they descend. The oscillation of the nozzles is driven by an actuator (not shown) in each case. The aqueous polyacrylamide pieces (114) exit through the bottom of the device.

In another embodiment, water-jet cutting may be combined with static mixing. For that purpose, the aqueous mixture comprising pieces of polyacrylamide gel leaving the water-jet cutting unit is conveyed through at least one static mixer. Additional aqueous liquid may be added to the mixture, before it enters into the at least one static mixer.

In another embodiment, water-jet cutting is combined with both, static cutting means and a static mixer. The combination with static cutting means has already been described above. Thereafter, the aqueous mixture comprising pieces of polyacrylamide gel leaving the comminution unit comprising a water-jet cutting step and a static cutting step is conveyed through at least one static mixer. Additional aqueous liquid may be added to the mixture, before it enters into the at least one static mixer.

In one embodiment, comminuting the aqueous polyacrylamide gel is carried out by at least one means selected from rotating water-jets, rotating knives or and a hole perforation plate. Preferably, a combination of at least a hole perforation plate and rotating water-jets or at least a hole perforation plate and rotating knives may be used.

In other embodiments, the comminution unit comprises a combination of water-jet cutting and a hole perforation plate. The hole perforation plate comprises holes. The shape of the holes is not specifically limited. Examples comprise circular holes, ellipsoidal holes, triangular holes, quadrangular holes such as quadratic, rectangular, or rhombic holes, pentagonal holes, hexagonal holes or star-like holes but also longitudinal holes such as slots. The holes may be cylindrical but they may also be conical.

The dimensions of the holes are not specifically limited. However, preferably at least one dimension of the holes should be from 0.5 to 5 mm. In one embodiment of the invention, the hole perforation plate comprises circular holes having a diameter from 0.5 to 5 mm, for example from 1 mm to 3 mm.

The aqueous polyacrylamide is conveyed from the polymerization unit through the hole perforation plate. One or more rotating nozzles for water-jets are mounted above or below the hole perforation plate.

One embodiment of such a combination is schematically shown in FIG. 12. FIG. 12 schematically shows a polymerization unit having an upper cylindrical part (120), a lower conical part (121) and a bottom opening (125) which may be opened and closed. The polymerization unit is connected with a comminution unit comprising a hole perforation plate. One rotating nozzle for water-jets is mounted below the hole perforation plate. The aqueous polyacrylamide gel is removed from the polymerization unit by opening the bottom opening (125) and applying pressure onto the upper surface of the aqueous polyacrylamide gel. The gel is conveyed through the opened bottom opening and the hole perforation plate. The hole perforation plate generates strings of aqueous polyacrylamide gel ("spaghetti") which are cut into small pieces by the water-jets.

Figure 1:
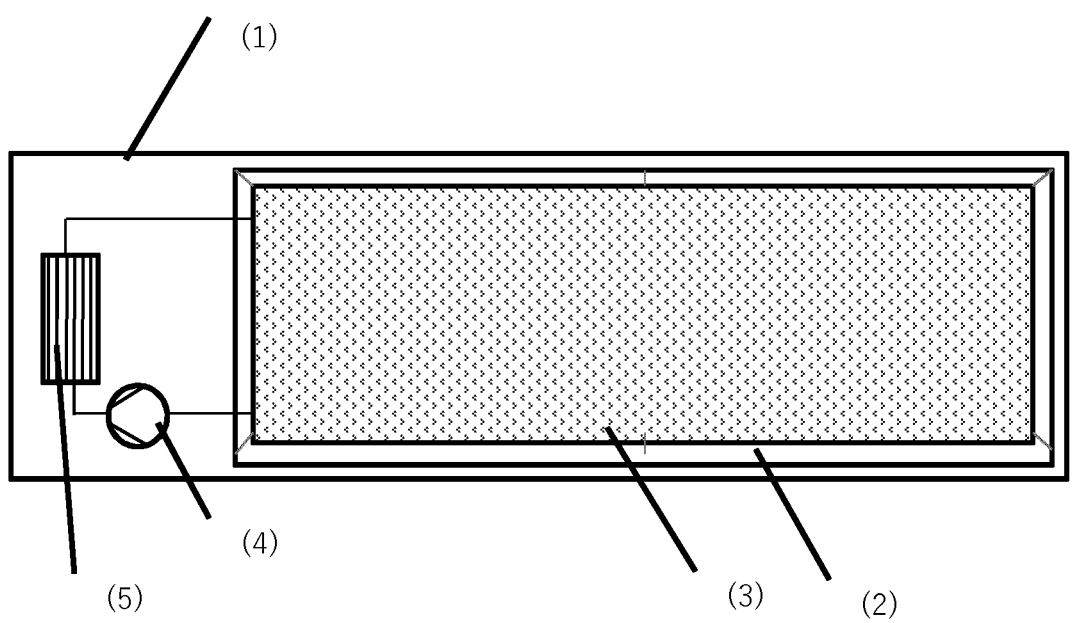
Figure 2:
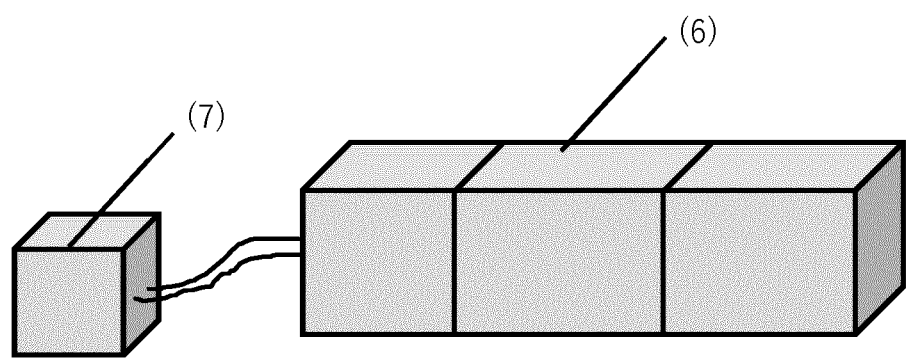
Figure 3:
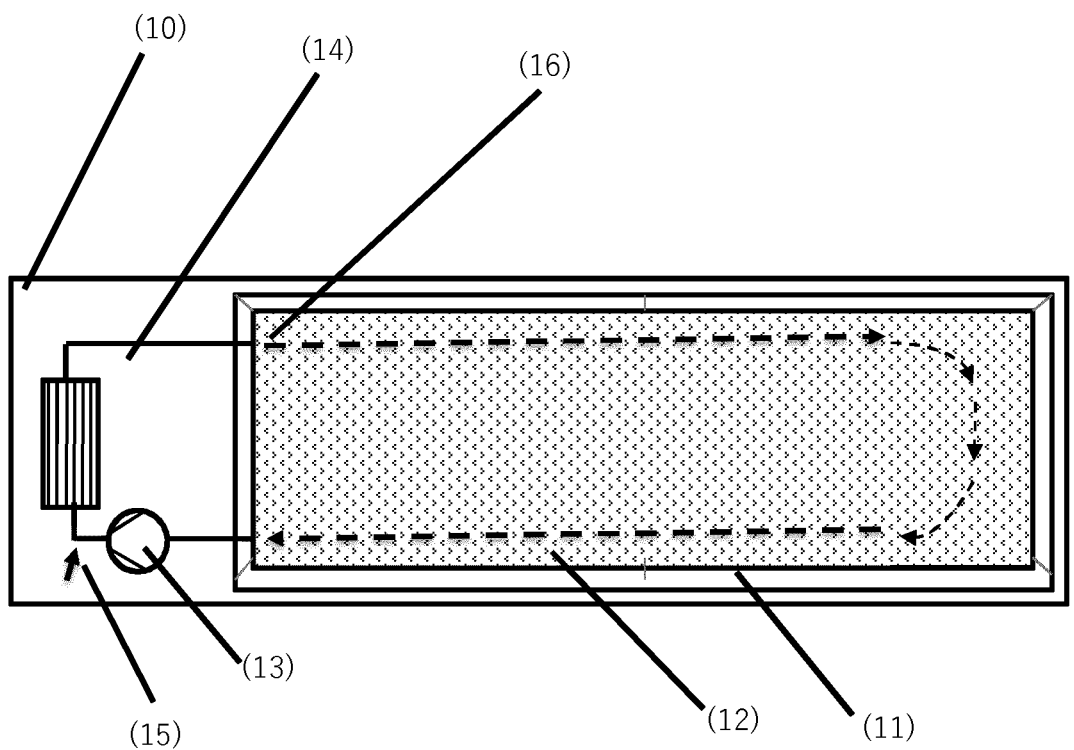
Figure 4:
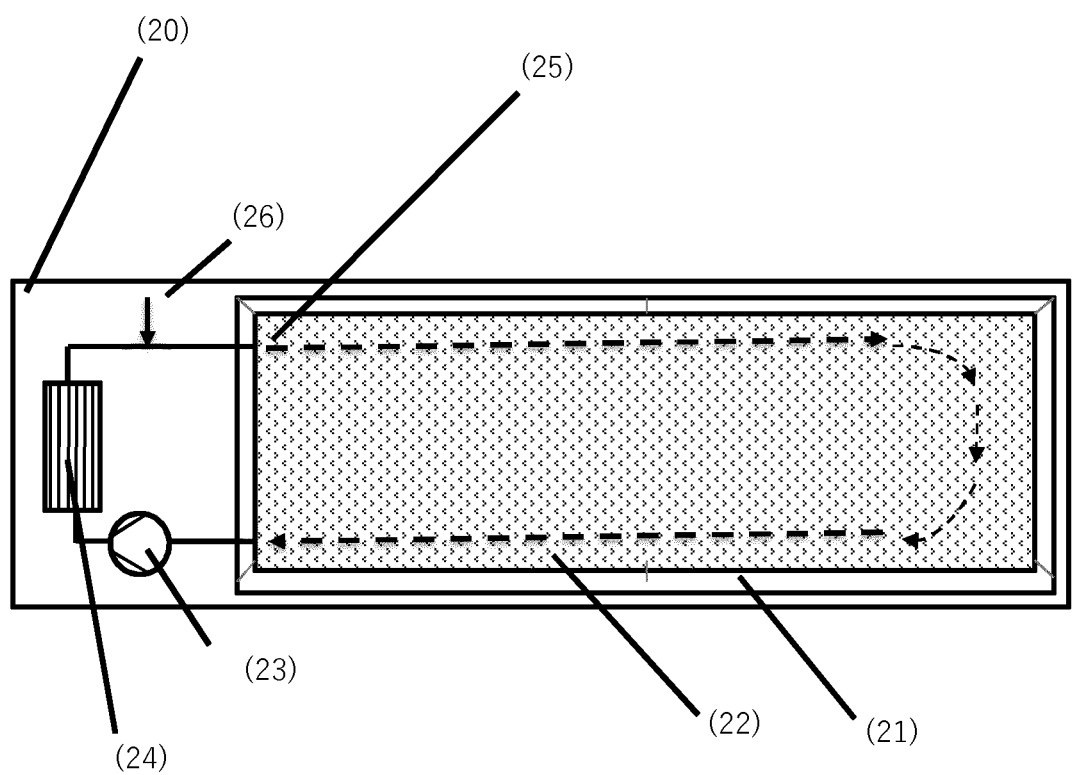
Figure 5:
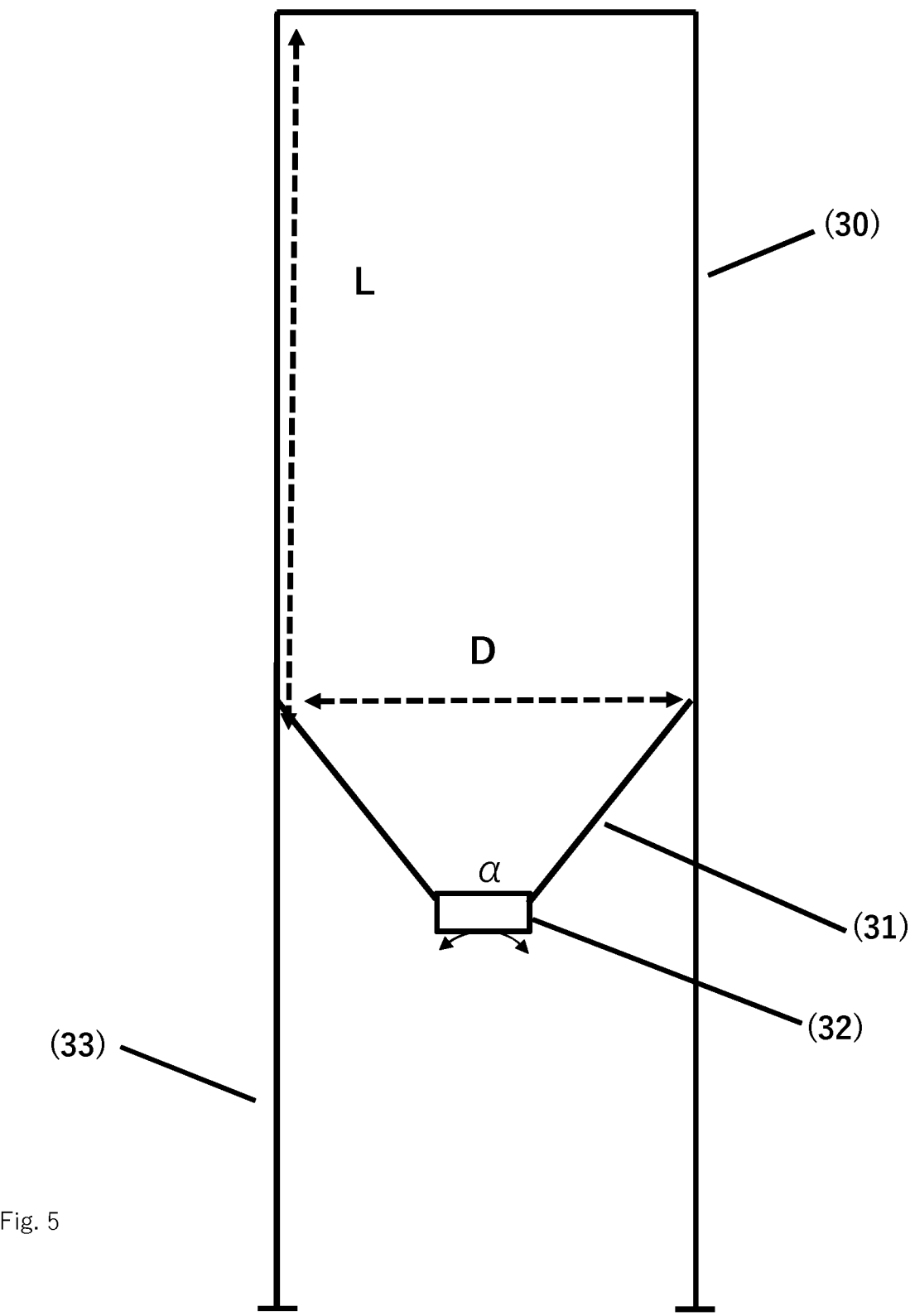
Figure 6:
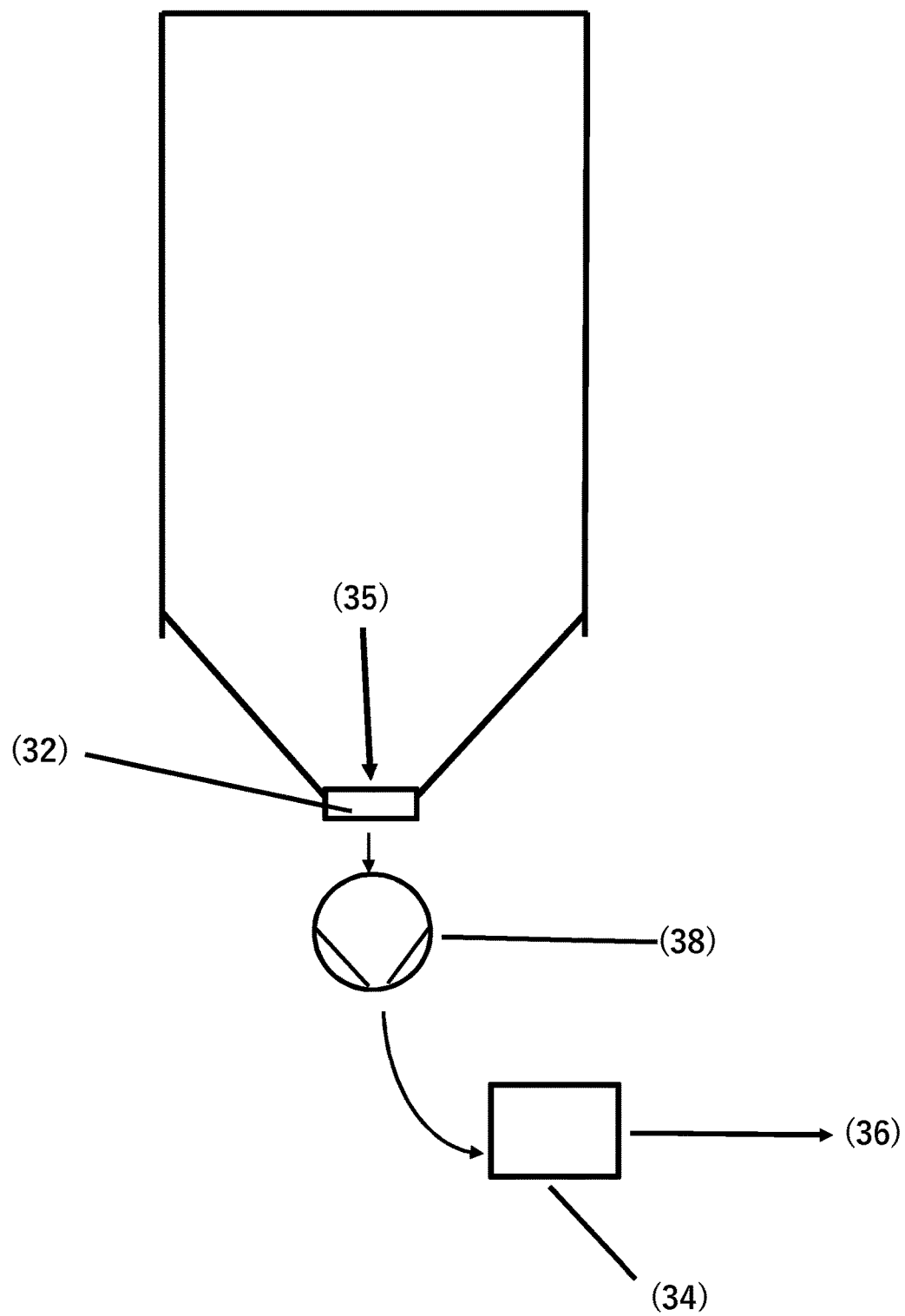
Figure 7:
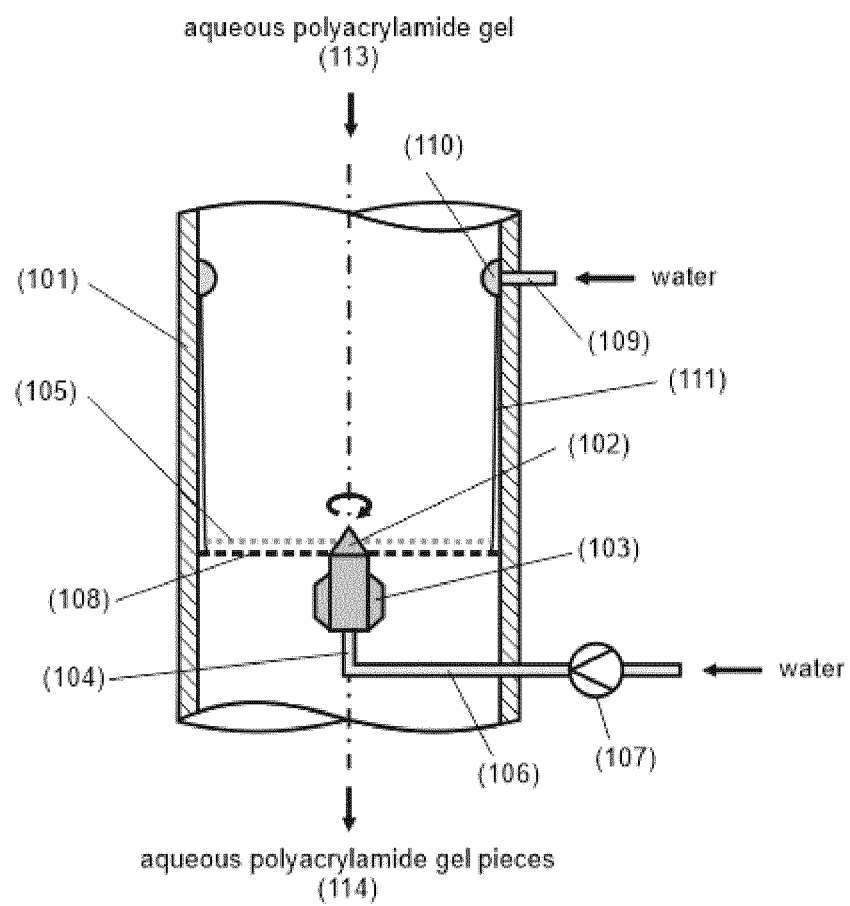
Figure 9:
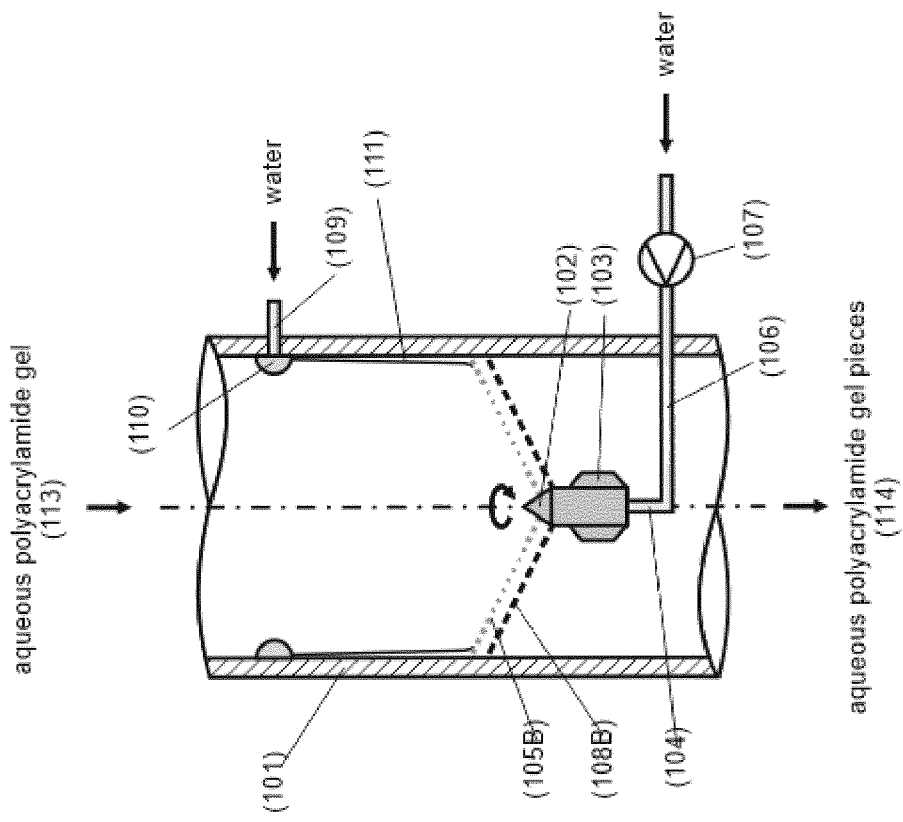
Figure 8:
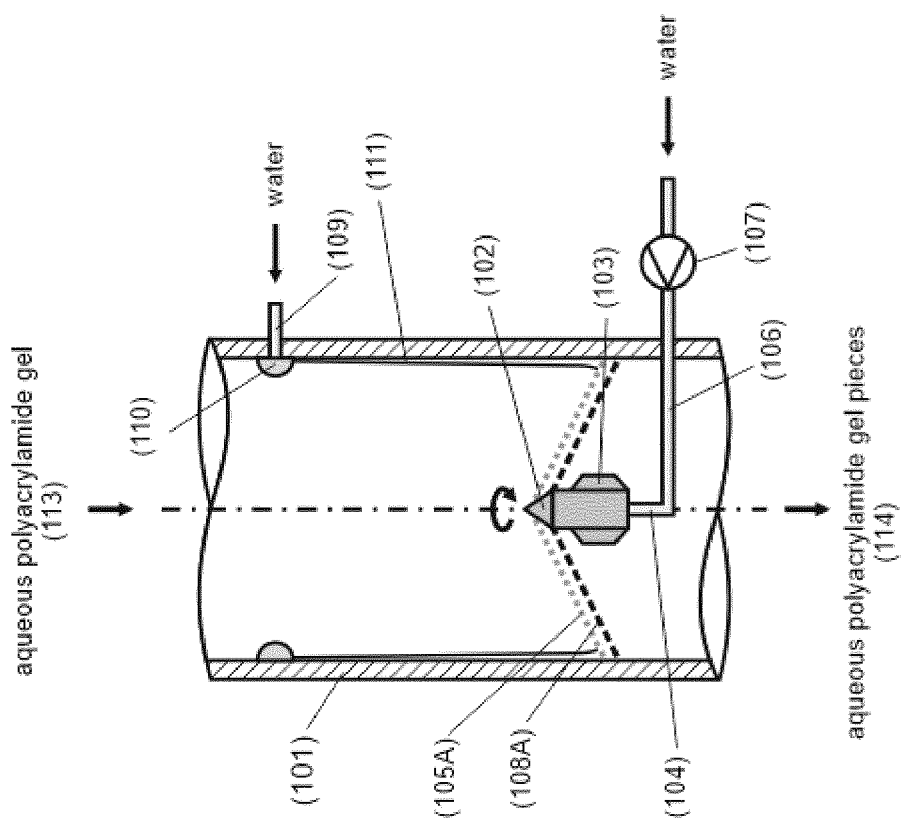
Figure 10:
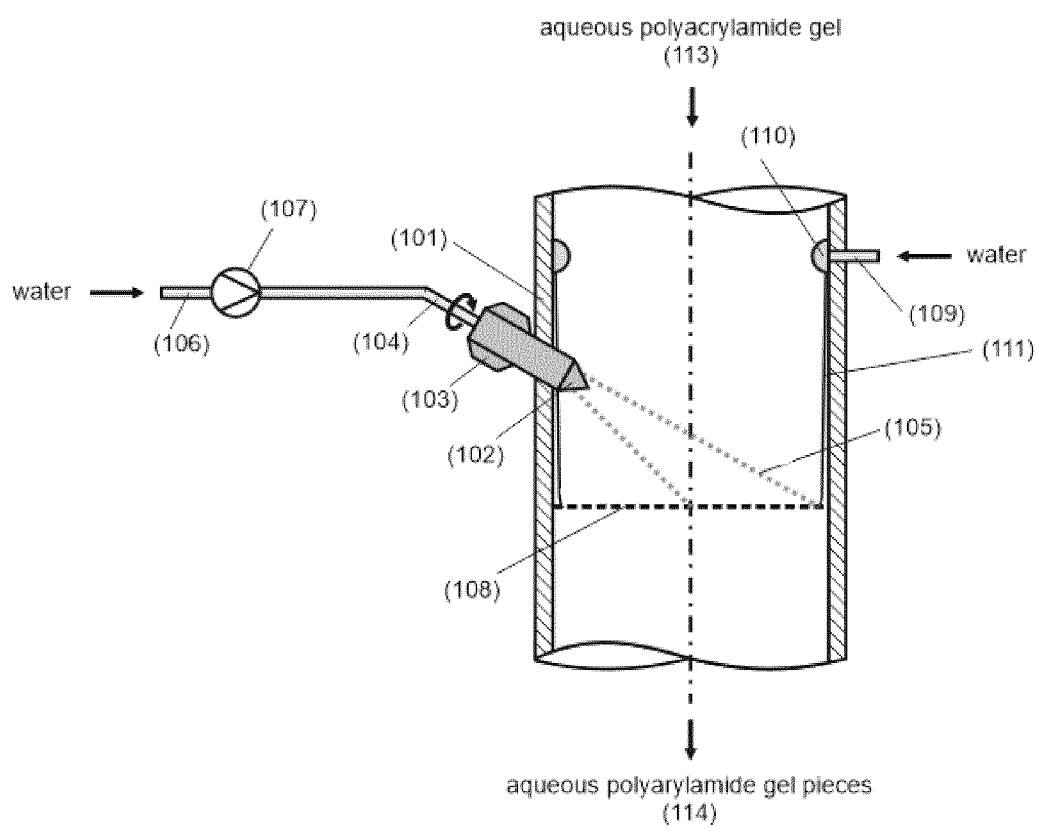
Figure 11:
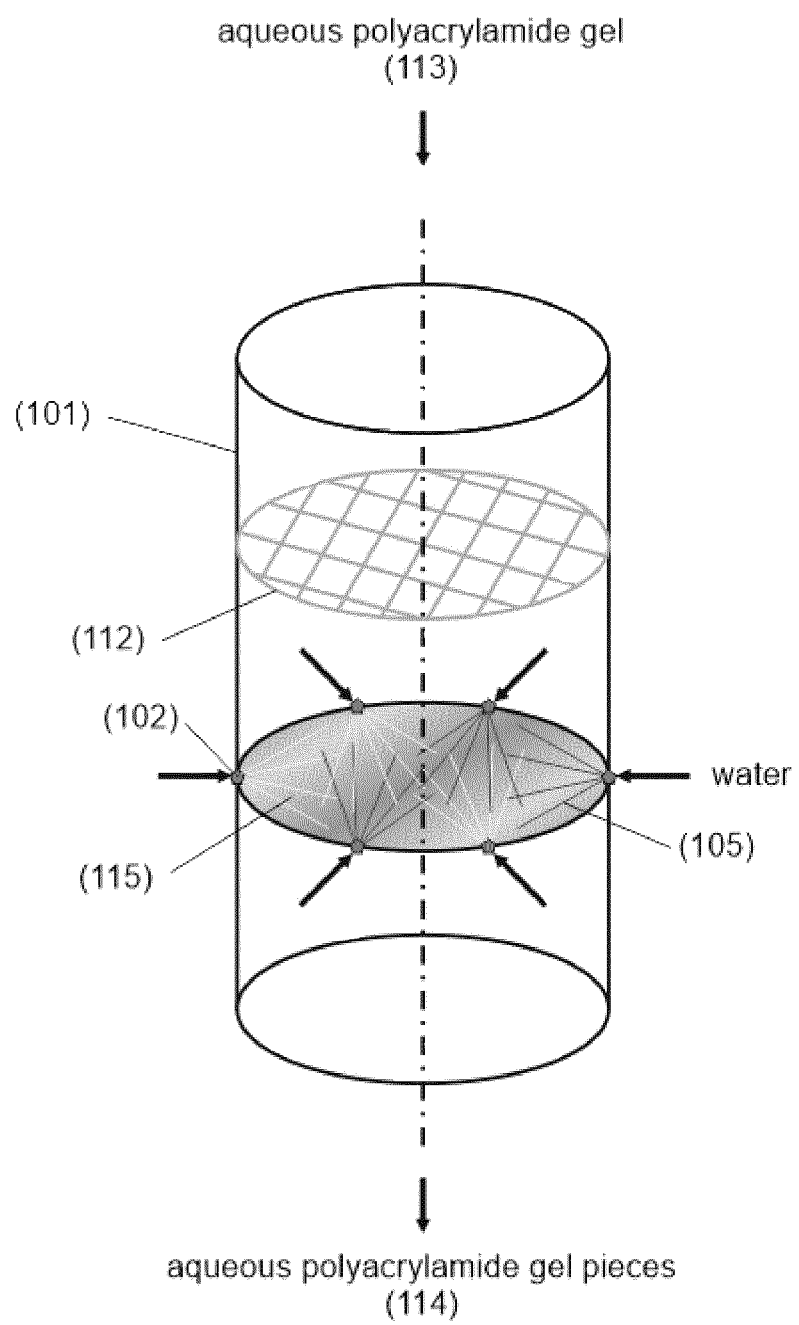
Figure 13:
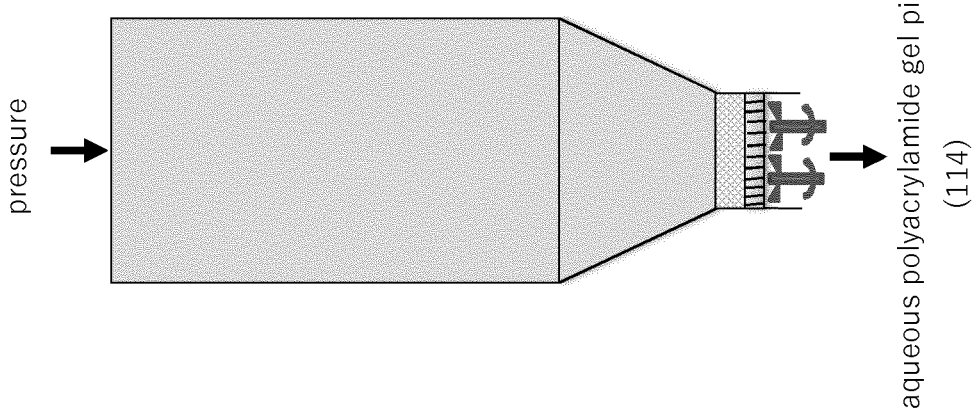
FIG. 13 shows a similar embodiment except that not one two nozzles are mounted below the hole perforation plate. Of course, also more than two nozzles may be used, for example 4 nozzles.
Figure 12:
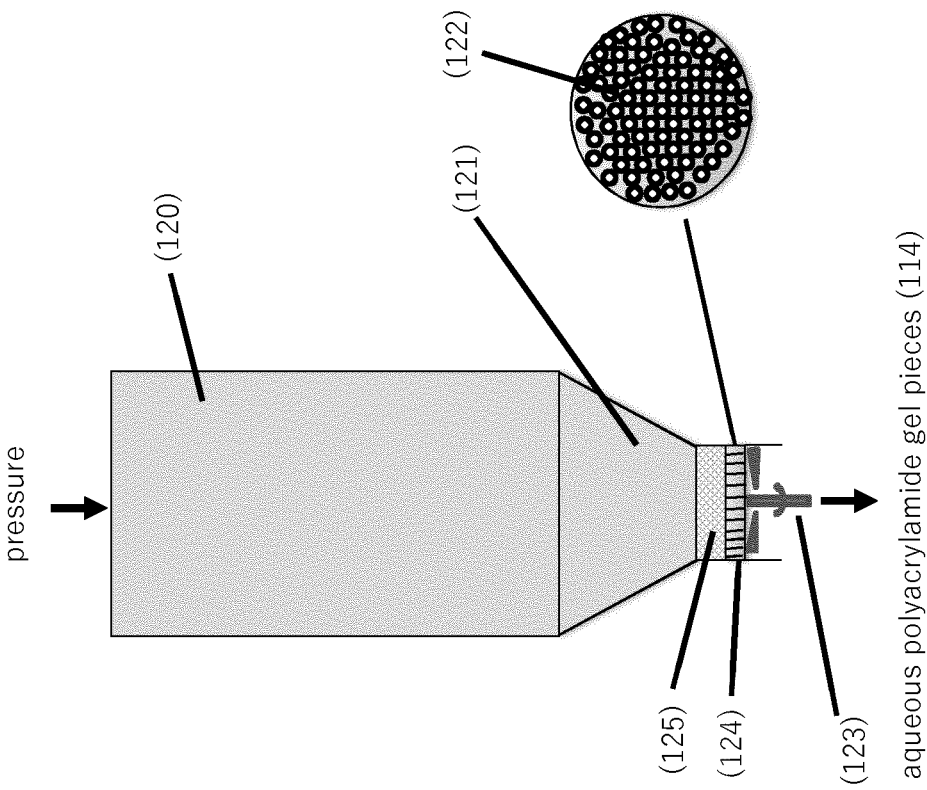
Figure 15:
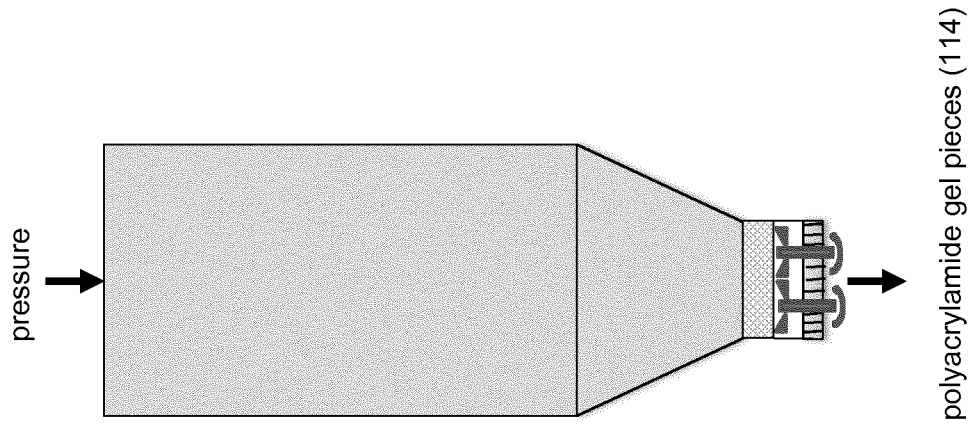
FIGS. 14 and 15 show similar embodiments in which the nozzle(s) for water-jets are mounted above and not below the hole perforation plate.
Figure 14:
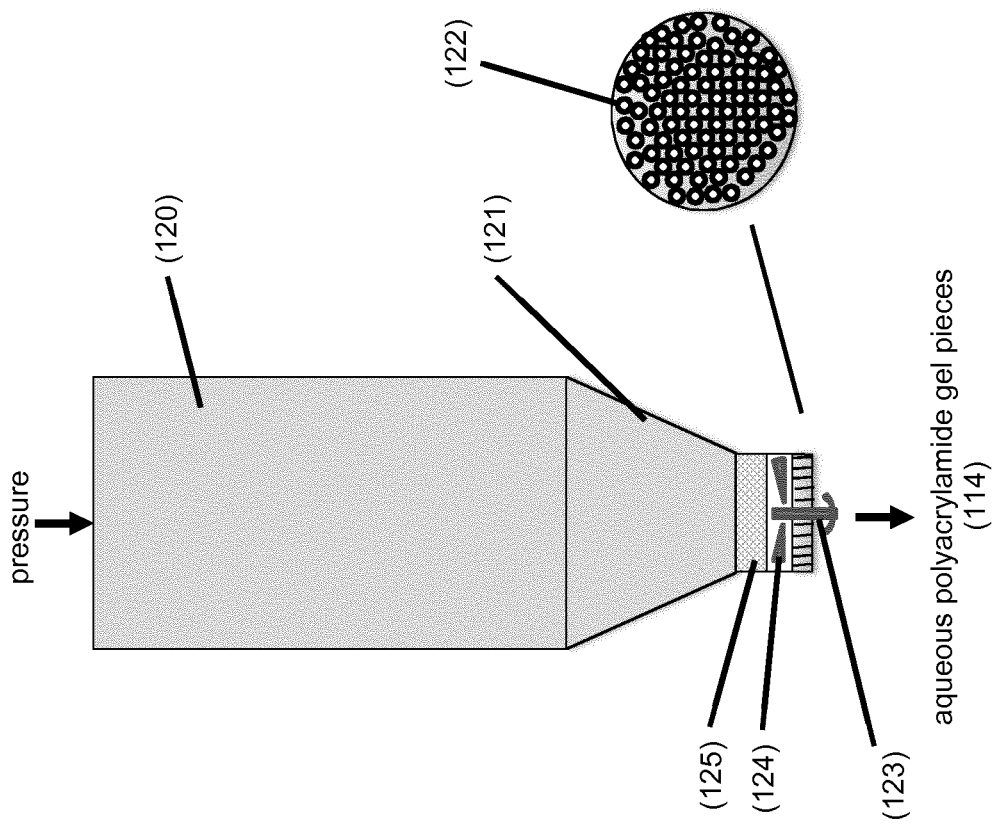
Figure 16:
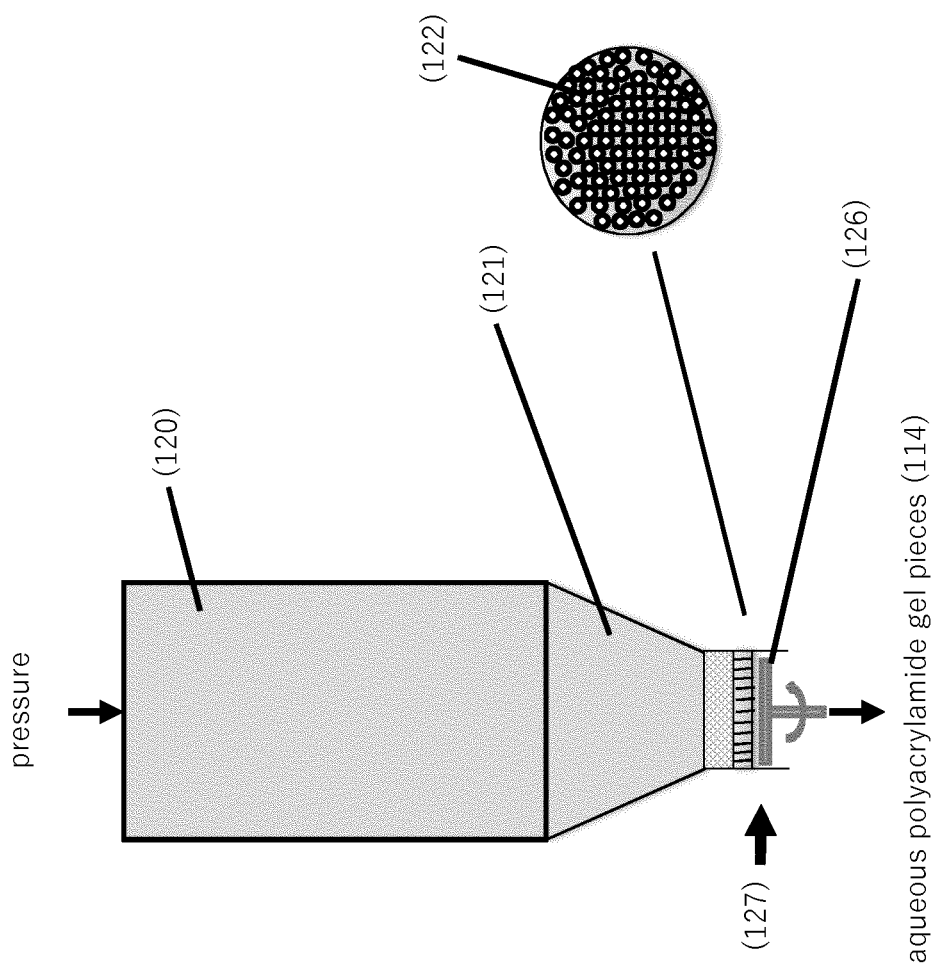

FIG. 16 shows an alternative embodiment comprising a rotating knife mounted below the hole perforation plate for cutting. Its function is the same a detailed above (FIGS. 12 and 13), except that a mechanical knife and not water-jets are used for cutting the strings of polyacrylamide gel. In this embodiment, water (127) is added into the cutting space below the hole perforation plate. The water may be added through one or more than one water inlets. The entire amount of water to achieve the desired concentration or only a part of it may be added.

As shown above, preferably at least a part of the aqueous liquid necessary to obtain the desired concentration is already added in course of comminution. In other embodiments, already the entire amount may be added. So typically, the comminution yields a mixture of polyacrylamide gel particles and aqueous liquid. It goes without saying, that at least a part of the polyacrylamide gel already dissolves in the aqueous liquid in course of comminution, so the mixture may perhaps be better characterized as polyacrylamide gel particles in an aqueous solution of polyacrylamides. The degree of homogeneity depends on the chosen comminution technology and the added amount of water in this process step.

Homogenization

Optionally, comminution and mixing the aqueous polyacrylamide gel particles with an aqueous liquid may be followed by a homogenization step. If not already done, any remaining amount of aqueous liquid to achieve the desired concentration of the aqueous polyacrylamide concentrate—if any—is added before or in course of such a homogenization step.

In one embodiment of the invention, the obtained mixture of an aqueous polyacrylamide solution and undissolved polyacrylamide gel pieces may be simply allowed to stand in a suitable vessel in order to homogenize. The vessel may be located at location A and after homogenization the homogenized aqueous polyacrylamide concentrate is transferred to the transport unit for carrying out step [4] as will be described later. In another embodiment of the invention, the mixture obtained in course of comminution may already be filled into the transport unit. Advantageously, in this embodiment, the transport time may be used for homogenization.

In other embodiments, homogenization is carried out by mixing the obtained mixture using suitable means. Mixing may in particular be carried out by transferring the obtained mixture to a vessel located at location A and mixing the contents of the vessel thereby obtaining the homogenized aqueous polyacrylamide concentrate.

If the aqueous polyacrylamide concentrate has a viscosity which is not too high, stirring of the mixture may still be possible. Other embodiments include the use of static mixers. In one embodiment, the mixture in the mixing vessel may be circulated using circulation pumps. Optionally, the loop may comprise one or more static mixers. Further examples include tumbling, shaking or any mixing method known to skilled in the art for highly viscous liquids, for example using progressive cavity pumps.

If a vessel is used for homogenization, said vessel may also serve as temporary storage unit before transporting the aqueous polyacrylamide concentrate to location B in course of step [4].

Step [4] Transport of the Aqueous Polyacrylamide Concentrate

In course of step [4], the aqueous polyacrylamide concentrate is transported from location A to location B.

For transport, a suitable transport unit is used. The transport unit may have a volume from 1 m$^3$ to 40 m$^3$, in particular 5 m$^3$ to 40 m$^3$, preferably 10 to 30 m$^2$, for example 20 m$^3$ to 30 m$^3$ or from 15 to 25 m$^3$. Examples of suitable transport units comprise vessels comprising at least one opening, tank containers, or tipping vessels.

The transport may be carried out by any kind of transport means suitable for transporting the transport unit, for example by trucks, railcars or ships.

The term "transport unit" shall include separate transport units such as vessels, containers, for example ISO containers or intermediate bulk containers, which are loaded on suitable transport means for transport, for example on trailers, container cars or ships. The transport means may transport one single transport unit or a plurality of transport units. The term "transport unit" furthermore includes transport units in which the transport compartment is permanently fixed on the transport means, such as for example tank trucks or tanks cars.

In one embodiment, the transport is carried out by trucks. The transport unit may also be fixed on a truck. In one embodiment, the transport unit may be an ISO tank container. Typical dimensions of ISO containers have already been mentioned above.

In another embodiment, tanks fixed on a truck may be used. In one embodiment, the tank comprises an outlet opening at the rear end of the truck and for supporting removal of the contents the tank may be tilted. In another embodiment, the tank comprises an outlet opening at the bottom side of the tank. Additionally, the tank may comprise a conus at the bottom side of the tank and the outlet opening in located at the lower end of the conus. The tank may also be rotatable, so that the concentrate may become homogenized in course of transport. For example, a concrete mixer may be used for transporting the concentrate.

Filling the transport unit with the aqueous polyacrylamide concentrate may be carried out by pumping the concentrate into the transport unit.

The transport time, i.e. the time for transporting the transport unit filled with aqueous polyacrylamide concentrate may be very different, depending on the distance between the locations A and B. It may range from minutes to several days, for example from 1 h to 28 days, in particular from 2 hours to 14 days, in particular 5 hours to 7 days.

In one embodiment of the invention, a homogenization step as described above may be carried out in course of transport. In one embodiment, the transport unit, for example a truck may comprise a rotating drum thereby effecting homogenization. Trucks comprising rotating drums are known on the art for transporting concrete. In other embodiments, the transport unit may comprise a circulation loop equipped with a pump and optionally mixing units, for example static mixers, so that the aqueous polyacrylamide concentrate can be circulated in course of transport.

Step [5] Removal of the Aqueous Polyacrylamide Concentrate from the Transport Unit In course of step [5] the aqueous polyacrylamide concentrate is removed from the transport unit. Step [5] is carried out at location B.

Basically, removing the aqueous polyacrylamide concentrate may be carried out by any kind of technology. The details depend on the specific design of the transport unit, the kind of concentrate, in particular its viscosity, and the connected downstream processing equipment.

Preferably, the aqueous polyacrylamide concentrate may be removed by means of a pump. Removal may be supported by applying pressure onto the transport unit, in particular by means of gas pressure. Furthermore, removal may also be supported—depending on the construction of the transport units—by tilting the transport unit.

After removal form the transport unit, the aqueous polyacrylamide concentrate may be directly used. In other embodiments, the aqueous polyacrylamide concentrate is transferred into suitable storage units, for example storage tanks for temporarily storing it before use.

Further Steps

Basically, it is possible to use the aqueous polyacrylamide concentrate as such, i.e. it is transferred directly from the transport unit or from a storage unit to the application where it is used. Examples of applications in which concentrates may be used directly, will be mentioned below. The transfer of the aqueous polyacrylamide concentrate may be affected by means of piping or other suitable conduit.

In another embodiment, the aqueous polyacrylamide concentrate may be further diluted for application using an aqueous liquid as defined above. As already outlined above, a composition resulting from such additional dilution step shall be referred to as "aqueous polyacrylamide solution".

Basically, an additional dilution step may be carried out in any kind of dilution device. In one embodiment, a dilution of the aqueous polyacrylamide concentrate is conducted in a relocatable dissolution unit. For an additional dilution step, the aqueous polyacrylamide concentrate may be pumped into the dilution unit. In course of dilution, the aqueous polyacrylamide concentrate may optionally be mixed with further components. The skilled artisan may choose such further components according to his/her needs.

Examples of dilution devices comprise static mixers, combination of static mixers with further mixing equipment such as a combination of static mixers with unstirred vessels or in-line dispersing such as rotor-stator units.

Further examples of suitable dilution units comprise stirred vessels. A dilution unit may only comprise one vessel or it may comprise more than one vessel which may be operated in series or in parallel. Examples of means for mixing comprise one or more impellers or stirrers which optionally may be combined with static mixing devices. Mixing may also be achieved by flowing the contents of the dissolution vessel out through a conduit and then recirculating back into the mixing tank.

In one embodiment of the invention, an aqueous polyacrylamide concentrate having a concentration of 3.1% to 10% by weight, preferably from 3.1 to 7% by weight is transported from location A to location B and diluted with aqueous fluid at location B thereby obtaining an aqueous polyacrylamide solution having a concentration from 0.01% to 2.0% by weight, preferably from 0.1% to 1.0% by weight.

In one embodiment, the aqueous polyacrylamide concentrates may be used directly at the location B, i.e. at the location where it is removed from the transport unit. In other embodiments, the aqueous polyacrylamide concentrate, preferably a concentrate having a concentration of not more than 7% by weight, for example from 3.1 to 7% by weight or an aqueous polyacrylamide as described above solution may be distributed to a further location C, preferably a plurality of further locations C by pipelines.

Modification of the Polyacrylamides

In one embodiment of the invention, the polyacrylamides may simultaneously be modified in course of step [4] and/or in course of an additional dilution step.

For that purpose, suitable agents for modifying the polymers may be added to the aqueous liquid used for mixing with the aqueous polyacrylamide gel and/or used for an additional step of dilution. In other embodiments, such agents may be added separately, preferably as aqueous solution.

In one embodiment of the invention, the polyacrylamides may be partially hydrolyzed thereby obtaining polyacrylamides comprising also —COOH groups or salts thereof. In certain embodiments, about 30 mol % of the amide groups may be hydrolyzed to carboxylic groups. Partially hydrolyzed polyacrylamides are known in the art. For that purpose, bases such as NaOH are added to the aqueous liquid.

In another embodiment, hydroxylamine and a base may be added to the aqueous liquid thereby obtaining polyacrylamides in which a part of the amide groups are converted to hydroxamic acid groups.

Further Embodiments of the Process

In one embodiment, the present invention relates to a process for producing an aqueous polyacrylamide concentrate by polymerizing an aqueous solution comprising at least acrylamide thereby obtaining an aqueous polyacrylamide gel and mixing said aqueous polyacrylamide gel with an aqueous liquid, wherein the process comprises at least the following steps:

[1] radically polymerizing an aqueous monomer solution in the presence of suitable initiators for radical polymerization under adiabatic conditions in a polymerization unit at a location A, wherein the aqueous monomer solution comprises at least water and 15% to 50% by weight—relating to the total of all components of the aqueous monomer solution—of water-soluble, monoethylenically unsaturated monomers at a location A, wherein said water-soluble, monoethylenically unsaturated monomers comprise at least acrylamide, wherein the polymerization unit comprises a cylindrical upper part, a conical part at its lower end, feeds for the aqueous monomer solution and a bottom opening, thereby obtaining an aqueous polyacrylamide gel which is hold in the polymerization unit,

[2] removing the aqueous polyacrylamide gel from the polymerization unit through the bottom opening by means of gas pressure at the location A,

[3] comminuting the aqueous polyacrylamide gel and mixing it with an aqueous liquid at the location A, thereby obtaining an aqueous polyacrylamide concentrate having a concentration of 1.0 to 14.9% by weight of polyacrylamides, relating to the total of all components of the aqueous polyacrylamide concentrate,

[4] transporting the aqueous polyacrylamide concentrate in a transport unit having a volume form 1 m³ to 40 m³ by transport means selected from the group of trucks, railcars or ships from location A to a different location B, and

[5] removing the aqueous polyacrylamide concentrate from the transport unit at the location B.

Preferred embodiments have already been disclosed above and we refer to the relevant passages of the specification.

In another embodiment, the present invention relates to a process for producing an aqueous polyacrylamide concentrate by polymerizing an aqueous solution comprising at least acrylamide thereby obtaining an aqueous polyacrylamide gel and mixing said aqueous polyacrylamide gel with an aqueous liquid, characterized in that the process comprises at least the following steps:

[1] Radically polymerizing an aqueous monomer solution in the presence of suitable initiators for radical polymerization under adiabatic conditions in a polymerization unit, wherein the aqueous monomer solution comprises at least water and 15% to 50% by weight—relating to the total of all components of the aqueous monomer solution—of water-soluble, monoethylenically unsaturated monomers, wherein said water-soluble, monoethylenically unsaturated monomers comprise at least acrylamide, wherein the polymerization unit comprises a cylindrical upper part, a conical part at its lower end, feeds for the aqueous monomer solution and a bottom opening, thereby obtaining an aqueous polyacrylamide gel which is hold in the polymerization unit,

[2] removing the aqueous polyacrylamide gel from the polymerization unit through the bottom opening by means of gas pressure,

[3] conveying the aqueous polyacrylamide gel through at least one comminution unit together with an aqueous liquid thereby yielding a mixture of pieces of aqueous polyacrylamide gel in an aqueous polyacrylamide solution followed by homogenization of the mixture obtained by transferring the mixture to a vessel and allowing the mixture to stand in the vessel, mixing the contents of the vessel by suitable mixing means, thereby obtaining an aqueous polyacrylamide concentrate having a concentration of 3.1 to 14.9% by weight of polyacrylamides, relating to the total of all components of the aqueous polyacrylamide concentrate.

Said embodiment relates to the process steps performed at location A. The parameters of this embodiment, including preferred parameters, and suitable equipment for carrying out the steps, including preferred equipment, have already been described in detail above, and we explicitly refer to the relevant passages of the specification above.

Measurement and Control

In one embodiment, Locations A and B each comprise a central process measuring and control technology unit. In a preferred embodiment of the invention, the process measuring and control technology unit is a relocatable unit. Preferably, the process measuring and control technology unit at location A is connected with all units at location A and also preferably, the process measuring and control technology unit at location B is connected with all units at location B, thereby enabling a central process control similar to fixed plants. In one embodiment, all connections with measuring and control instruments of a certain unit, e.g. the dissolution unit, the monomer storage units or the polymerization units are bundled in one cable, for example BUS technology, so that they may be easily plugged together. Of course, also other connecting technologies are possible, for example radio links.

Modular, Relocatable Plant

In another embodiment, the present invention relates to a modular, relocatable plant for manufacturing aqueous polyacrylamide concentrates by polymerizing an aqueous solution comprising at least acrylamide thereby obtaining an aqueous polyacrylamide gel and mixing said aqueous polyacrylamide gel with an aqueous liquid, comprising at least at a location A a relocatable storage unit for an aqueous acrylamide solution, optionally relocatable storage units for water-soluble, monoethylenically unsaturated monomers different from acrylamide, a relocatable storage unit for polymerization initiators, a relocatable monomer make-up unit for preparing an aqueous monomer solution comprising at least water and acrylamide, a relocatable polymerization unit for polymerizing the aqueous monomer solution in the presence of polymerization initiators, a relocatable unit for comminution of the aqueous polyacrylamide gel and mixing it with an aqueous liquid thereby obtaining an aqueous polyacrylamide concentrate, at locations A or B a transport unit for transporting an aqueous polyacrylamide concentrate from location A to location B.

at a location B means for removing the aqueous polyacrylamide concentrate from the transport unit, and optionally means for further diluting the aqueous polyacrylamide concentrate with a aqueous liquid.

In one embodiment, the distance between locations A and B is from 1 to 3000 km, in particular from 10 km to 3000 km, for example from 10 to 1500 km or from 20 km to 500 km or from 30 to 300 km.

Details of the individual units of the plant, including preferred embodiments, have already been described above and we refer to the respective passages.

In one preferred embodiment, the relocatable comminution unit comprises at least means selected from rotating water-jets, rotation knives and hole perforation plates.

In another preferred embodiment, the modular, relocatable plant comprises relocatable storage units for water-soluble, monoethylenically unsaturated monomers different from acrylamide.

In another embodiment, acrylamide is also manufactured at location A by hydrolyzing acrylonitrile in water in the presence of a biocatalyst capable of converting acrylonitrile to acrylamide.

The present invention therefore furthermore relates to a modular, relocatable plant for manufacturing aqueous polyacrylamide solutions by polymerizing an aqueous solution comprising at least acrylamide thereby obtaining an aqueous polyacrylamide gel and dissolving said aqueous polyacrylamide gel in water, comprising at least at a location A a relocatable storage unit for acrylonitrile, a relocatable bioconversion unit for hydrolyzing acrylonitrile in water in the presence of a biocatalyst capable of converting acrylonitrile to acrylamide, a relocatable unit for removing the biocatalyst from an aqueous acrylamide solution, a relocatable storage unit for an aqueous acrylamide solution, relocatable storage units for water-soluble, monoethylenically unsaturated monomers different from acrylamide, a relocatable storage unit for polymerization initiators, a relocatable monomer make-up unit for preparing an aqueous monomer solution comprising at least water and acrylamide, a relocatable polymerization unit for polymerizing the aqueous monomer solution in the presence of polymerization initiators, a relocatable unit for comminution of the aqueous polyacrylamide gel and mixing it with an aqueous liquid thereby obtaining an aqueous polyacrylamide concentrate, at locations A or B a transport unit for transporting an aqueous polyacrylamide concentrate from location A to location B.

at a location B means for removing the aqueous polyacrylamide concentrate from the transport unit, and optionally means for further diluting the aqueous polyacrylamide concentrate with an aqueous liquid.

Details of the individual units of the plant have already been described above and we refer to the respective passages.

In another embodiment, the present invention relates to a modular, relocatable plant for manufacturing aqueous polyacrylamide concentrates by polymerizing an aqueous solution comprising at least acrylamide thereby obtaining an aqueous polyacrylamide gel and mixing said aqueous polyacrylamide gel with an aqueous liquid, comprising at least a relocatable storage unit for an aqueous acrylamide solution, optionally relocatable storage units for water-soluble, monoethylenically unsaturated monomers different from acrylamide, a relocatable storage unit for polymerization initiators, a relocatable monomer make-up unit for preparing an aqueous monomer solution comprising at least water and acrylamide, a relocatable polymerization unit for polymerizing the aqueous monomer solution in the presence of polymerization initiators, a relocatable unit for comminution of the aqueous polyacrylamide gel and mixing it with an aqueous liquid thereby obtaining an aqueous polyacrylamide concentrate.

Said embodiment relates to the plant at location A. Details of the plant, including preferred embodiments have already been described in detail above, and we explicitly refer to the relevant passages of the specification above.

Use of the Aqueous Polyacrylamide Concentrates

The aqueous polyacrylamide concentrates manufactured according to the present invention may be used for various purposes, for example for mining applications, oilfield applications, water treatment, waste water cleanup, paper making or agricultural applications.

For application, the aqueous polyacrylamide concentrates may be further diluted at the site-of-use thereby obtaining diluted aqueous polyacrylamide solutions. In other embodiments, the aqueous polyacrylamide concentrates advantageously may be used as such without further dilution. Concentrates and/or solutions may also be formulated with further components. Further components may be selected by the skilled artisan according to the intended use.

Oilfield Applications

Examples of oilfield processes in which the aqueous polyacrylamide concentrates and/or solutions manufactured according to the present invention may be used include enhanced oil recovery, oil well drilling, the use as viscosifier for various purposes or the use as friction reducers, for example friction reducers for fracturing fluids.

Enhanced Oil Recovery

In one embodiment of the invention, the aqueous polyacrylamide concentrates manufactured according to the present invention may be used for enhanced oil recovery.

Accordingly, the present invention also relates to the use of aqueous polyacrylamide concentrates in a process of enhanced oil recovery comprising at least the following steps:

Providing an aqueous injection fluid by mixing at least an aqueous base fluid and an aqueous polyacrylamide concentrate having a concentration of 1.0 to 14.9% by weight of polyacrylamides, relating to the total of all components of the aqueous polyacrylamide concentrate, Injecting the aqueous injection fluid into a mineral oil deposit through at least one injection well, and withdrawing crude oil from the deposit through at least one production well, and wherein the aqueous polyacrylamide concentrate is prepared according to the process as described above.

Details of the manufacturing process for the polyacrylamide concentrate have already been disclosed above.

For enhanced oil recovery, a homopolymer of acrylamide may be used, however preferably water-soluble copolymers comprising at least 10%, preferably at least 20%, and more preferably at least 30% by weight of acrylamide and at least one additional water-soluble, monoethylenically unsaturated monomer different from acrylamide are used. Suitable water-soluble comonomers have already been mentioned above and we refer to the disclosure above.

In one embodiment, water-soluble comonomers may be selected from water-soluble, monoethylenically unsaturated monomers comprising at least one acid group, or salts thereof. The acidic groups are preferably selected from the group of —COOH, —503H and —PO$_3$H$_2$ or salts thereof. Preference is given to monomers comprising COOH groups and/or —SO$_3$H groups or salts thereof. Suitable counterions have already been mentioned above. Examples of such comonomers comprise acrylic acid, methacrylic acid, crotonic acid, itaconic acid, maleic acid, fumaric acid, vinylsulfonic acid, allylsulfonic acid, 2-acrylamido-2-methylpropanesulfonic acid (ATBS), 2-methacrylamido-2-methylpropane-sulfonic acid, 2-acrylamidobutanesulfonic acid, 3-acrylamido-3-methylbutane-sulfonic acid, 2-acrylamido-2,4,4-trimethylpentanesulfonic acid, vinylphosphonic acid, allylphosphonic acid, N-(meth)acrylamidoalkylphosphonic acids and (meth)acryloyloxyalkyl-phosphonic acids.

In a preferred embodiment, acrylic acid and/or ATBS or salts thereof may be used as comonomers.

In such copolymers, the amount of acrylamide usually is from 20% by wt. to 90% by wt. and the amount of acrylic acid and/or ATBS or salts thereof is from 10% by wt. to 80% by wt., relating to the amount of all monomers in the copolymer. Preferably, the amount of acrylamide is from 60% by wt. to 80% by wt. and the amount acrylic acid and/or ATBS or salts thereof is from 20% by wt. to 40% by wt.

In another embodiment, the copolymers to be used for enhanced oil recovery comprise at least one water-soluble, monoethylenically unsaturated monomer comprising at least one acid group, or salts thereof, preferably acrylic acid and/or ATBS or salts thereof, and at least one associative monomer. Examples of associative monomers have already been disclosed above. In one embodiment, at least one associative monomer of the general formula (III), (IV), or (V) is used, preferably at least one associative monomer of the general formula (V). Preferred embodiments of the associative monomers (III), (IV), and (V) have already been disclosed above and it is explicitly referred to that description.

In such polyacrylamides, the amount of acrylamide usually is from 40% by wt. to 89.9% by wt., the amount of acrylic acid and/or ATBS or salts thereof is from 10% by wt. to 59.9%, and the amount of associative monomers is from 0.1 to 5% by wt., relating to the amount of all monomers in the copolymer.

In one embodiment, the polyacrylamides for EOR comprise 45% to 55% by weight of acrylamide, 0.1 to 5%, preferably 0.1 to 2% by weight of at least one associative monomer of the general formula (V) mentioned above, including the preferred embodiments, and 40 to 54.9% by weight of acrylic acid or salts thereof.

For the method of enhanced oil recovery, at least one production well and at least one injection well are sunk into the mineral oil deposit. In general, a deposit will be provided with a plurality of injection wells and with a plurality of production wells. An aqueous fluid is injected into the mineral oil deposit through the at least one injection well, and mineral oil is withdrawn from the deposit through at least one production well. By virtue of the pressure generated by the aqueous fluid injected, called the "polymer flood", the mineral oil flows in the direction of the production well and is produced through the production well. In this context, the term "mineral oil" does not of course just mean a single-phase oil; instead, the term also encompasses the customary crude oil-water emulsions.

The aqueous injection fluid comprises an aqueous base fluid such as freshwater or water comprising salts, such as seawater or formation water. For use in enhanced oil recovery, the base fluid is mixed with the polyacrylamides and optionally further components. Examples of further components include biocides, stabilizers, free-radical scavengers, initiators, surfactants, cosolvents, bases and complexing agents. For mixing the aqueous injection fluid, either the aqueous polyacrylamide concentrate may be used or the aqueous polyacrylamide concentrate may be diluted in a first step with additional aqueous liquid and thereafter used for making the aqueous injection fluid.

For use in the enhanced oil recovery process, the aqueous polyacrylamide concentrates are mixed with the aqueous base fluid and optionally further components. In one embodiment, such mixing may be carried out by means of suitable mixing means, for example static mixers or mixing vessels. In another embodiment, the aqueous polyacrylamide concentrates are injected into the pipeline(s) which transport(s) the aqueous injection fluid to the injection well(s) at the desired concentration. Such pipelines may have a length of up to some kilometers. It has been found that the time needed for flowing through such pipeline often is sufficient for complete dissolution of the concentrate in the fluid. Of course, combinations are possible. By the way of example, the pipeline may comprise mixing elements such as static mixers.

In one embodiment of the method of enhanced oil recovery as described, location B may be at an injection well or in between a plurality of such injection wells.

Location A is apart from location B. Preferably, location A is a local hub which provides a plurality of different locations B with aqueous polyacrylamide gels. In one embodiment, location A may at a central point over a subterranean, oil-bearing formation or a central point in between different subterranean, oil-bearing formations and from location A, a plurality of oil wells to be treated is provided with aqueous polyacrylamide gels for further processing.

The final concentration of the polyacrylamide in the injection fluid is fixed such that the aqueous formulation has the desired viscosity for the end use. The viscosity of the formulation should generally be at least 5 mPas (measured at 25° C. and a shear rate of 7 s$^{-1}$), preferably at least 10 mPas.

In general, the concentration of the polyacrylamide in the injection fluid is 0.02% to 2% by weight based on the total sum of all the components in the aqueous formulation. The amount is preferably 0.05% to 0.5% by weight, more preferably 0.1% to 0.3% by weight and, for example, 0.1% to 0.2% by weight.

In one embodiment of the invention, the aqueous polyacrylamide concentrates may be used as such for the enhanced oil recovery process. Suitable concentrates preferably have a concentration from 3.1% by weight to 10% by weight, more preferably, the concentration is from 3.1% by weight to 7% by weight, and for example from 4% by weight to 6% by weight.

Friction Reducers for Hydraulic Fracturing

Hydraulic fracturing involves injecting fracturing fluid through a wellbore and into a formation under sufficiently high pressure to create fractures, thereby providing channels through which formation fluids such as oil, gas or water, can flow into the wellbore and thereafter be withdrawn. Fracturing fluids are designed to enable the initiation or extension of fractures and the simultaneous transport of suspended proppant into the fracture to keep the fracture open when the pressure is released.

In hydraulic fracturing operations it is important to ensure that the proppants are transported with the fracturing fluid into the formation and that they do not settle. Said effect can be achieved by using a thickened fluid having a high viscosity. In another embodiment of hydraulic fracturing, also known as "slickwater fracturing", fluids having only a low viscosity are used. Such fluids mainly comprise water. In order to achieve proppant transport into the formation, the pumping rates and the pressures used are significantly higher than for high-viscosity fluids. The high flow ensures proppant transport. On the other hand, the turbulent flow of the fracking fluid causes significant energy loss due to friction. In order to avoid or at least minimize such friction losses, friction reducers, for example high molecular weight polyacrylamides may be used which change turbulent flow to laminar flow.

In one embodiment of the invention, the aqueous polyacrylamide concentrates manufactured according to the present invention are used as friction reducers in slickwater fracturing applications.

Accordingly, the present invention also relates to the use of aqueous polyacrylamide concentrates as friction reducer in a process for fracturing subterranean formations comprising at least the following steps:

Providing an aqueous injection fluid by mixing at least an aqueous base fluid, a proppant and an aqueous polyacrylamide concentrate having a concentration of 1.0 to 14.9% by weight of polyacrylamides, relating to the total of all components of the aqueous polyacrylamide concentrate, wherein the concentration of the polyacrylamides in the aqueous fracturing fluid is from 20 ppm to 600 ppm, relating to the total of all components of the aqueous fracturing fluid except the proppants, injecting the aqueous fracturing fluid through a wellbore into a subterranean formation at a pressure sufficient to flow into the formation and to initiate or extend fractures in the formation, wherein the aqueous polyacrylamide concentrate is prepared by the process as described above.

The aqueous base fluid may be freshwater or water comprising salts, such as seawater or formation water or produced water.

Examples of suitable proppants comprise naturally-occurring sand grains, resin-coated sand, sintered bauxite, glass beads or ultra-lightweight polymer beads.

Details about the polyacrylamides have already been detailed above.

Fracturing fluids may be mixed using so-called blenders (often mounted on trucks), in which an aqueous base fluid, proppants, friction reducers and optionally further components are mixed. In one embodiment of the present invention, an aqueous base fluid, proppants, the aqueous polyacrylamide concentrate as described above and optionally further components are mixed with each other by means of a customary blender thereby obtaining an aqueous fracturing fluid.

The concentration of proppants in the fracturing fluid may be constant in course of the fracturing process. In other embodiments, the concentration of proppants in the fracturing fluid may be varied in course of the fracturing process. In one embodiment, the slickwater fracturing process may start with injection of a certain amount of fracturing fluid which does not comprise any proppants and proppants are added to the fracturing fluid only at a later stage of the fracturing process.

The concentration of the polyacrylamide friction reducer in the aqueous fracturing fluid is selected by the skilled artisan according to his/her needs. Usually, it is in the range from 20 ppm to 600 ppm, in particular from 20 ppm to 300 ppm, for example from 125 ppm to 250 ppm of polyacrylamides relating to the total of all components of the aqueous fracturing fluid except the proppants. The amount of the aqueous polyacrylamide concentrates for making the aqueous fracturing fluid is selected accordingly.

Mining Applications

In one embodiment, the method for preparing an aqueous polyacrylamide concentrates according to the present invention is carried out in areas where mining, mineral processing and/or metallurgy activities takes place. Consequently, the aqueous polyacrylamide concentrates as product obtained by the method of the present invention is preferably used for applications in the field of mining, mineral processing and/or metallurgy and the method for preparing the aqueous polyacrylamide concentrate is preferably used at the plant of the respective industry.

Preferably, mining activities comprises extraction of valuable minerals or other geological materials from certain deposits. Such deposits can contain ores, for example metal containing ores, sulfidic ores and/or non-sulfidic ores. The ores may comprise metals, coal, gemstones, limestone or other mineral material. Mining is generally required to obtain any material in particular mineral material that cannot be grown through agricultural processes or created artificially in a laboratory or factory. The aqueous polyacrylamide concentrate according to the present invention is preferably used to facilitate the recovery of mineral material, for beneficiation of ores and for further processing of ores to obtain the desired minerals or metals.

Typically, mining industries, mineral processing industries and/or metallurgy industries are active in the processing of ores and in the production of for example alumina, coal, iron, steel, base metals, precious metals, diamonds, non-metallic minerals and/or areas where aggregates play an important role. In such industries, the aqueous polyacrylamide concentrates manufactured according to the process of the present invention can be used for example at plants for alumina production, where alumina is extracted from the mineral bauxite using the Bayer caustic leach process, at plants where the coal washing process demands a closed water circuit and efficient tailings disposal to satisfy both economic and environmental demands, at plants for iron and steel production, where the agglomeration of fine iron concentrates to produce pellets of high quality is a major challenge for the iron ore industry, at plants for base metal production, where flocculants find several uses in base metal production, at plants for precious metals production, where reagents are used to enhance the tailings clarification process allowing the reuse of clean water, at diamond plants, where efficient water recovery is paramount in the arid areas where diamonds are often found, at plants for non-metallic mineral production where reagents enhance water recovery or aid the filtration processes to maximize process efficiency, at plants where aggregates have to be produced and flocculants and filter aids are needed to enhance solid/liquid separation.

Accordingly, the present invention relates to the use of an aqueous polyacrylamide concentrate for mining, mineral processing and/or metallurgy activities comprising the use for solid liquid separation, for tailings disposal, for polymer modified tailings deposition, for tailings management, as density and/or rheology modifier, as agglomeration aid, as binder and/or for material handling, wherein the aqueous polyacrylamide concentrate is prepared at the plant of the respective industry, comprising for example the following steps:

hydrolyzing acrylonitrile in water in presence of a biocatalyst capable of converting acrylonitrile to acrylamide so as to obtain an acrylamide solution, polymerizing the acrylamide solution so as to obtain a polyacrylamide gel, and dissolving the polyacrylamide gel by addition of water so as to obtain an aqueous polyacrylamide concentrate.

For the mining, mineral processing and/or metallurgy activities a homopolymer of acrylamide for example can be used. Further preferred are also copolymers of acrylamide. Such copolymers of acrylamide can be anionic, cationic or non-ionic. Anionic copolymers are for example co-polymers of acrylamide with increasing proportions of acrylate groups, which give the polymers negative charges, and thus anionic active character, in aqueous solution. Anionic copolymers of acrylamide can in particular be used for waste water treatment in metallurgy like iron ore plants, steel plants, plants for electroplating, for coal washing or as flocculants. Non-ionic polymers and/or copolymers of acrylamide can be used for example as nonionic flocculants suitable as settlement aids in many different mineral processing applications and are particularly effective under very low pH conditions, as encountered for example in acidic leach operations. Cationic copolymers of acrylamide have in particular an increasing proportion of cationic monomers. The cationic groups, which are thus introduced into the polymer, have positive charges in aqueous solution.

It is preferred, that the polymer obtained from the method of the present invention is used as flocculant in a process in which individual particles of a suspension form aggregates. The polymeric materials of the present invention forms for example bridges between individual particles in the way that segments of the polymer chain adsorb on different particles and help particles to aggregate. Consequently, the polymers of the present invention act as agglomeration aid, which may be a flocculant that carries active groups with a charge and which may counterbalance the charge of the individual particles of a suspension. The polymeric flocculant may also adsorb on particles and may cause destabilization either by bridging or by charge neutralization. In case the polymer is an anionic flocculant, it may react against a positively charged suspension (positive zeta potential) in presence of salts and metallic hydroxides as suspension particles, for example. In case the polymer of the present invention is for example a cationic flocculant, it may react against a negatively charged suspension (negative zeta potential) like in presence of for example silica or organic substances as suspension particles. For example, the polymer obtained from the method of the present invention may be an anionic flocculant that agglomerates clays which are electronegative.

Preferably, the method of the present invention and the obtained polymer and/or copolymer of acrylamide (polyacrylamide) is used for example in the Bayer process for alumina production. In particular, the polyacrylamide can be used as flocculant in the first step of the Bayer-Process, where the aluminum ore (bauxite) is washed with NaOH and soluble sodium aluminate as well as red mud is obtained. Advantageously, the flocculation of red mud is enhanced and a faster settling rate is achieved when acrylamide polymers and/or co-polymers are added. As red mud setting flocculants, polyacrylamide may be used for settling aluminum red mud slurries in alumina plants, provides high settling rates, offers better separation performance and reduces suspended solids significantly. Also, the liquor filtration operations are improved and with that the processing is made economically more efficient. It is further preferred that the polyacrylamides are used in decanters, in washers, for hydrate thickening, for green liquor filtration, as crystal growth modifiers, as thickener and/or as rheology modifier.

It is further preferred that the method of the present invention and the polymers of acrylamide are used in processes for solid liquid separation as for example flocculant or dewatering aid, which facilitate thickening, clarifying, filtration and centrifugation in order to enhance settling rates, to improve clarities and to reduce underflow volumes. In particular, in filtration processes the polyacrylamide homo- or co-polymer of the present invention increase filtration rates and yields, as well as reducing cake moisture contents.

Further preferred is the use of the method and the obtained polyacrylamide of the present invention in particular for material handling and as binder. In the mining industry, the movement of large volumes of material is required for processing the rock and/or ores which have been extracted from the deposits. The typical rock and/or ore processing for example starts with ore extraction, followed by crushing and grinding the ore, subsequent mineral processing (processing or the desired/valuable mineral material), then for example metal production and finally the disposal of waste material or tailings. It was a surprise that with the method of the present invention and in particular the obtained polyacrylamide the handling of the mineral material can be enhanced by increasing efficiency and yield, by improving product quality and by minimizing operating costs. Particularly, the present invention can be used for a safer working environment at the mine site and for reduction of environmental discharges.

Preferably, the method and the obtained polyacrylamide of the present invention can for example be used as thickener, as density and/or rheology modifier, for tailings management. The obtained polyacrylamide polymer can modify the behavior of the tailings for example by rheological adjustment. The obtained polyacrylamide polymers are able to rigidify tailings at the point of disposal by initiating instantaneous water release from the treated slurry. This accelerates the drying time of the tailings, results in a smaller tailings footprint and allows the released water to be returned to the process faster. This treatment is effective in improving tailings properties in industries producing alumina, nickel, gold, iron ore, mineral sands, oil sands or copper for example. Further benefits of the polymers obtained according to the present invention are for example maximized life of disposal area, slurry placement control, no re-working of deposit required, co-disposal of coarse and fine material, faster trafficable surface, reduced evaporative losses, increased volume for recycling, removed fines contamination, reduced fresh water requirement, lower land management cost, less mobile equipment, lower rehabilitation costs, quicker rehabilitation time, lower energy consumption, accelerated and increased overall water release, improved rate of consolidation, reduced rate of rise, reduced amount of post depositional settlement.

Preferably, the obtained product from the method of the present invention is used for agglomeration of fine particulate matter and for the suppression of dust. Particularly, polyacrylamide polymers or copolymers are used as organic binders to agglomerate a wide variety of mineral substrates. For example, the polyacrylamide polymers or copolymers are used for iron ore pelletization as a full or partial replacement for bentonite. The product from the method of the present invention can be used as binder, in particular as solid and liquid organic binders in briquetting, extrusion, pelletization, spheronization and/or granulation applications and gives for example excellent lubrication, molding and/or binding properties for processes such as coal-fines briquetting, carbon extrusion, graphite extrusion and/or nickel briquetting.

It is preferred that the method of the present invention and in particular the aqueous polyacrylamide concentrate obtained by the method is used for the beneficiation of ores which comprise for example coal, copper, alumina, gold, silver, lead, zinc, phosphate, potassium, nickel, iron, manganese, or other minerals.

Advantages of the Process According to the Invention

The process according to the present invention provides significant advantages as compared to known processes for the manufacture of polyacrylamide powders as well as compared to known processes for manufacturing polyacrylamide solutions on-site.

As already outlined above, drying aqueous polyacrylamide gels thereby obtaining polyacrylamide powders, transporting the powders to the site of use and re-dissolving the dry powders at the site of use is energy extensive and consequently the operational costs for drying are high. Furthermore, also the capital expenditure for the entire post-processing equipment including size reduction, drying, sieving, grinding is significant in relation to the total capital expenditure for the entire plant.

As compared to the known processes of manufacturing aqueous polyacrylamide solutions on-site by polymerizing aqueous acrylamide solutions and dissolving the gels obtained the process according to the present invention has the advantage that it is not necessary to move the entire plant when polyacrylamide solutions are no longer needed at a certain location, i.e. at an oil well, but at another location, i.e. another oil well.

The equipment for manufacturing the polyacrylamide gels and for manufacturing the aqueous polyacrylamide concentrates may remain at location A which typically is located at a central point in the area of use. From there, the aqueous polyacrylamide concentrates are distributed to the individual sites-of-use, e.g. to individual oil wells.

Furthermore, location A bundles everything being complicated (e.g. polymerization) and/or having a hazard potential (i.e. storage of potentially hazardous products) and therefore requires personnel experienced with chemical production. At location B, it is only necessary to remove the aqueous polyacrylamide concentrate from the transport unit, and either directly using it or optionally further diluting it and using the diluted solution.

Besides providing polyacrylamides as powders it is also known to manufacture inverse emulsions of polyacrylamides. Such inverse emulsions typically comprise about 30% to 40% by weight of polyacrylamides.

As will be detailed in the experimental part, the aqueous polyacrylamide concentrates have performance advantages as compared to inverse emulsions and also as compared to using powders.

EXAMPLES

The invention is illustrated in detail by the examples which follow.

Polyacrylamide friction reducers to be tested:

Example 1

Aqueous Polyacrylamide Concentrate Made by Mixing an Aqueous Polyacrylamide Gel with an Aqueous Liquid
Step 1:
Preparation of an Aqueous Gel of a Copolymer Comprising 69.4 wt. % (75.0 Mol %) of Acrylamide and 30.6 wt. % (25 Mol %) of Sodium Acrylate Stabilized with 0.25 wt. % Na-MBT Relating to Polymer by Adiabatic Gel Polymerization (Solids Content of 23% by Weight Relating to the Total of the Gel)

A 5 L beaker with magnetic stirrer, pH meter and thermometer was filled with 1600 g of distilled water, 702.04 g of sodium acrylate (35% by weight in water), and 1071.69 g of acrylamide (52% by weight in water). Then 10.5 g of diethylenetriaminepentaacetic acid pentasodium salt (Trilon C; 5% by weight in water), and 4 g of the stabilizer sodium 2-mercaptobenzothiazole (Na-MBT; 50% by weight in water) were added. After adjustment to pH 6.4 with sulfuric acid (20% by weight in water) and addition of the rest of the water to attain the desired monomer concentration of 23% by weight (total amount of water 1690.08 g minus the amount of water already added, minus the amount of acid required), the monomer solution was adjusted to a temperature of approx. −3° C. The solution was transferred to a Dewar vessel, the temperature sensor for the temperature recording was inserted, and the flask was purged with nitrogen for 45 minutes. The polymerization was initiated at 0° C. with 21 g of a 10% aqueous solution of 2,2'-azobis(2-methylpropionamidine) dihydrochloride (Wako V-50; 10 h $t_{1/2}$ in water 56° C.), 1.75 g of t-butyl hydroperoxide (1% by weight in water) and 1.05 g of a 1% sodium sulfite solution. With the onset of the polymerization, the temperature rose to 54.6° C. within about 63 min. A solid polymer gel block was obtained.

After polymerization, the gel block was incubated 4 hours at 60° C. Then, the block was cut vertically into two pieces. One part was sealed in a plastic bag for use in step 2. The other part was kept for comparative example 2.

Step 2:

Preparation of an Aqueous Polyacrylamide Concentrate (Polymer Concentration: 5 wt. %)

The aqueous polyacrylamide gel obtained in course of step 1 was first chopped to small particles ranging in size from 2 to 5 mm. To give a final concentration of 5.0 weight % polymer, 58.82 g of these chopped particles were then dispersed into a 600 ml beaker containing 241.18 g of distilled water. The gel particles were added while mixing via an overhead mixer with a 75 mm diameter half-moon propeller. The mixing rate was initially set at 300 rpm for the first 5 min, then lowered to 30 rpm for an additional 18 hours.

Comparative Example 1

Inverse Emulsion of Polyacrylamides

Inverse emulsion of a copolymer comprising 69.4 wt. % (75.0 mol %) of acrylamide and 30.6 wt. % (25 mol %) of sodium acrylate stabilized with 0.25 wt. % Na-MBT relating to polymer (solids content 23% by weight relating to the total of the inverse emulsion).

A 600 mL beaker with magnetic stirrer, pH meter and thermometer was charged with 150.44 g of sodium acrylate (35% by weight in water), 128.97 g of distilled water, 229.65 g of acrylamide (52% by weight in water), 0.5 g of diethylenetriaminepentaacetic acid pentasodium salt (Trilon C; 5% by weight in water), and 0.86 g of the stabilizer sodium 2-mercaptobenzothiazole (Na-MBT; 50% by weight in water).

After adjustment to pH 6.4 with sulfuric acid (20% by weight in water), the rest of the water to attain the desired monomer concentration of 23% by weight (total amount of water 138.61 g minus the amount of water already added, minus the amount of acid required) was added.

A high 1 L beaker was charged with 12.2 g sorbitan monooleate (Span® 80) and 189.9 g of a high-boiling dearomatized hydrocarbon mixture (Exxsol® D100) was added and stirred with a spatula.

The beaker with the oil solution was fixed in a Silverson high shear mixer. While mixing the oil solution at 4000 rpm, the aqueous solution was poured in quickly. Then, the Silverson high shear mixer is turned up to 8000 rpm for 2 min 48 sec.

The emulsion was transferred to a double jacketed reactor, stirred at 200 rpm and adjusted to the initiation temperature of 10° C. During this time the emulsion was purged with nitrogen (for 60 minutes). The polymerization was dropwise initiated with 9 g of a 0.1% sodium bisulfite solution and 5 g of 0.1% t-butyl hydroperoxide solution. The initiators were added with a squeezing pump, controlled by hand. When the respective 0.1% solutions were empty, the initiators were changed to 9 g of a 1% sodium bisulfite solution and 5 g of a 1% t-butyl hydroperoxide solution. Thereby, the temperature rose 1° C. per minute up to 40° C., from there the temperature was maintained at 40° C. When the second initiator was added completely, the emulsion was stirred for additional 60 minutes at 40° C. The emulsion was then filtered through a 190 μm filter.

Activation of the Inverse Emulsion

The activation was carried out 24 h prior to use in the Friction Loop experiment. For activation, 97.75 g of the inverse emulsion was poured in a glass beaker and stirred with an over-head stirrer at 650 rpm. With a 5 mL plastic syringe, 2.25 g of a commercially available activator was added at once to the vortex of the inverse emulsion. The mixture was stirred for additional 8 minutes.

Comparative Example 2

Aqueous Polyacrylamide Concentrate Made by Mixing Polyacrylamide Powder with an Aqueous Liquid Step 1:

Preparation of an Aqueous Gel of a Copolymer Comprising 69.4 wt. % (75.0 Mol %) of Acrylamide and 30.6 wt. % (25 Mol %) of Sodium Acrylate Stabilized with 0.25 wt. % Na-MBT Relating to Polymer by Adiabatic Gel Polymerization (Solids Content of 23% by Weight Relating to the Total of the Gel)

Step 1 was carried out in the same manner as in example 1. A part of the polymer gel obtained in step 1 of example 1 was used for example 1 and the other part for the present comparative example 2.

Step 2:

Drying the Aqueous Gel

The gel obtained in example 1 was comminuted with a meat grinder. The particles were dried for two hours at 55° C. in a fluid bed dryer. After drying, the dried particles were grinded in a lab mill and filtered with a 1 mm sieve. A polyacrylamide powder with an active content of 94.6% by weight (the remainder being moisture) was obtained.

Step 3:

Preparation of an Aqueous Polyacrylamide Concentrate (Polymer Concentration: 5 wt. %)

An amount of 284.21 g of water was added into a 600 ml beaker while mixing via an overhead mixer with a 75 mm diameter half-moon propeller. The mixing rate was initially set at 300 rpm. Thereafter 15.79 g of the polyacrylamide powder (i.e. the amount to give a final concentration of 5.0 weight % of polyacrylamides in the concentrate) obtained in course of step 2 was slowly added to the vortex over a few seconds to avoid the formation of lumps. After 5 min, the mixing rate was lowered to 30 rpms for an additional 18 hours.

Comparative Example 3

Aqueous Polyacrylamide Concentrate Made by Mixing Polyacrylamide Powder with an Aqueous Liquid Step 1:

Preparation of an Aqueous Gel of a Copolymer Comprising 69.4 wt. % (75.0 Mol %) of Acrylamide and 30.6 wt. % (25 Mol %) of Sodium Acrylate Stabilized with 0.25 wt. % Na-MBT Relating to Polymer by Adiabatic Gel Polymerization (Solids Content of 30% by Weight Relating to the Total of the Gel)

A 5 L beaker with magnetic stirrer, pH meter and thermometer was filled with 1100 g of distilled water, 915.71 g of sodium acrylate (35% by weight in water), and 1397.85 g of acrylamide (52% by weight in water). Then 10.5 g of diethylenetriaminepentaacetic acid pentasodium salt (Trilon C; 5% by weight in water), and 5.2 g of the stabilizer sodium 2-mercaptobenzothiazole (Na-MBT; 50% by weight in water) were added.

After adjustment to pH 6.4 with sulfuric acid (20% by weight in water) and addition of the rest of the water to attain the desired monomer concentration of 30% by weight (total amount of water 1149.05 g minus the amount of water already added, minus the amount of acid required), the monomer solution was adjusted to a temperature of approx.

−3° C. The solution was transferred to a Dewar vessel, the temperature sensor for the temperature recording was inserted, and the flask was purged with nitrogen for 45 minutes. The polymerization was initiated at 0° C. with 21 g of a 10% aqueous solution of 2,2'-azobis(2-methylpropionamidine) dihydrochloride (Wako V-50; 10 h $t_{1/2}$ in water 56° C.), 1.75 g of t-butyl hydroperoxide (1% by weight in water) and 1.05 g of a 1% sodium sulfite solution. With the onset of the polymerization, the temperature rose to 84.4° C. within about 20 min. A solid polymer gel block was obtained.

After polymerization, the gel block was incubated 4 hours at 80° C. Then, the block was comminuted with a meat grinder. The particles were dried for two hours at 55° C. in a fluid bed dryer. After drying, the dried particles were grinded in a lab mill and filtered with a 1 mm sieve. A polyacrylamide with an active content of 95.0 wt. % was obtained.

Step 2:

Preparation of an Aqueous Polyacrylamide Concentrate (Polymer Concentration: 5 wt. %)

An amount of 284.21 g of water was added into a 600 ml beaker while mixing via an overhead mixer with a 75 mm diameter half-moon propeller. The mixing rate was initially set at 300 rpm. Thereafter 15.79 g of the polyacrylamide powder (i.e. the amount to give a final concentration of 5.0 weight % of polyacrylamides in the concentrate) obtained in course of step 2 was slowly added to the vortex over a few seconds to avoid the formation of lumps. After 5 min, the mixing rate was lowered to 30 rpms for an additional 18 hours.

Friction Loop Apparatus

The friction reduction performance of the friction reducing agent was assessed using a Chandler model M5600 friction loop, which circulates fluid through a section of known diameter pipe to determine the effectiveness and longevity of a friction reducing agent added to a test fluid. Fluid in the loop flows from a ~37.8 l (~10 gallon) reservoir through a pump, mass flow meter and then two ~250 cm (10 feet) long sections of pipe before returning to the reservoir to be recirculated. Pressure drop is measured over the two sections of pipe. One is 1.27 cm outer diameter (½ inch), the other is 1.91 cm outer diameter (¾" inch), giving different ranges of Reynolds number.

The friction loop was loaded with 37.85 l (10 gallons) of aqueous test fluid (fresh water or brines). The flow rate was set to 37.85 l per minute (10 gallons per minute) and once a stable, initial pressure was recorded. Thereafter, the friction reducing composition to be tested was injected into the vortex of the fluid reservoir using a plastic syringe.

The injection time was taken as the start of the test (time=0 seconds). The subsequent drop in pressure measured the performance of the friction reducing composition. The pressure data from the 1.27 cm pipe is reported, because it reflected a higher Reynolds number than the 1.91 cm pipe.

Pressure data was converted to friction reduction using the formula:

$$\% \text{ Friction Reduction } (\% \ FR) = \frac{\text{Initial Pressure with no } FR - \text{Pressure with } FR}{\text{Initial Pressure with no } FR}$$

Friction Loop Tests 26.08 g of each of the aqueous polyacrylamide concentrates obtained in examples 1 to 3 (each having a concentration of 5 wt. % of polyacrylamides) was used for the friction loop testing. This dosage amount corresponds to a final concentration of 35 ppm polymer once diluted in the friction loop with additional fresh water.

The aqueous polyacrylamide concentrate was added directly to vortex of the friction loop mixing tank at time=0, as mentioned in the above description of the Friction Loop.

5.67 ml of the activated inverse emulsion sample (comparative example 1) was directly injected into the vortex of the flow loop mixing tank, to achieve also a final concentration of 35 ppm polymer.

All results (percentage of friction reduction vs. time) are summarized in FIG. 17.

Discussion of the Results Obtained

FIG. 17 shows a comparison of the % Friction Reduction of example 1 and comparative examples 1, 2, and 3 as a function of time. Each sample was measured individually under the same experimental conditions and at the same effective dosage concentration.

The aqueous polyacrylamide concentrate obtained from an aqueous gel (example 1) yielded higher maximum friction reduction, as well as at a faster rate when compared to the inverse emulsion (comparative example 1).

Example 1 also gave better results than the two samples prepared from powders (comparative examples 2 and comparative 3) over the 10 min interval.

The invention claimed is:

1. A process for producing an aqueous polyacrylamide concentrate by polymerizing an aqueous solution comprising at least acrylamide thereby obtaining an aqueous polyacrylamide gel and mixing said aqueous polyacrylamide gel with an aqueous liquid, characterized in that the process comprises at least the following steps:
   [1] Radically polymerizing an aqueous monomer solution in the presence of suitable initiators for radical polymerization under adiabatic conditions in a polymerization unit at a location A, wherein the aqueous monomer solution comprises at least water and 15% to 50% by weight-relating to the total of all components of the aqueous monomer solution-of water-soluble, monoethylenically unsaturated monomers at a location A, wherein said water-soluble, monoethylenically unsaturated monomers comprise at least acrylamide, thereby obtaining an aqueous polyacrylamide gel which is hold in the polymerization unit,
   [2] removing the aqueous polyacrylamide gel from the polymerization unit at the location A,
   [3] comminuting the aqueous polyacrylamide gel and mixing it with an aqueous liquid at the location A, thereby obtaining an aqueous polyacrylamide concentrate having a concentration of 1.0 to 14.9% by weight of polyacrylamides, relating to the total of all components of the aqueous polyacrylamide concentrate,
   [4] transporting the aqueous polyacrylamide concentrate in a transport unit having a volume from 1 m³ to 40 m³ by transport means selected from the group of trucks, railcars or ships from location A to a different location B, and
   [5] removing the aqueous polyacrylamide concentrate from the transport unit at the location B.

2. The process according to claim 1, wherein the concentration of the aqueous polyacrylamide concentrate is from 2.1 to 10% by weight of polyacrylamides, relating to the total of all components of the aqueous polyacrylamide concentrate.

3. The process according to claim 1, wherein the concentration of the aqueous polyacrylamide concentrate is from 3.1 to 7% by weight of polyacrylamides, relating to the total of all components of the aqueous polyacrylamide concentrate.

4. The process according to claim 1, wherein step [1] is performed in a polymerization unit comprising a cylindrical upper part, a conical part at its lower end, feeds for the aqueous monomer solution, a bottom opening for removing the polyacrylamide gel, and means allowing to deploy the polymerization unit in a vertical manner.

5. The process according to claim 4, wherein the aqueous polyacrylamide gel is removed from the polymerization unit by applying gas pressure onto the gel and pressing it through the bottom opening.

6. The process according to claim 1, wherein comminuting the aqueous polyacrylamide gel in course of step [3] is carried out by conveying the aqueous polyacrylamide gel through at least one comminution unit together with an aqueous liquid thereby yielding a mixture of pieces of aqueous polyacrylamide gel in an aqueous polyacrylamide solution.

7. The process according to claim 6, wherein the at least one comminution unit comprises means for comminuting aqueous polymer gels selected from static cutting devices, dynamic cutting devices, perforated plates, static mixers, water-jet cutting devices or combinations thereof.

8. The process according to claim 6, wherein at least one of the at least one comminution unit is a water-jet cutting device.

9. The process according to claim 6, wherein the process comprises an additional step of homogenizing the mixture of pieces of aqueous polyacrylamide gel in an aqueous polyacrylamide solution by transferring the mixture to a vessel and allowing the mixture to stand in the vessel, or mixing the contents of the vessel by suitable mixing means.

10. The process according to claim 1, wherein the transport unit has a volume from 10 to 30 m$^3$.

11. The process according to claim 1, wherein the transport unit is an ISO tank container.

12. The process according to claim 1, wherein the transport unit is a tank fixed on a truck which comprises an outlet at the rear end of the truck and means for tilting the tank.

13. Process according to claim 1, wherein the transport unit is filled by pumping the aqueous polyacrylamide concentrate into the transport unit.

14. The process according to claim 1, wherein the process comprises an additional step [6] of diluting the aqueous polyacrylamide concentrate with an aqueous liquid at the location B.

15. The process according to claim 1, wherein the acrylamide needed for the process is obtained by hydrolyzing acrylonitrile in water in the presence of a biocatalyst capable of converting acrylonitrile to acrylamide.

16. The process according to claim 1, wherein the process comprises an additional step [0] conducted at location A comprising hydrolyzing acrylonitrile in water in the presence of a biocatalyst capable of converting acrylonitrile to acrylamide, thereby obtaining an aqueous acrylamide solution, and wherein said aqueous acrylamide solution is used for making the aqueous monomer solution for step [1].

17. A process for producing an aqueous polyacrylamide concentrate by polymerizing an aqueous solution comprising at least acrylamide thereby obtaining an aqueous polyacrylamide gel and mixing said aqueous polyacrylamide gel with an aqueous liquid, characterized in that the process comprises at least the following steps:

[1] radically polymerizing an aqueous monomer solution in the presence of suitable initiators for radical polymerization under adiabatic conditions in a polymerization unit at a location A, wherein the aqueous monomer solution comprises at least water and 15% to 50% by weight-relating to the total of all components of the aqueous monomer solution-of water-soluble, monoethylenically unsaturated monomers at a location A, wherein said water-soluble, monoethylenically unsaturated monomers comprise at least acrylamide, wherein the polymerization unit comprises a cylindrical upper part, a conical part at its lower end, feeds for the aqueous monomer solution and a bottom opening, thereby obtaining an aqueous polyacrylamide gel which is hold in the polymerization unit,

[2] removing the aqueous polyacrylamide gel from the polymerization unit through the bottom opening by means of gas pressure at the location A,

[3] comminuting the aqueous polyacrylamide gel and mixing it with an aqueous liquid at the location A, thereby obtaining an aqueous polyacrylamide concentrate having a concentration of 1.0 to 14.9% by weight of polyacrylamides, relating to the total of all components of the aqueous polyacrylamide concentrate,

[4] transporting the aqueous polyacrylamide concentrate in a transport unit having a volume form 1 m$^3$ to 40 m$^3$ by transport means selected from the group of trucks, railcars or ships from location A to a different location B, and

[5] removing the aqueous polyacrylamide concentrate from the transport unit at the location B.

18. A process for producing an aqueous polyacrylamide concentrate by polymerizing an aqueous solution comprising at least acrylamide thereby obtaining an aqueous polyacrylamide gel and mixing said aqueous polyacrylamide gel with an aqueous liquid, characterized in that the process comprises at least the following steps:

[1] radically polymerizing an aqueous monomer solution in the presence of suitable initiators for radical polymerization under adiabatic conditions in a polymerization unit at a location A, wherein the aqueous monomer solution comprises at least water and 15% to 50% by weight-relating to the total of all components of the aqueous monomer solution-of water-soluble, monoethylenically unsaturated monomers, wherein said water-soluble, monoethylenically unsaturated monomers comprise at least acrylamide, wherein the polymerization unit comprises a cylindrical upper part, a conical part at its lower end, feeds for the aqueous monomer solution and a bottom opening, thereby obtaining an aqueous polyacrylamide gel which is hold in the polymerization unit,

[2] removing the aqueous polyacrylamide gel from the polymerization unit through the bottom opening by means of gas pressure,

[3] conveying the aqueous polyacrylamide gel through at least one comminution unit together with an aqueous liquid thereby yielding a mixture of pieces of aqueous polyacrylamide gel in an aqueous polyacrylamide solution followed by homogenization of the mixture obtained by transferring the mixture to a vessel and allowing the mixture to stand in the vessel, or mixing the contents of the vessel by suitable mixing means, thereby obtaining an aqueous polyacrylamide concentrate having a concentration of 3.1 to 14.9% by weight of polyacrylamides, relating to the total of all components of the aqueous polyacrylamide concentrate.

19. A modular, relocatable plant for manufacturing aqueous polyacrylamide concentrates by polymerizing an aqueous solution comprising at least acrylamide thereby obtaining an aqueous polyacrylamide gel and mixing said aqueous polyacrylamide gel with an aqueous liquid, comprising at least at a location A
- a relocatable storage unit for an aqueous acrylamide solution,
- optionally relocatable storage units for water-soluble, monoethylenically unsaturated monomers different from acrylamide,
- a relocatable storage unit for polymerization initiators,
- a relocatable monomer make-up unit for preparing an aqueous monomer solution comprising at least water and acrylamide,
- a relocatable polymerization unit for polymerizing the aqueous monomer solution in the presence of polymerization initiators,
- a relocatable unit for comminution of the aqueous polyacrylamide gel and mixing it with an aqueous liquid thereby obtaining an aqueous polyacrylamide concentrate, at locations A or B
- a transport unit for transporting an aqueous polyacrylamide concentrate from location A to location B, at a location B
- means for removing the aqueous polyacrylamide concentrate from the transport unit.

20. A modular, relocatable plant according to claim 19, wherein the plant additionally comprises a dissolution unit at location B.

21. The modular relocatable plant according to claim 19 wherein the relocatable comminution unit comprises at least one means selected from rotating water-jets, rotating knives or and a hole perforation plate.

22. A modular, relocatable plant for manufacturing aqueous polyacrylamide concentrates by polymerizing an aqueous solution comprising at least acrylamide thereby obtaining an aqueous polyacrylamide gel and mixing said aqueous polyacrylamide gel with an aqueous liquid, comprising at least

- a relocatable storage unit for an aqueous acrylamide solution,
- optionally relocatable storage units for water-soluble, monoethylenically unsaturated monomers different from acrylamide,
- a relocatable storage unit for polymerization initiators,
- a relocatable monomer make-up unit for preparing an aqueous monomer solution comprising at least water and acrylamide,
- a relocatable polymerization unit for polymerizing the aqueous monomer solution in the presence of polymerization initiators,
- a relocatable unit for comminution of the aqueous polyacrylamide gel and mixing it with an aqueous liquid thereby obtaining an aqueous polyacrylamide concentrate.

* * * * *